(12) United States Patent
Yano et al.

(10) Patent No.: US 6,858,417 B2
(45) Date of Patent: Feb. 22, 2005

(54) DNA FRAGMENT CARRYING TOLUENE MONOOXYGENASE, GENE, RECOMBINANT PLASMID, TRANSFORMED MICROORGANISM, METHOD FOR DEGRADING CHLORINATED ALIPHATIC HYDROCARBON COMPOUNDS AND AROMATIC COMPOUNDS, AND METHOD FOR ENVIRONMENTAL REMEDIATION

(75) Inventors: Tetsuya Yano, Kanagawa-ken (JP); Tsuyoshi Nomoto, Tokyo (JP); Takeshi Imamura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/223,371

(22) Filed: Aug. 20, 2002

(65) Prior Publication Data

US 2003/0170877 A1 Sep. 11, 2003

Related U.S. Application Data

(62) Division of application No. 09/453,956, filed on Dec. 3, 1999, now Pat. No. 6,472,191.

(30) Foreign Application Priority Data

Dec. 3, 1998 (JP) ........................................... 10-344506

(51) Int. Cl.[7] .......................... C12N 9/02; C12N 15/53; C12S 13/00
(52) U.S. Cl. ................. 435/189; 435/262.5; 435/252.3; 536/23.2
(58) Field of Search ...................... 536/27.2; 438/252.3, 438/289, 262.5

(56) References Cited

U.S. PATENT DOCUMENTS

| | | | |
|---|---|---|---|
| 4,877,736 A | 10/1989 | Fliermans | 435/183 |
| 4,925,802 A | 5/1990 | Nelson et al. | 435/262 |
| 5,543,317 A | 8/1996 | Shields et al. | 435/240.2 |
| 5,612,204 A | 3/1997 | Saeki et al. | 435/132 |
| 6,004,772 A | 12/1999 | Imamura et al. | 435/34 |

FOREIGN PATENT DOCUMENTS

| | | |
|---|---|---|
| EP | 0366718 | 10/1989 |
| EP | 0567102 | 4/1993 |
| EP | 0822253 | 2/1998 |
| JP | 02-92274 | 4/1990 |
| JP | 03-292970 | 12/1991 |
| JP | 06-22769 | 2/1994 |
| JP | 06-70753 | 3/1994 |
| JP | 06-105691 | 4/1994 |
| JP | 07-123976 | 5/1995 |
| JP | 07-143882 | 6/1995 |
| JP | 07-236895 | 9/1995 |
| JP | 08-70881 | 3/1996 |
| JP | 08-294381 | 8/1996 |
| JP | 08-294387 | 11/1996 |
| WO | WO 89-087927 | 9/1989 |
| WO | WO 89-09827 | 10/1989 |
| WO | WO 92-19738 | 11/1992 |

OTHER PUBLICATIONS

Hanada et al., "Phylogen tic . . . Contaminant", J. Ferm. & Bioeng., vol. 86, No. 6 (1998) 539–544.
Hino et al., "Phenol . . . Properties", Microb., vol. 144, No. 7 (1998) 1765–1772.

Primary Examiner—Charles L. Patterson, Jr.
(74) Attorney, Agent, or Firm—Fitzpatrick, Cella, Harper and Scinto

(57) ABSTRACT

A recombinant DNA is constructed by using a toluene monooxygenase gene isolated from *Ralstonia eutropha* strain TB64 and employed to provide the transformant which can express toluene monooxygenase useful for cleaning of aqueous media such as drain and waste water containing halogenated aliphatic hydrocarbon compounds or aromatic compounds, for remediation of soil polluted with such compounds, and cleaning of air (gas phase) polluted with volatile organic chlorine compounds.

42 Claims, 36 Drawing Sheets

FIG. 2

| FIG. 2A |
|---|
| FIG. 2B |
| FIG. 2C |
| FIG. 2D |
| FIG. 2E |
| FIG. 2F |
| FIG. 2G |
| FIG. 2H |
| FIG. 2I |
| FIG. 2J |
| FIG. 2K |
| FIG. 2L |
| FIG. 2M |
| FIG. 2N |
| FIG. 2O |
| FIG. 2P |
| FIG. 2Q |
| FIG. 2R |
| FIG. 2S |

FIG. 2A

```
GATCAACGAT TTGAAGCGTC CGCATAAGAG CGGTACCAAG TCCGGGAGCG TGCTGGGTAA      60

CCAAGCATTT TGCAGGCGCG CAAGCCAACT TCGACTCAGT ATTTTCCCTG AAATATCGAG     120

ATTTCCGGGC CATGGGCTGG CACCGCTGGC ACGCCCGCTG CAATGAAAGG GGCACGGAGG     180

CGACATCGAC CCATTGACT ATG ACC CTG CAG ACC CCA GCC AAC CAA GCA TCC     232
                     Met Thr Leu Gln Thr Pro Ala Asn Gln Ala Ser
                      1               5                      10

GAT CCC TGC CGC AAG TTC GTC CGG GTC ACC GGC CTC AAC CCG CGC GGA      280
Asp Pro Cys Arg Lys Phe Val Arg Val Thr Gly Leu Asn Pro Arg Gly
             15                  20                  25

TTC GTC GAA TTC GAG TTC GCG ATC GGC GGG CCG GAG ATG TTC GTC GAA      328
Phe Val Glu Phe Glu Phe Ala Ile Gly Gly Pro Glu Met Phe Val Glu
         30                  35                  40

CTG ACC CTG CCC ATA GAC GCA TTC GAC GCG TTC TGC ACC ACG CAG AAC      376
Leu Thr Leu Pro Ile Asp Ala Phe Asp Ala Phe Cys Thr Thr Gln Asn
         45                  50                  55

GTC GTC CGG CTG GAT GAC TCC GGC AGC GAC TTC CAC CGC GAC CCC ACG      424
Val Val Arg Leu Asp Asp Ser Gly Ser Asp Phe His Arg Asp Pro Thr
 60                  65                  70                  75
```

FIG. 2B

```
ACC CTC AGG AGC AAC CCG TGA                                    445
Thr Leu Arg Ser Asn Pro Stop
            80

GTG ACA ATC GAG CTG AAA ACC GTC GAC ATC                        475
Met Thr Ile Glu Leu Lys Thr Val Asp Ile
 1           5                   10

AAG CCG CTA CGG CAG ACC TAC GCG CAT GTG GCG CGG CAT ATC GGT GGC    523
Lys Pro Leu Arg Gln Thr Tyr Ala His Val Ala Arg His Ile Gly Gly
                15                  20                  25

GAC AAG ACG GCC TCG CGC TAC CAG GAA GGC ATG ATG GGC GCG CAG CCC    571
Asp Lys Thr Ala Ser Arg Tyr Gln Glu Gly Met Met Gly Ala Gln Pro
            30                  35                  40

GAG ACC AAC TTC CAC TAT CGC CCA ACC TGG GAT CCG GCG CAC CAA ATC    619
Glu Thr Asn Phe His Tyr Arg Pro Thr Trp Asp Pro Ala His Gln Ile
            45                  50                  55

TTC GAC GCC TCG CGC TCG GCG ATC CGC ATG GCG AGC TGG TAC GTG CTG    667
Phe Asp Ala Ser Arg Ser Ala Ile Arg Met Ala Ser Trp Tyr Val Leu
            60                  65                  70
```

FIG. 2C

| | | |
|---|---|---|
| AAG GAC CCG CGC CAG TAC TAC TAC GCC TCG TGG ACC ACG GCC CGC GCG | | 714 |
| Lys Asp Pro Arg Gln Tyr Tyr Tyr Ala Ser Trp Thr Thr Ala Arg Ala | | |
| 75      80      85      90 | | |
| CGC CAG CAG GAC ACG ATG GAA TCG AAC TTC GAG TTC GTC GAA TCG CGC | | 763 |
| Arg Gln Gln Asp Thr Met Glu Ser Asn Phe Glu Phe Val Glu Ser Arg | | |
| 95      100      105 | | |
| CGG ATG ATC GAC CGG ATG CCG GCG GAG GTG GCC AAA CAC GCG CTC GAC | | 811 |
| Arg Met Ile Asp Arg Met Pro Ala Glu Val Ala Lys His Ala Leu Asp | | |
| 110      115      120 | | |
| CTT CTG GTA CCG CTG CGC CAC GCC GCA TGG GGC GCG AAC ATG AAC AAC | | 859 |
| Leu Leu Val Pro Leu Arg His Ala Ala Trp Gly Ala Asn Met Asn Asn | | |
| 125      130      135 | | |
| GCG CAG GTC TGC GCA CTG GGT TAC GGC ACC GCC TTC ACC GCG GCG GCG | | 907 |
| Ala Gln Val Cys Ala Leu Gly Tyr Gly Thr Ala Phe Thr Ala Ala Ala | | |
| 140      145      150 | | |
| ATG TTC CAC GCG ATG GAC AAC CTC GGC GTT GCG CAA TAC CTG ACG CGC | | 955 |
| Met Phe His Ala Met Asp Asn Leu Gly Val Ala Gln Tyr Leu Thr Arg | | |
| 155      160      165      170 | | |

FIG. 2D

```
CTG GCG CTC GCA GTG GCC GGC CCG GAG GTG CTC GAC GCG GGC CGG CAC        1003
Leu Ala Leu Ala Val Ala Gly Pro Glu Val Leu Asp Ala Gly Arg His
            175                 180                 185

GCC TGG CTC GAA CAT CCG GCG TGG CAG CCG CTG CGC CAC TAC ATC GAG        1051
Ala Trp Leu Glu His Pro Ala Trp Gln Pro Leu Arg His Tyr Ile Glu
            190                 195                 200

GAC ACC TTC GTC GTC GAC GAC CCG GTC GAA CTG TTC GTC GCC CAG AAC        1099
Asp Thr Phe Val Val Asp Asp Pro Val Glu Leu Phe Val Ala Gln Asn
            205                 210                 215

CTG GCG CTT GAC GGC ATG CTT TAC CCG CTG GTC TAC GAC CGC TTT GTC        1143
Leu Ala Leu Asp Gly Met Leu Tyr Pro Leu Val Tyr Asp Arg Phe Val
            220                 225                 230

GAC GAA CGG ATC GCC CTG GGC GGC GGC TCC GCG ATC GCG ATG CTG ACG        1195
Asp Glu Arg Ile Ala Leu Gly Gly Gly Ser Ala Ile Ala Met Leu Thr
            235                 240                 245                 250

GCC TTC ATG CCC GAG TGG CAC GAG GAG TCG AAA CGC TGG GTC GAT GCC        1243
Ala Phe Met Pro Glu Trp His Glu Glu Ser Lys Arg Trp Val Asp Ala
            255                 260                 265
```

FIG. 2E

| | |
|---|---|
| GTG GTG AAG ACG ATG GCG GCC GAG TCC GAA GAG AAC AAG GCG CTG CTG | 1291 |
| Val Val Lys Thr Met Ala Ala Glu Ser Glu Glu Asn Lys Ala Leu Leu | |
| 270 275 280 | |
| GCG CAC TGG ACC CGC GAC TGG GCC GGG CGT GCG TTT GCC GCG CTG CAG | 1339 |
| Ala His Trp Thr Arg Asp Trp Ala Gly Arg Ala Phe Ala Ala Leu Gln | |
| 285 290 295 | |
| CCG GTC GCA GAG CTG GCC TTC CCG ACC CAT GCG CCC GAA GTG CTC GAC | 1387 |
| Pro Val Ala Glu Leu Ala Phe Pro Thr His Ala Pro Glu Val Leu Asp | |
| 300 305 310 | |
| GCG GTG CGC GAG CAG TTC CAG ACC CGG ATT TCG AAA CTC GGC ATC GCG | 1435 |
| Ala Val Arg Glu Gln Phe Gln Thr Arg Ile Ser Lys Leu Gly Ile Ala | |
| 315 320 325 330 | |
| CTC TGA TCCCGCCCCT CACTCGCTCT GAAGGAAAAC AC | 1473 |
| Leu Stop | |
| ATG TCC AAC GTA TTC ATC GCC TTC | 1497 |
| Met Ser Asn Val Phe Ile Ala Phe | |
| 1 5 | |
| CAG GCC AAC GAG GAG TCC CGT CCG GTG GTC GAG GCC ATC CTC GCC GAC | 1545 |
| Gln Ala Asn Glu Glu Ser Arg Pro Val Val Glu Ala Ile Leu Ala Asp | |

FIG. 2F

```
          10                  15                  20
AAC CCG GAC GCG GTG CTG GTC GAG TCC CCG GGA ATG GTC AAG ATC GAC         1593
Asn Pro Asp Ala Val Leu Val Glu Ser Pro Gly Met Val Lys Ile Asp 25                  30                  35                  40
GCG CCG AGC CAC CTG ACC ATC CGC CGC CAG ACT ATA GAG GAA CTG ACC         1641
Ala Pro Ser His Leu Thr Ile Arg Arg Gln Thr Ile Glu Glu Leu Thr 45                  50                  55
GGC ACG CGC TTC GAC CTG CAG CAG ATC CAC GTC AAC CTG ATC ACG CTG         1687
Gly Thr Arg Phe Asp Leu Gln Gln Ile His Val Asn Leu Ile Thr Leu 60                  65                  70
TCC GGC CAT ATT GAA GAA GAC GAC GAC GCC TTC ACG CTG AGC TGG AAG         1737
Ser Gly His Ile Glu Glu Asp Asp Asp Ala Phe Thr Leu Ser Trp Lys 75                  80                  85
CAC TGA ACGGCCTGCG CGCCCCCATA ACAAAGGAGA CACCAAT                       1780
His Stop 90
ATG GAA ACC CCG ACG CAG                                                 1798
Met Glu Thr Pro Thr Gln 1           5
```

FIG. 2G

```
AAG AAG AAG CTC GGC CTG AAG GAA CGC TAC GCC GCC ATG ACC CGC GGC      1846
Lys Lys Lys Leu Gly Leu Lys Glu Arg Tyr Ala Ala Met Thr Arg Gly
         10              15              20

CTG GGC TGG GAC ACC ACC TAC CAG CCG ATG GAC AAG GTT TTC CCC TAC      1890
Leu Gly Trp Asp Thr Thr Tyr Gln Pro Met Asp Lys Val Phe Pro Tyr
         25              30              35

GAC CGC TAT GAG GGC ATC AAG ATC CAC GAC TGG GAC AAG TGG GTC GAC      1942
Asp Arg Tyr Glu Gly Ile Lys Ile His Asp Trp Asp Lys Trp Val Asp
         40              45              50

CCG TTC CGC CTG ACC ATG GAC GCG TAC TGG AAG TAC CAG GGC GAA AAG      1990
Pro Phe Arg Leu Thr Met Asp Ala Tyr Trp Lys Tyr Gln Gly Glu Lys
55              60              65              70

GAG AAG AAG CTC TAC GCC GTG ATC GAC GCC TTC ACG CAG AAC AAC GCC      2038
Glu Lys Lys Leu Tyr Ala Val Ile Asp Ala Phe Thr Gln Asn Asn Ala
                 75              80              85

TTT CTC GGC GTG ACC GAC GCG CGC TAC ATC AAT GCG CTC AAG CTG TTC      2086
Phe Leu Gly Val Thr Asp Ala Arg Tyr Ile Asn Ala Leu Lys Leu Phe
         90              95             100
```

FIG. 2H

| | |
|---|---|
| GTG CAG GGC GTG ACG CCG CTG GAA TAC CTG GCC CAT CGC GGC TTC GCC | 2134 |
| Val Gln Gly Val Thr Pro Leu Glu Tyr Leu Ala His Arg Gly Phe Ala | |
|         105            110            115 | |
| CAC GTC GGC CGC CAC TTT ACC GGC GAG GGC GCG CGC GTG GCC TGC CAG | 2182 |
| His Val Gly Arg His Phe Thr Gly Glu Gly Ala Arg Val Ala Cys Gln | |
|         120            125            130 | |
| ATG CAG TCG ATC GAC GAG CTG CGC CAC TAC CAG ACC GAG ACC CAC GCG | 2230 |
| Met Gln Ser Ile Asp Glu Leu Arg His Tyr Gln Thr Glu Thr His Ala | |
|         135            140            145            150 | |
| CTC TCC ACC TAC AAC AAG TTC TTC AAC GGC CTG CAT CAC TCC AAC CAC | 2278 |
| Leu Ser Thr Tyr Asn Lys Phe Phe Asn Gly Leu His His Ser Asn His | |
|         155            160            165 | |
| TGG TTC GAC CGT GTC TGG TAC CTG TCG GTG CCG AAG TCC TTC TTC GAG | 2326 |
| Trp Phe Asp Arg Val Trp Tyr Leu Ser Val Pro Lys Ser Phe Phe Glu | |
|         170            175            180 | |
| GAC GCC TAC TCG GCC GGG CCG TTC GAG TTC CTG ACC GCG GTC AGC TTT | 2374 |
| Asp Ala Tyr Ser Ala Gly Pro Phe Glu Phe Leu Thr Ala Val Ser Phe | |
|         185            190            195 | |

FIG. 21

| | |
|---|---|
| TCG TTC GAG TAC GTG CTG ACC AAC CTG CTG TTC GTG CCG TTC ATG TCG | 2422 |
| Ser Phe Glu Tyr Val Leu Thr Asn Leu Leu Phe Val Pro Phe Met Ser | |
| 200                 205                 210 | |
| GGC GCC GCC TAC AAC GGC GAC ATG TCG ACC GTG ACC TTC GGC TTC TCG | 2470 |
| Gly Ala Ala Tyr Asn Gly Asp Met Ser Thr Val Thr Phe Gly Phe Ser | |
| 215                 220                 225                 230 | |
| GCT CAG TCC GAC GAA TCC CGC CAC ATG ACG CTG GGC ATC GAG TGC ATC | 2518 |
| Ala Gln Ser Asp Glu Ser Arg His Met Thr Leu Gly Ile Glu Cys Ile | |
| 235                 240                 245 | |
| AAG TTC CTC CTC GAA CAG GAT CCC GAC AAT GTG CCC ATC GTG CAG CGC | 2566 |
| Lys Phe Leu Leu Glu Gln Asp Pro Asp Asn Val Pro Ile Val Gln Arg | |
| 250                 255                 260 | |
| TGG ATC GAC AAG TGG TTC TGG CGC GGC TAC CGG CTG CTG ACG CTG GTG | 2614 |
| Trp Ile Asp Lys Trp Phe Trp Arg Gly Tyr Arg Leu Leu Thr Leu Val | |
| 265                 270                 275 | |
| GCG ATG ATG ATG GAC TAC ATG CAG CCC AAG CGC GTG ATG AGC TGG CGC | 2662 |
| Ala Met Met Met Asp Tyr Met Gln Pro Lys Arg Val Met Ser Trp Arg | |
| 280                 285                 290 | |

FIG. 2J

| | |
|---|---|
| GAG GCG TGG GAG ATG TAC GCC GAG CAG AAC GGC GGC GCG CTA TTC AAG | 2710 |
| Glu Ala Trp Glu Met Tyr Ala Glu Gln Asn Gly Gly Ala Leu Phe Lys | |
| 295                300              305             310 | |
| GAC CTG GCC CGC TAC GGC ATC CGC GAG CCC AAG GGC TGG CAG GAC GCC | 2758 |
| Asp Leu Ala Arg Tyr Gly Ile Arg Glu Pro Lys Gly Trp Gln Asp Ala | |
| 315              320              325 | |
| TGC GAA GGC AAG GAT CAC ATC AGC CAC CAG GCC TGG GCG ACC TTC TAC | 2806 |
| Cys Glu Gly Lys Asp His Ile Ser His Gln Ala Trp Ala Thr Phe Tyr | |
| 330              335              340 | |
| GGC TTC AAC GCG GCC GCC CCG TTC CAT ACC TGG GTG CCG CAG CAG GAC | 2854 |
| Gly Phe Asn Ala Ala Ala Pro Phe His Thr Trp Val Pro Gln Gln Asp | |
| 345              350              355 | |
| GAG ATG GCC TGG CTG TCC GCC AAG TAC CCG GAG ACG TTC GAC CAG CAC | 2902 |
| Glu Met Ala Trp Leu Ser Ala Lys Tyr Pro Glu Thr Phe Asp Gln His | |

FIG. 2K

```
          360                 365                 370
TAC CGT CCG CGC CTG GAG CAC TGG GAC GAG CAG GCC AAG GCC GGC AAC    2950
Tyr Arg Pro Arg Leu Glu His Trp Asp Glu Gln Ala Lys Ala Gly Asn
          375                 380                 385                 390
CGG TTC TAC ATG AAG ACG CTG CCG ATG CTG TGC CAG ACC TGC CAG ATC    2998
Arg Phe Tyr Met Lys Thr Leu Pro Met Leu Cys Gln Thr Cys Gln Ile
                    395                 400                 405
CCG ATG CTG TTC ACC GAG CCG GGC GAC CCC ACC AGG CTC TGC GCG CGC    3046
Pro Met Leu Phe Thr Glu Pro Gly Asp Pro Thr Arg Leu Cys Ala Arg
              410                 415                 420
GAA TCG AAT TAC TTC GGC AAC AAG TTC CAC TTC TGC AGT GAC CAC TGC    3094
Glu Ser Asn Tyr Phe Gly Asn Lys Phe His Phe Cys Ser Asp His Cys
                  425                 430                 435
AAG GAG ATC TTT GAC CAC GAG CCG GAG AAG TAC GTG CAA GCG TGG CTG    3142
Lys Glu Ile Phe Asp His Glu Pro Glu Lys Tyr Val Gln Ala Trp Leu
              440                 445                 450
CCC GTG CAC CAG ATC TAC CAG GGC AAC TGC TTC AAG CCG GGC GTG GAT    3190
Pro Val His Gln Ile Tyr Gln Gly Asn Cys Phe Lys Pro Gly Val Asp
          455                 460                 465                 470
```

FIG. 2L

```
CCG AGC GCC GAA GGT TTC GAT CCG CTG GCT GCC GTG CTC GAC TAC TAC   3238
Pro Ser Ala Glu Gly Phe Asp Pro Leu Ala Ala Val Leu Asp Tyr Tyr
              475             480             485
GAG GTG GAG CCC CGC GAC ACG ATG GAT TTC GAA GGC TCC GAA GAC CAG   3286
Glu Val Glu Pro Arg Asp Thr Met Asp Phe Glu Gly Ser Glu Asp Gln
              490             495             500
AAG AAC TTT GCG GCG TGG CGC GGC CAG GCC ACC AGC AAC TGA CCGGCAGGA 3337
Lys Asn Phe Ala Ala Trp Arg Gly Gln Ala Thr Ser Asn Stop
              505             510             515
GACAGCC                                                           3344

ATG ACC GTC AAT GCG                                               3359
Met Thr Val Asn Ala
 1           5
CTC AAG CCC TAC GAT TTC CCG CTG ATG GAC ACG GTG GAG AAG TTC CCC   3407
Leu Lys Pro Tyr Asp Phe Pro Leu Met Asp Thr Val Glu Lys Phe Pro
              10              15              20
GCG CCG CTG CTG TAT GTG AAC TGG GAG AAC CAC CTG ATG TTC CCG GCA   3455
Ala Pro Leu Leu Tyr Val Asn Trp Glu Asn His Leu Met Phe Pro Ala
              25              30              35
```

FIG. 2M

| | |
|---|---|
| CCG TTC TGC CTG CCG CTG CCG CCC GAG ACG CCG TTC AGC GCG CTC GCC<br>Pro Phe Cys Leu Pro Leu Pro Pro Glu Thr Pro Phe Ser Ala Leu Ala<br>              40                     45              50 | 3503 |
| GAA CAG ATC CTG CCA CCC GTC TAC GGC TAC CAC CCG GAC TTT GCC CGC<br>Glu Gln Ile Leu Pro Pro Val Tyr Gly Tyr His Pro Asp Phe Ala Arg<br>              55                     60              65 | 3551 |
| ATC GAC TGG AAG CGC GTG CAG TGG TTT CGC TCC GGC CAA CCC TGG ACA<br>Ile Asp Trp Lys Arg Val Gln Trp Phe Arg Ser Gly Gln Pro Trp Thr<br>              70                     75              80              85 | 3599 |
| CCG GAC ACG TCG AAG AGC CTC GGC GAG AAC GGG CTG GGG CAC AAG GAC<br>Pro Asp Thr Ser Lys Ser Leu Gly Glu Asn Gly Leu Gly His Lys Asp<br>              90                     95              100 | 3647 |
| CTG ATC AGT TTC CGC ACG CCG GGG CTG GAT GGC ATC GGC GGG GCA TCG<br>Leu Ile Ser Phe Arg Thr Pro Gly Leu Asp Gly Ile Gly Gly Ala Ser<br>              105                110             115 | 3695 |
| ATC TGA GCGCCCGGCC GGTGCTCCAG CAATGACAAG GTATCCATC<br>Ile Stop | 3740 |
| ATG AGC CAC CAA CTT ACC ATC GAG CCG CTC GGC GCG<br>Met Ser His Gln Leu Thr Ile Glu Pro Leu Gly Ala<br> 1              5                   10 | 3776 |

FIG. 2N

```
ACG ATC GAG GTC GAG GAA GGG CAG ACC ATT CTC GAT GCG GCG CTG CGC     3824
Thr Ile Glu Val Glu Glu Gly Gln Thr Ile Leu Asp Ala Ala Leu Arg
         15                  20                  25

CAA GGC ATC TAT ATC CCG CAT GCC TGT TGC CAC GGC CTG TGC GGG ACC     3872
Gln Gly Ile Tyr Ile Pro His Ala Cys Cys His Gly Leu Cys Gly Thr
         30                  35                  40

TGC AAG GTC TCG GTC CTC GAC GGC GAG GCC GAC CTG GGC GAG GCC AAC     3920
Cys Lys Val Ser Val Leu Asp Gly Glu Ala Asp Leu Gly Glu Ala Asn
         45              50              55              60

CCG TTC GCG TTG ATG GAT TTC GAG CGC GAG GAG GGC AAG GCG CTG GCG     3968
Pro Phe Ala Leu Met Asp Phe Glu Arg Glu Glu Gly Lys Ala Leu Ala
                 65              70              75

TGC TGC GCG ACG CTG CAG GCC GAT ACC ACC ATC GAG GCC GAT GTC GAC     4016
Cys Cys Ala Thr Leu Gln Ala Asp Thr Thr Ile Glu Ala Asp Val Asp
         80              85              90

AAG GAC CCG GAC GGC GAG ATT ATC CCG GTG CGG GAT TTC GAG GCC GAC     4064
Lys Asp Pro Asp Gly Glu Ile Ile Pro Val Arg Asp Phe Glu Ala Asp
         95                  100                 105
```

FIG. 20

```
GTG ATG TGC ATC GAC CAG CTC ACC CCG ACC ATC AAG GCG ATC CGC CTG    4112
Val Met Cys Ile Asp Gln Leu Thr Pro Thr Ile Lys Ala Ile Arg Leu
    110             115             120

CGC CTC GCG GAG CCG ATG CGT TTC CAG GCG GGC CAG TAC GTC CAG TTC    4160
Arg Leu Ala Glu Pro Met Arg Phe Gln Ala Gly Gln Tyr Val Gln Phe
125             130             135             140

GAG ATC CCG GGC CTG GGC CAG ACC CGC GCT TTC TCG ATC GCC AAC GCG    4208
Glu Ile Pro Gly Leu Gly Gln Thr Arg Ala Phe Ser Ile Ala Asn Ala
            145             150             155

CCG GCG GAC GTC GCC GCG ACC GGC GAG ATC GAG CTG AAC GTG CGG CAG    4256
Pro Ala Asp Val Ala Ala Thr Gly Glu Ile Glu Leu Asn Val Arg Gln
        160             165             170

GTG CCG GGC GGC CTT GGC ACC GGC TAC CTG CAC GAG CAG CTC GCC GCC    4304
Val Pro Gly Gly Leu Gly Thr Gly Tyr Leu His Glu Gln Leu Ala Ala
    175             180             185

GGG GAT CGC GTG CGC TTG TCC GGA CCC TAT GGC CGC TTC TTC GTG CGC    4352
Gly Asp Arg Val Arg Leu Ser Gly Pro Tyr Gly Arg Phe Phe Val Arg
190             195             200
```

FIG. 2P

| | |
|---|---|
| CGC TCG GCC GGC CTG CCG ATG ATC TTC ATG GCG GGC GGC TCG GGG CTG | 4400 |
| Arg Ser Ala Gly Leu Pro Met Ile Phe Met Ala Gly Gly Ser Gly Leu | |
| 205                210                215                220 | |
| TCG AGC CCG CGC TCC ATG ATC TGC GAC CTG CTG GAA GGC GGC GTC ACC | 4448 |
| Ser Ser Pro Arg Ser Met Ile Cys Asp Leu Leu Glu Gly Gly Val Thr | |
| 225                230              235 | |
| GCG CCG ATT ACG CTG GTC TAC GGC CAG CGC AAC GCG AAG GAG CTG TAC | 4496 |
| Ala Pro Ile Thr Leu Val Tyr Gly Gln Arg Asn Ala Lys Glu Leu Tyr | |
| 240                245              250 | |
| TAC CAC GAC GAG TTC CGC GCG CTG AGC GAG CGC TAT CCC AAC TTC ACC | 4544 |
| Tyr His Asp Glu Phe Arg Ala Leu Ser Glu Arg Tyr Pro Asn Phe Thr | |
| 255                260              265 | |
| TAC GTG CCG GCG CTG TCG GAG GGG GCG GGG GAC GGC GAG GTC GCG CAG | 4592 |
| Tyr Val Pro Ala Leu Ser Glu Gly Ala Gly Asp Gly Glu Val Ala Gln | |
| 270                275              280 | |
| GGC TTC GTC CAC GAC GTC GCC AAG GCG CAC TTC GAC AAT GAC TTC TCG | 4640 |
| Gly Phe Val His Asp Val Ala Lys Ala His Phe Asp Asn Asp Phe Ser | |
| 285                290              295              300 | |

FIG. 2Q

| | | |
|---|---|---|
| GGC CAC CAG GCT TAC CTG TGC GGA CCG CCC GCG ATG ATC GAC GCC TGC | | 4688 |
| Gly His Gln Ala Tyr Leu Cys Gly Pro Pro Ala Met Ile Asp Ala Cys | | |
| 305 310 315 | | |
| ATC ACG GCG CTG ATG CAG GGC CGG CTG TTC GAG CGC GAC ATC TAC CAC | | 4732 |
| Ile Thr Ala Leu Met Gln Gly Arg Leu Phe Glu Arg Asp Ile Tyr His | | |
| 320 325 330 | | |
| GAG AAG TTC ATT TCG GCG GCG GAT GCG CAG CAG ACC CGC AGC CCG CTG | | 4784 |
| Glu Lys Phe Ile Ser Ala Ala Asp Ala Gln Gln Thr Arg Ser Pro Leu | | |
| 335 340 345 | | |
| TTT CGC AAG GTG TGA C | | 4800 |
| Phe Arg Lys Val Stop | | |
| 350 | | |
| GTG | | 4803 |
| Met | | |
| 1 | | |
| GAC ACG TGC ATC AAG GCC ACG GTG CGG GTC GCG CAG ACG GGT GAG TCC | | 4851 |
| Asp Thr Cys Ile Lys Ala Thr Val Arg Val Ala Gln Thr Gly Glu Ser | | |
| 5 10 15 | | |

FIG. 2R

| | |
|---|---|
| TTC TCG TGC ACC GCC GGC GAA TCG CTG CTC GCC GGC ATG GCA AAG CTG | 4899 |
| Phe Ser Cys Thr Ala Gly Glu Ser Leu Leu Ala Gly Met Ala Lys Leu | |
|       20           25          30 | |
| GGC CGG CGC GGC ATT CCG GTC GGC TGC CTG AAC GGC GGC TGC GGG GTC | 4947 |
| Gly Arg Arg Gly Ile Pro Val Gly Cys Leu Asn Gly Gly Cys Gly Val | |
|       35           40          45 | |
| TGC AAG GTG CGG GTG CTG AGC GGC GAC GTG CGC AAG CTG GGC CCG GTC | 4995 |
| Cys Lys Val Arg Val Leu Ser Gly Asp Val Arg Lys Leu Gly Pro Val | |
| 50          55           60          65 | |
| AGC CGC GCG CAT GTC AGC GCT GAC GAA GAG GGG CTG GGC TAC ACG CTG | 5043 |
| Ser Arg Ala His Val Ser Ala Asp Glu Glu Gly Leu Gly Tyr Thr Leu | |
|       70           75          80 | |
| GCC TGC CGC GTG GCG CCG CAG GGC GAC GTC GAG CTG GAG GTG GCC GGG | 5091 |
| Ala Cys Arg Val Ala Pro Gln Gly Asp Val Glu Leu Glu Val Ala Gly | |
|       85           90          95 | |

FIG. 2S

```
AAG ATG CAG AAG CCG TTC CTC TGC TGC GCC CAG GCC AGG AAG TAA AGGCA    5141
Lys Met Gln Lys Pro Phe Leu Cys Cys Ala Gln Ala Arg Lys Stop
        100                 105                 110
GCAAGAAAAC ATCAACAGGA GACACATCAT GGGTGTGATG CGGATAGGCC ATGCCAACCT    5201
GAAGGTCATG GACATGGAAG CGGCCCTGCG CCACTACGTG CGGGTGCTGG GCATGAAGGA    5261
AGTGATGCGC GACGCGGACG GTAACGTCTA TTTGAAATGC TGGGACGAGT GGGACAAGTA    5321
CTCGCTGATC                                                          5331
```

FIG. 3

Met Thr Leu Gln Thr Pro Ala Asn Gln Ala Ser Asp Pro Cys Arg Lys
1               5                   10                  15

Phe Val Arg Val Thr Gly Leu Asn Pro Arg Gly Phe Val Glu Phe Glu
                20                  25                  30

Phe Ala Ile Gly Gly Pro Glu Met Phe Val Glu Leu Thr Leu Pro Ile
                35                  40                  45

Asp Ala Phe Asp Ala Phe Cys Thr Thr Gln Asn Val Val Arg Leu Asp
50                  55                  60

Asp Ser Gly Ser Asp Phe His Arg Asp Pro Thr Thr Leu Arg Ser Asn
65                  70                  75                  80

Pro

FIG. 4

| FIG. 4A |
| FIG. 4B |
| FIG. 4C |

FIG. 4A

Met Thr Ile Glu Leu Lys Thr Val Asp Ile Lys Pro Leu Arg Gln Thr
1               5                   10                  15

Tyr Ala His Val Ala Arg His Ile Gly Gly Asp Lys Thr Ala Ser Arg
                20                  25                  30

Tyr Gln Glu Gly Met Met Gly Ala Gln Pro Glu Thr Asn Phe His Tyr
                35                  40                  45

Arg Pro Thr Trp Asp Pro Ala His Gln Ile Phe Asp Ala Ser Arg Ser
                50                  55                  60

Ala Ile Arg Met Ala Ser Trp Tyr Val Leu Lys Asp Pro Arg Gln Tyr
65                  70                  75                  80

Tyr Tyr Ala Ser Trp Thr Thr Ala Arg Ala Arg Gln Gln Asp Thr Met
                85                  90                  95

FIG. 4B

Glu Ser Asn Phe Glu Phe Val Glu Ser Arg Arg Met Ile Asp Arg Met
          100              105            110

Pro Ala Glu Val Ala Lys His Ala Leu Asp Leu Leu Val Pro Leu Arg
     115           120            125

His Ala Ala Trp Gly Ala Asn Met Asn Asn Ala Gln Val Cys Ala Leu
     130           135            140

Gly Tyr Gly Thr Ala Phe Thr Ala Ala Ala Met Phe His Ala Met Asp
145            150            155           160

Asn Leu Gly Val Ala Gln Tyr Leu Thr Arg Leu Ala Leu Ala Val Ala
          165            170           175

Gly Pro Glu Val Leu Asp Ala Gly Arg His Ala Trp Leu Glu His Pro
     180           185            190

Ala Trp Gln Pro Leu Arg His Tyr Ile Glu Asp Thr Phe Val Val Asp
     195           200            205

FIG. 4C

Asp Pro Val Glu Leu Phe Val Ala Gln Asn Leu Ala Leu Asp Gly Met
         210                 215                 220

Leu Tyr Pro Leu Val Tyr Asp Arg Phe Val Asp Glu Arg Ile Ala Leu
225                 230                 235                 240

Gly Gly Gly Ser Ala Ile Ala Met Leu Thr Ala Phe Met Pro Glu Trp
                 245                 250                 255

His Glu Glu Ser Lys Arg Trp Val Asp Ala Val Val Lys Thr Met Ala
                 260                 265                 270

Ala Glu Ser Glu Glu Asn Lys Ala Leu Leu Ala His Trp Thr Arg Asp
                 275                 280                 285

Trp Ala Gly Arg Ala Phe Ala Ala Leu Gln Pro Val Ala Glu Leu Ala
                 290                 295                 300

Phe Pro Thr His Ala Pro Glu Val Leu Asp Ala Val Arg Glu Gln Phe
305                 310                 315                 320

Gln Thr Arg Ile Ser Lys Leu Gly Ile Ala Leu
                 325                 330

FIG. 5

Met Ser Asn Val Phe Ile Ala Phe Gln Ala Asn Glu Glu Ser Arg Pro
1               5                   10                  15

Val Val Glu Ala Ile Leu Ala Asp Asn Pro Asp Ala Val Leu Val Glu
            20                  25                  30

Ser Pro Gly Met Val Lys Ile Asp Ala Pro Ser His Leu Thr Ile Arg
            35                  40                  45

Arg Gln Thr Ile Glu Glu Leu Thr Gly Thr Arg Phe Asp Leu Gln Gln
        50                  55                  60

Ile His Val Asn Leu Ile Thr Leu Ser Gly His Ile Glu Glu Asp Asp
65                  70                  75                  80

Asp Ala Phe Thr Leu Ser Trp Lys His
                85

Met Glu Thr Pro Thr Gln Lys Lys Lys Leu Gly Leu Lys Glu Arg Tyr
1           5                    10                   15

Ala Ala Met Thr Arg Gly Leu Gly Trp Asp Thr Thr Tyr Gln Pro Met
            20                   25                   30

Asp Lys Val Phe Pro Tyr Asp Arg Tyr Glu Gly Ile Lys Ile His Asp
            35                   40                   45

Trp Asp Lys Trp Val Asp Pro Phe Arg Leu Thr Met Asp Ala Tyr Trp
            50                   55                   60

Lys Tyr Gln Gly Glu Lys Glu Lys Lys Leu Tyr Ala Val Ile Asp Ala
            65                   70                   75                   80

Phe Thr Gln Asn Asn Ala Phe Leu Gly Val Thr Asp Ala Arg Tyr Ile
                 85                   90                   95

FIG. 6B

Asn Ala Leu Lys Leu Phe Val Gln Gly Val Thr Pro Leu Glu Tyr Leu
                    100                 105                 110

Ala His Arg Gly Phe Ala His Val Gly Arg His Phe Thr Gly Glu Gly
            115                 120                 125

Ala Arg Val Ala Cys Gln Met Gln Ser Ile Asp Glu Leu Arg His Tyr
            130                 135                 140

Gln Thr Glu Thr His Ala Leu Ser Thr Tyr Asn Lys Phe Phe Asn Gly
145                 150                 155                 160

Leu His His Ser Asn His Trp Phe Asp Arg Val Trp Tyr Leu Ser Val
                    165                 170                 175

Pro Lys Ser Phe Phe Glu Asp Ala Tyr Ser Ala Gly Pro Phe Glu Phe
                    180                 185                 190

Leu Thr Ala Val Ser Phe Ser Phe Glu Tyr Val Leu Thr Asn Leu Leu
                    195                 200                 205

Phe Val Pro Phe Met Ser Gly Ala Ala Tyr Asn Gly Asp Met Ser Thr
                    210                 215                 220

Val Thr Phe Gly Phe Ser Ala Gln Ser Asp Glu Ser Arg His Met Thr
225                 230                 235                 240

FIG. 6C

Leu Gly Ile Glu Cys Ile Lys Phe Leu Leu Glu Gln Asp Pro Asp Asn
                245                 250                 255

Val Pro Ile Val Gln Arg Trp Ile Asp Lys Trp Phe Trp Arg Gly Tyr
            260                 265                 270

Arg Leu Leu Thr Leu Val Ala Met Met Met Asp Tyr Met Gln Pro Lys
            275                 280                 285

Arg Val Met Ser Trp Arg Glu Ala Trp Glu Met Tyr Ala Glu Gln Asn
            290                 295                 300

Gly Gly Ala Leu Phe Lys Asp Leu Ala Arg Tyr Gly Ile Arg Glu Pro
305                 310                 315                 320

Lys Gly Trp Gln Asp Ala Cys Glu Gly Lys Asp His Ile Ser His Gln
            325                 330                 335

Ala Trp Ala Thr Phe Tyr Gly Phe Asn Ala Ala Ala Pro Phe His Thr
            340                 345                 350

Trp Val Pro Gln Gln Asp Glu Met Ala Trp Leu Ser Ala Lys Tyr Pro
            355                 360                 365

Glu Thr Phe Asp Gln His Tyr Arg Pro Arg Leu Glu His Trp Asp Glu
            370                 375                 380

FIG. 6D

Gln Ala Lys Ala Gly Asn Arg Phe Tyr Met Lys Thr Leu Pro Met Leu
385                 390                 395                 400

Cys Gln Thr Cys Gln Ile Pro Met Leu Phe Thr Glu Pro Gly Asp Pro
            405                 410                 415

Thr Arg Leu Cys Ala Arg Glu Ser Asn Tyr Phe Gly Asn Lys Phe His
            420                 425                 430

Phe Cys Ser Asp His Cys Lys Glu Ile Phe Asp His Glu Pro Glu Lys
            435                 440                 445

Tyr Val Gln Ala Trp Leu Pro Val His Gln Ile Tyr Gln Gly Asn Cys
450                 455                 460

Phe Lys Pro Gly Val Asp Pro Ser Ala Glu Gly Phe Asp Pro Leu Ala
465                 470                 475                 480

Ala Val Leu Asp Tyr Tyr Glu Val Glu Pro Arg Asp Thr Met Asp Phe
            485                 490                 495

Glu Gly Ser Glu Asp Gln Lys Asn Phe Ala Ala Trp Arg Gly Gln Ala
            500                 505                 510

Thr Ser Asn
515

FIG. 7

Met Thr Val Asn Ala Leu Lys Pro Tyr Asp Phe Pro Leu Met Asp Thr
1           5                    10                   15

Val Glu Lys Phe Pro Ala Pro Leu Leu Tyr Val Asn Trp Glu Asn His
             20                   25                  30

Leu Met Phe Pro Ala Pro Phe Cys Leu Pro Leu Pro Pro Glu Thr Pro
             35                   40                  45

Phe Ser Ala Leu Ala Glu Gln Ile Leu Pro Pro Val Tyr Gly Tyr His
             50                   55                  60

Pro Asp Phe Ala Arg Ile Asp Trp Lys Arg Val Gln Trp Phe Arg Ser
65                   70                   75                  80

Gly Gln Pro Trp Thr Pro Asp Thr Ser Lys Ser Leu Gly Glu Asn Gly
             85                   90                  95

Leu Gly His Lys Asp Leu Ile Ser Phe Arg Thr Pro Gly Leu Asp Gly
             100                  105                 110

Ile Gly Gly Ala Ser Ile
      115

Met Ser His Gln Leu Thr Ile Glu Pro Leu Gly Ala Thr Ile Glu Val
1               5                   10                  15

Glu Glu Gly Gln Thr Ile Leu Asp Ala Ala Leu Arg Gln Gly Ile Tyr
                20                  25                  30

Ile Pro His Ala Cys Cys His Gly Leu Cys Gly Thr Cys Lys Val Ser
                35                  40                  45

Val Leu Asp Gly Glu Ala Asp Leu Gly Glu Ala Asn Pro Phe Ala Leu
        50                  55                  60

Met Asp Phe Glu Arg Glu Glu Gly Lys Ala Leu Ala Cys Cys Ala Thr
65                  70                  75                  80

Leu Gln Ala Asp Thr Thr Ile Glu Ala Asp Val Asp Lys Asp Pro Asp
                85                  90                  95

FIG. 8B

Gly Glu Ile Ile Pro Val Arg Asp Phe Glu Ala Asp Val Met Cys Ile
            100                 105                 110
Asp Gln Leu Thr Pro Thr Ile Lys Ala Ile Arg Leu Arg Leu Ala Glu
            115                 120                 125
Pro Met Arg Phe Gln Ala Gly Gln Tyr Val Gln Phe Glu Ile Pro Gly
            130                 135                 140
Leu Gly Gln Thr Arg Ala Phe Ser Ile Ala Asn Ala Pro Ala Asp Val
            145                 150                 155                 160
Ala Ala Thr Gly Glu Ile Glu Leu Asn Val Arg Gln Val Pro Gly Gly
                        165                 170                 175
Leu Gly Thr Gly Tyr Leu His Glu Gln Leu Ala Ala Gly Asp Arg Val
            180                 185                 190
Arg Leu Ser Gly Pro Tyr Gly Arg Phe Phe Val Arg Arg Ser Ala Gly
            195                 200                 205
Leu Pro Met Ile Phe Met Ala Gly Gly Ser Gly Leu Ser Ser Pro Arg
            210                 215                 220
Ser Met Ile Cys Asp Leu Leu Glu Gly Gly Val Thr Ala Pro Ile Thr
            225                 230                 235                 240

FIG. 8C

Leu Val Tyr Gly Gln Arg Asn Ala Lys Glu Leu Tyr Tyr His Asp Glu
              245                 250                 255

Phe Arg Ala Leu Ser Glu Arg Tyr Pro Asn Phe Thr Tyr Val Pro Ala
              260                 265                 270

Leu Ser Glu Gly Ala Gly Asp Gly Glu Val Ala Gln Gly Phe Val His
              275                 280                 285

Asp Val Ala Lys Ala His Phe Asp Asn Asp Phe Ser Gly His Gln Ala
              290                 295                 300

Tyr Leu Cys Gly Pro Pro Ala Met Ile Asp Ala Cys Ile Thr Ala Leu
305                 310                 315                 320

Met Gln Gly Arg Leu Phe Glu Arg Asp Ile Tyr His Glu Lys Phe Ile
              325                 330                 335

Ser Ala Ala Asp Ala Gln Gln Thr Arg Ser Pro Leu Phe Arg Lys Val
              340                 345                 350

FIG. 9

Met Asp Thr Cys Ile Lys Ala Thr Val Arg Val Ala Gln Thr Gly Glu
1 5 10 15

Ser Phe Ser Cys Thr Ala Gly Glu Ser Leu Leu Ala Gly Met Ala Lys
20 25 30

Leu Gly Arg Arg Gly Ile Pro Val Gly Cys Leu Asn Gly Gly Cys Gly
35 40 45

Val Cys Lys Val Arg Val Leu Ser Gly Asp Val Arg Lys Leu Gly Pro
50 55 60

Val Ser Arg Ala His Val Ser Ala Asp Glu Glu Gly Leu Gly Tyr Thr
65 70 75 80

Leu Ala Cys Arg Val Ala Pro Gln Gly Asp Val Glu Leu Glu Val Ala
85 90 95

Gly Lys Met Gln Lys Pro Phe Leu Cys Cys Ala Gln Ala Arg Lys
100 105 110

FIG. 10

ATCGACCCAT TGACCATGGC CCTGCAGACC CCAG 34

FIG. 11

CTCAGGAGCA ACCCATGGCA ATCGAGCTGA AAAC 34

FIG. 12

TACTTCCAGT ACGCGTCGAT GGTCAGGCGG AACG 34

FIG. 13

GCCCAGCTTT GCCATGGCGG CGAGCAGCGA TTCG 34

FIG. 14

CAATGAAAGGGGATCCGAGGCGACATCGAC

FIG. 15

ATGTCGACGGGATCCAGCTCGATTGTCACG

SEQUENCE LISTING

```
<160> NUMBER OF SEQ ID NOS: 14

<210> SEQ ID NO 1
<211> LENGTH: 5331
<212> TYPE: DNA
<213> ORGANISM: Ralstonia eutropha
<220> FEATURE:
<221> NAME/KEY: CDS
<222> LOCATION: (200)..(445)
<223> OTHER INFORMATION: tomK
<220> FEATURE:
<221> NAME/KEY: CDS
<222> LOCATION: (446)...(1437)
<223> OTHER INFORMATION: tomL
<220> FEATURE:
<221> NAME/KEY: CDS
<222> LOCATION: (1470)...(1739)
<223> OTHER INFORMATION: tomM
<220> FEATURE:
<221> NAME/KEY: CDS
<222> LOCATION: (1777)...(3324)
<223> OTHER INFORMATION: tomN
<220> FEATURE:
<221> NAME/KEY: CDS
<222> LOCATION: (3341)...(3697)
<223> OTHER INFORMATION: tomO
<220> FEATURE:
<221> NAME/KEY: CDS
<222> LOCATION: (3737)...(4795)
```

<223> OTHER INFORMATION: tomP
<220> FEATURE:
<221> NAME/KEY: CDS
<222> LOCATION: (4797)...(5132)
<223> OTHER INFORMATION: tomQ

<400> SEQUENCE: 1

| | | |
|---|---|---:|
| gatcaacgat tgaagcgtc cgcataagag cggtaccaag tccgggagcg tgctgggtaa | | 60 |
| ccaagcattt tgcaggcgcg caagccaact tcgactcagt attttccctg aaatatcgag | | 120 |
| atttccggc catgggctgg caccgctggc acgcccgctg caatgaaagg ggcacggagg | | 180 |
| cgacatcgac ccattgact atg acc ctg cag acc cca gcc aac caa gca tcc<br>                                  Met Thr Leu Gln Thr Pro Ala Asn Gln Ala Ser<br>                                     1               5                    10 | | 232 |
| gat ccc tgc cgc aag ttc gtc cgg gtc acc ggc ctc aac ccg cgc gga<br>Asp Pro Cys Arg Lys Phe Val Arg Val Thr Gly Leu Asn Pro Arg Gly<br>               15                    20                    25 | | 280 |
| ttc gtc gaa ttc gag ttc gcg atc ggc ggg ccg gag atg ttc gtc gaa<br>Phe Val Glu Phe Glu Phe Ala Ile Gly Gly Pro Glu Met Phe Val Glu<br>         30                         35                      40 | | 328 |
| ctg acc ctg ccc ata gac gca ttc gac gcg ttc tgc acc acg cag aac<br>Leu Thr Leu Pro Ile Asp Ala Phe Asp Ala Phe Cys Thr Thr Gln Asn<br>     45                        50                      55 | | 376 |
| gtc gtc cgg ctg gat gac tcc ggc agc gac ttc cac cgc gac ccc acg<br>Val Val Arg Leu Asp Asp Ser Gly Ser Asp Phe His Arg Asp Pro Thr<br>60                    65                    70                    75 | | 424 |
| acc ctc agg agc aac ccg tga<br>Thr Leu Arg Ser Asn Pro<br>             80 | | 445 |
| gtg aca atc gag ctg aaa acc gtc gac atc<br>Met Thr Ile Glu Leu Lys Thr Val Asp Ile<br>                85                    90 | | 475 |
| aag ccg cta cgg cag acc tac gcg cat gtg gcg cgg cat atc ggt ggc<br>Lys Pro Leu Arg Gln Thr Tyr Ala His Val Ala Arg His Ile Gly Gly<br>             95                      100                 105 | | 523 |
| gac aag acg gcc tcg cgc tac cag gaa ggc atg atg ggc gcg cag ccc<br>Asp Lys Thr Ala Ser Arg Tyr Gln Glu Gly Met Met Gly Ala Gln Pro<br>         110                      115                 120 | | 571 |
| gag acc aac ttc cac tat cgc cca acc tgg gat ccg gcg cac caa atc<br>Glu Thr Asn Phe His Tyr Arg Pro Thr Trp Asp Pro Ala His Gln Ile<br>125                   130                  135 | | 619 |
| ttc gac gcc tcg cgc tcg gcg atc cgc atg gcg agc tgg tac gtg ctg<br>Phe Asp Ala Ser Arg Ser Ala Ile Arg Met Ala Ser Trp Tyr Val Leu<br>140                   145                  150                 155 | | 667 |
| aag gac ccg cgc cag tac tac tac gcc tcg tgg acc acg gcc cgc gcg<br>Lys Asp Pro Arg Gln Tyr Tyr Tyr Ala Ser Trp Thr Thr Ala Arg Ala<br>                 160                  165                 170 | | 715 |
| cgc cag cag gac acg atg gaa tcg aac ttc gag ttc gtc gaa tcg cgc<br>Arg Gln Gln Asp Thr Met Glu Ser Asn Phe Glu Phe Val Glu Ser Arg<br>         175                      180                 185 | | 763 |
| cgg atg atc gac cgg atg ccg gcg gag gtg gcc aaa cac gcg ctc gac<br>Arg Met Ile Asp Arg Met Pro Ala Glu Val Ala Lys His Ala Leu Asp<br>             190                    195                 200 | | 811 |
| ctt ctg gta ccg ctg cgc cac gcc gca tgg ggc gcg aac atg aac aac<br>Leu Leu Val Pro Leu Arg His Ala Ala Trp Gly Ala Asn Met Asn Asn<br>205                   210                  215 | | 859 |
| gcg cag gtc tgc gca ctg ggt tac ggc acc gcc ttc acc gcg gcg gcg<br>Ala Gln Val Cys Ala Leu Gly Tyr Gly Thr Ala Phe Thr Ala Ala Ala<br>220                    225                  230                 235 | | 907 |
| atg ttc cac gcg atg gac aac ctc ggc gtt gcg caa tac ctg acg cgc | | 955 |

```
                                           -continued

Met Phe His Ala Met Asp Asn Leu Gly Val Ala Gln Tyr Leu Thr Arg
            240                 245                 250 ctg gcg ctc gca gtg gcc ggc ccg gag gtg ctc gac gcg ggc cgg cac    1003
Leu Ala Leu Ala Val Ala Gly Pro Glu Val Leu Asp Ala Gly Arg His
                255                 260                 265 gcc tgg ctc gaa cat ccg gcg tgg cag ccg ctg cgc cac tac atc gag    1051
Ala Trp Leu Glu His Pro Ala Trp Gln Pro Leu Arg His Tyr Ile Glu
            270                 275                 280 gac acc ttc gtc gtc gac gac ccg gtc gaa ctg ttc gtc gcc cag aac    1099
Asp Thr Phe Val Val Asp Asp Pro Val Glu Leu Phe Val Ala Gln Asn
        285                 290                 295 ctg gcg ctt gac ggc atg ctt tac ccg ctg gtc tac gac cgc ttt gtc    1147
Leu Ala Leu Asp Gly Met Leu Tyr Pro Leu Val Tyr Asp Arg Phe Val
300                 305                 310                 315 gac gaa cgg atc gcc ctg ggc ggc ggc tcc gcg atc gcg atg ctg acg    1195
Asp Glu Arg Ile Ala Leu Gly Gly Gly Ser Ala Ile Ala Met Leu Thr
                320                 325                 330 gcc ttc atg ccc gag tgg cac gag gag tcg aaa cgc tgg gtc gat gcc    1243
Ala Phe Met Pro Glu Trp His Glu Glu Ser Lys Arg Trp Val Asp Ala
            335                 340                 345 gtg gtg aag acg atg gcg gcc gag tcc gaa gag aac aag gcg ctg ctg    1291
Val Val Lys Thr Met Ala Ala Glu Ser Glu Glu Asn Lys Ala Leu Leu
        350                 355                 360 gcg cac tgg acc cgc gac tgg gcc ggg cgt gcg ttt gcc gcg ctg cag    1339
Ala His Trp Thr Arg Asp Trp Ala Gly Arg Ala Phe Ala Ala Leu Gln
365                 370                 375 ccg gtc gca gag ctg gcc ttc ccg acc cat gcg ccc gaa gtg ctc gac    1387
Pro Val Ala Glu Leu Ala Phe Pro Thr His Ala Pro Glu Val Leu Asp
380                 385                 390                 395 gcg gtg cgc gag cag ttc cag acc cgg att tcg aaa ctc ggc atc gcg    1435
Ala Val Arg Glu Gln Phe Gln Thr Arg Ile Ser Lys Leu Gly Ile Ala
                400                 405                 410 ctc tga tcccgcccct cactcgctct gaaggaaaac ac                        1473
Leu atg tcc aac gta ttc atc gcc ttc                                    1497
Met Ser Asn Val Phe Ile Ala Phe
            415                 420 cag gcc aac gag gag tcc cgt ccg gtg gtc gag gcc atc ctc gcc gac    1545
Gln Ala Asn Glu Glu Ser Arg Pro Val Val Glu Ala Ile Leu Ala Asp
                425                 430                 435 aac ccg gac gcg gtg ctg gtc gag tcc ccg gga atg gtc aag atc gac    1593
Asn Pro Asp Ala Val Leu Val Glu Ser Pro Gly Met Val Lys Ile Asp
            440                 445                 450 gcg ccg agc cac ctg acc atc cgc cgc cag act ata gag gaa ctg acc    1641
Ala Pro Ser His Leu Thr Ile Arg Arg Gln Thr Ile Glu Glu Leu Thr
        455                 460                 465 ggc acg cgc ttc gac ctg cag cag atc cac gtc aac ctg atc acg ctg    1689
Gly Thr Arg Phe Asp Leu Gln Gln Ile His Val Asn Leu Ile Thr Leu
470                 475                 480 tcc ggc cat att gaa gaa gac gac gac gcc ttc acg ctg agc tgg aag    1737
Ser Gly His Ile Glu Glu Asp Asp Asp Ala Phe Thr Leu Ser Trp Lys
485                 490                 495                 500 cac tga acggcctgcg cgcccccata acaaggaga caccaat                    1780
His atg gaa acc ccg acg cag                                            1798
Met Glu Thr Pro Thr Gln
            505 aag aag aag ctc ggc ctg aag gaa cgc tac gcc gcc atg acc cgc ggc    1846
Lys Lys Lys Leu Gly Leu Lys Glu Arg Tyr Ala Ala Met Thr Arg Gly
```

-continued

```
              510                 515                 520
ctg ggc tgg gac acc acc tac cag ccg atg gac aag gtt ttc ccc tac    1894
Leu Gly Trp Asp Thr Thr Tyr Gln Pro Met Asp Lys Val Phe Pro Tyr
    525                 530                 535 gac cgc tat gag ggc atc aag atc cac gac tgg gac aag tgg gtc gac    1942
Asp Arg Tyr Glu Gly Ile Lys Ile His Asp Trp Asp Lys Trp Val Asp
540                 545                 550                 555 ccg ttc cgc ctg acc atg gac gcg tac tgg aag tac cag ggc gaa aag    1990
Pro Phe Arg Leu Thr Met Asp Ala Tyr Trp Lys Tyr Gln Gly Glu Lys
                560                 565                 570 gag aag aag ctc tac gcc gtg atc gac gcc ttc acg cag aac aac gcc    2038
Glu Lys Lys Leu Tyr Ala Val Ile Asp Ala Phe Thr Gln Asn Asn Ala
            575                 580                 585 ttt ctc ggc gtg acc gac gcg cgc tac atc aat gcg ctc sag ctg ttc    2086
Phe Leu Gly Val Thr Asp Ala Arg Tyr Ile Asn Ala Leu Lys Leu Phe
        590                 595                 600 gtg cag ggc gtg acg ccg ctg gaa tac ctg gcc cat cgc ggc ttc gcc    2134
Val Gln Gly Val Thr Pro Leu Glu Tyr Leu Ala His Arg Gly Phe Ala
    605                 610                 615 cac gtc ggc cgc cac ttt acc ggc gag ggc gcg cgc gtg gcc tgc cag    2182
His Val Gly Arg His Phe Thr Gly Glu Gly Ala Arg Val Ala Cys Gln
620                 625                 630                 635 atg cag tcg atc gac gag ctg cgc cac tac cag acc gag acc cac gcg    2230
Met Gln Ser Ile Asp Glu Leu Arg His Tyr Gln Thr Glu Thr His Ala
                640                 645                 650 ctc tcc acc tac aac aag ttc ttc aac ggc ctg cat cac tcc aac cac    2278
Leu Ser Thr Tyr Asn Lys Phe Phe Asn Gly Leu His His Ser Asn His
            655                 660                 665 tgg ttc gac cgt gtc tgg tac ctg tcg gtg ccg aag tcc ttc ttc gag    2326
Trp Phe Asp Arg Val Trp Tyr Leu Ser Val Pro Lys Ser Phe Phe Glu
        670                 675                 680 gac gcc tac tcg gcc ggg ccg ttc gag ttc ctg acc gcg gtc agc ttt    2374
Asp Ala Tyr Ser Ala Gly Pro Phe Glu Phe Leu Thr Ala Val Ser Phe
    685                 690                 695 tcg ttc gag tac gtg ctg acc aac ctg ctg ttc gtg ccg ttc atg tcg    2422
Ser Phe Glu Tyr Val Leu Thr Asn Leu Leu Phe Val Pro Phe Met Ser
700                 705                 710                 715 ggc gcc gcc tac aac ggc gac atg tcg acc gtg acc ttc ggc ttc tcg    2470
Gly Ala Ala Tyr Asn Gly Asp Met Ser Thr Val Thr Phe Gly Phe Ser
                720                 725                 730 gct cag tcc gac gaa tcc cgc cac atg acg ctg ggc atc gag tgc atc    2518
Ala Gln Ser Asp Glu Ser Arg His Met Thr Leu Gly Ile Glu Cys Ile
            735                 740                 745 aag ttc ctc ctc gaa cag gat ccc gac aat gtg ccc atc gtg cag cgc    2566
Lys Phe Leu Leu Glu Gln Asp Pro Asp Asn Val Pro Ile Val Gln Arg
        750                 755                 760 tgg atc gac aag tgg ttc tgg cgc ggc tac cgg ctg ctg acg ctg gtg    2614
Trp Ile Asp Lys Trp Phe Trp Arg Gly Tyr Arg Leu Leu Thr Leu Val
    765                 770                 775 gcg atg atg atg gac tac atg cag ccc aag cgc gtg atg agc tgg cgc    2662
Ala Met Met Met Asp Tyr Met Gln Pro Lys Arg Val Met Ser Trp Arg
780                 785                 790                 795 gag gcg tgg gag atg tac gcc gag cag aac ggc ggc gcg cta ttc aag    2710
Glu Ala Trp Glu Met Tyr Ala Glu Gln Asn Gly Gly Ala Leu Phe Lys
                800                 805                 810 gac ctg gcc cgc tac ggc atc cgc gag ccc aag ggc tgg cag gac gcc    2758
Asp Leu Ala Arg Tyr Gly Ile Arg Glu Pro Lys Gly Trp Gln Asp Ala
            815                 820                 825 tgc gaa ggc aag gat cac atc agc cac cag gcc tgg gcg acc ttc tac    2806
```

```
                                                     -continued

Cys Glu Gly Lys Asp His Ile Ser His Gln Ala Trp Ala Thr Phe Tyr
        830                 835                 840 ggc ttc aac gcg gcc gcc ccg ttc cat acc tgg gtg ccg cag cag gac        2854
Gly Phe Asn Ala Ala Ala Pro Phe His Thr Trp Val Pro Gln Gln Asp
845                 850                 855 gag atg gcc tgg ctg tcc gcc aag tac ccg gag acg ttc gac cag cac        2902
Glu Met Ala Trp Leu Ser Ala Lys Tyr Pro Glu Thr Phe Asp Gln His
860                 865                 870                 875 tac cgt ccg cgc ctg gag cac tgg gac gag cag gcc aag gcc ggc aac        2950
Tyr Arg Pro Arg Leu Glu His Trp Asp Glu Gln Ala Lys Ala Gly Asn
                880                 885                 890 cgg ttc tac atg aag acg ctg ccg atg ctg tgc cag acc tgc cag atc        2998
Arg Phe Tyr Met Lys Thr Leu Pro Met Leu Cys Gln Thr Cys Gln Ile
            895                 900                 905 ccg atg ctg ttc acc gag ccg ggc gac ccc acc agg ctc tgc gcg cgc        3046
Pro Met Leu Phe Thr Glu Pro Gly Asp Pro Thr Arg Leu Cys Ala Arg
        910                 915                 920 gaa tcg aat tac ttc ggc aac aag ttc cac ttc tgc agt gac cac tgc        3094
Glu Ser Asn Tyr Phe Gly Asn Lys Phe His Phe Cys Ser Asp His Cys
925                 930                 935 aag gag atc ttt gac cac gag ccg gag aag tac gtg caa gcg tgg ctg        3142
Lys Glu Ile Phe Asp His Glu Pro Glu Lys Tyr Val Gln Ala Trp Leu
940                 945                 950                 955 ccc gtg cac cag atc tac cag ggc aac tgc ttc aag ccg ggc gtg gat        3190
Pro Val His Gln Ile Tyr Gln Gly Asn Cys Phe Lys Pro Gly Val Asp
                960                 965                 970 ccg agc gcc gaa ggt ttc gat ccg ctg gct gcc gtg ctc gac tac tac        3238
Pro Ser Ala Glu Gly Phe Asp Pro Leu Ala Ala Val Leu Asp Tyr Tyr
            975                 980                 985 gag gtg gag ccc cgc gac acg atg gat ttc gaa ggc tcc gaa gac cag        3286
Glu Val Glu Pro Arg Asp Thr Met Asp Phe Glu Gly Ser Glu Asp Gln
        990                 995                 1000 aag aac ttt gcg gcg tgg cgc ggc cag gcc acc agc aac tga ccggcagga    3337
Lys Asn Phe Ala Ala Trp Arg Gly Gln Ala Thr Ser Asn
    1005                1010                1015 gacagcc                                                                3344 atg acc gtc aat gcg                                                    3359
Met Thr Val Asn Ala
        1020 ctc aag ccc tac gat ttc ccg ctg atg gac acg gtg gag aag ttc ccc        3407
Leu Lys Pro Tyr Asp Phe Pro Leu Met Asp Thr Val Glu Lys Phe Pro
        1025                1030                1035 gcg ccg ctg ctg tat gtg aac tgg gag aac cac ctg atg ttc ccg gca        3455
Ala Pro Leu Leu Tyr Val Asn Trp Glu Asn His Leu Met Phe Pro Ala
    1040                1045                1050 ccg ttc tgc ctg ccg ctg ccg ccc gag acg ccg ttc agc gcg ctc gcc        3503
Pro Phe Cys Leu Pro Leu Pro Pro Glu Thr Pro Phe Ser Ala Leu Ala
1055                1060                1065 gaa cag atc ctg cca ccc gtc tac ggc tac cac ccg gac ttt gcc cgc        3551
Glu Gln Ile Leu Pro Pro Val Tyr Gly Tyr His Pro Asp Phe Ala Arg
1070                1075                1080                1085 atc gac tgg aag cgc gtg cag tgg ttt cgc tcc ggc caa ccc tgg aca        3599
Ile Asp Trp Lys Arg Val Gln Trp Phe Arg Ser Gly Gln Pro Trp Thr
                1090                1095                1100 ccg gac acg tcg aag agc ctc ggc gag aac ggg ctg ggg cac aag gac        3647
Pro Asp Thr Ser Lys Ser Leu Gly Glu Asn Gly Leu Gly His Lys Asp
            1105                1110                1115 ctg atc agt ttc cgc acg ccg ggg ctg gat ggc atc ggc ggg gca tcg        3695
Leu Ile Ser Phe Arg Thr Pro Gly Leu Asp Gly Ile Gly Gly Ala Ser
        1120                1125                1130
```

-continued

```
atc tga gcgcccggcc ggtgctccag caatgacaag gtatccatc           3740
Ile atg agc cac caa ctt acc atc gag ccg ctc ggc gcg              3776
Met Ser His Gln Leu Thr Ile Glu Pro Leu Gly Ala
1135                1140                1145 acg atc gag gtc gag gaa ggg cag acc att ctc gat gcg gcg ctg cgc  3824
Thr Ile Glu Val Glu Glu Gly Gln Thr Ile Leu Asp Ala Ala Leu Arg
        1150                1155                1160 caa ggc atc tat atc ccg cat gcc tgt tgc cac ggc ctg tgc ggg acc  3872
Gln Gly Ile Tyr Ile Pro His Ala Cys Cys His Gly Leu Cys Gly Thr
        1165                1170                1175 tgc aag gtc tcg gtc ctc gac ggc gag gcc gac ctg ggc gag gcc aac  3920
Cys Lys Val Ser Val Leu Asp Gly Glu Ala Asp Leu Gly Glu Ala Asn
    1180                1185                1190 ccg ttc gcg ttg atg gat ttc gag cgc gag gag ggc aag gcg ctg gcg  3968
Pro Phe Ala Leu Met Asp Phe Glu Arg Glu Glu Gly Lys Ala Leu Ala
1195                1200                1205                1210 tgc tgc gcg acg ctg cag gcc gat acc acc atc gag gcc gat gtc gac  4016
Cys Cys Ala Thr Leu Gln Ala Asp Thr Thr Ile Glu Ala Asp Val Asp
            1215                1220                1225 aag gac ccg gac ggc gag att atc ccg gtg cgg gat ttc gag gcc gac  4064
Lys Asp Pro Asp Gly Glu Ile Ile Pro Val Arg Asp Phe Glu Ala Asp
        1230                1235                1240 gtg atg tgc atc gac cag ctc acc ccg acc atc aag gcg atc cgc ctg  4112
Val Met Cys Ile Asp Gln Leu Thr Pro Thr Ile Lys Ala Ile Arg Leu
        1245                1250                1255 cgg ctc gcg gag ccg atg cgt ttc cag gcg ggc cag tac gtc cag ttc  4160
Arg Leu Ala Glu Pro Met Arg Phe Gln Ala Gly Gln Tyr Val Gln Phe
    1260                1265                1270 gag atc ccg ggc ctg ggc cag acc cgc gct ttc tcg atc gcc aac gcg  4208
Glu Ile Pro Gly Leu Gly Gln Thr Arg Ala Phe Ser Ile Ala Asn Ala
1275                1280                1285                1290 ccg gcg gac gtc gcc gcg acc ggc gag atc gag ctg aac gtg cgg cag  4256
Pro Ala Asp Val Ala Ala Thr Gly Glu Ile Glu Leu Asn Val Arg Gln
            1295                1300                1305 gtg ccg ggc ggc ctt ggc acc ggc tac ctg cac gag cag ctc gcc gcc  4304
Val Pro Gly Gly Leu Gly Thr Gly Tyr Leu His Glu Gln Leu Ala Ala
        1310                1315                1320 ggg gat cgc gtg cgc ttg tcc gga ccc tat ggc cgc ttc ttc gtg cgc  4352
Gly Asp Arg Val Arg Leu Ser Gly Pro Tyr Gly Arg Phe Phe Val Arg
    1325                1330                1335 cgc tcg gcc ggc ctg ccg atg atc ttc atg gcg ggc ggc tcg ggg ctg  4400
Arg Ser Ala Gly Leu Pro Met Ile Phe Met Ala Gly Gly Ser Gly Leu
1340                1345                1350 tcg agc ccg cgc tcc atg atc tgc gac ctg ctg gaa ggc ggc gtc acc  4448
Ser Ser Pro Arg Ser Met Ile Cys Asp Leu Leu Glu Gly Gly Val Thr
1355                1360                1365                1370 gcg ccg att acg ctg gtc tac ggc cag cgc aac gcg aag gag ctg tac  4496
Ala Pro Ile Thr Leu Val Tyr Gly Gln Arg Asn Ala Lys Glu Leu Tyr
            1375                1380                1385 tac cac gac gag ttc cgc gcg ctg agc gag cgc tat ccc aac ttc acc  4544
Tyr His Asp Glu Phe Arg Ala Leu Ser Glu Arg Tyr Pro Asn Phe Thr
        1390                1395                1400 tac gtg ccg gcg ctg tcg gag ggg gcg ggg gac ggc gag gtc gcg cag  4592
Tyr Val Pro Ala Leu Ser Glu Gly Ala Gly Asp Gly Glu Val Ala Gln
    1405                1410                1415 ggc ttc gtc cac gac gtc gcc aag gcg cac ttc gac aat gac ttc tcg  4640
Gly Phe Val His Asp Val Ala Lys Ala His Phe Asp Asn Asp Phe Ser
1420                1425                1430
```

```
ggc cac cag gct tac ctg tgc gga ccg ccc gcg atg atc gac gcc tgc    4686
Gly His Gln Ala Tyr Leu Cys Gly Pro Pro Ala Met Ile Asp Ala Cys
1435                1440                1445                1450 atc acg gcg ctg atg cag ggc cgg ctg ttc gag cgc gac atc tac cac    4736
Ile Thr Ala Leu Met Gln Gly Arg Leu Phe Glu Arg Asp Ile Tyr His
            1455                1460                1465 gag aag ttc att tcg gcg gcg gat gcg cag cag acc cgc agc ccg ctg    4784
Glu Lys Phe Ile Ser Ala Ala Asp Ala Gln Gln Thr Arg Ser Pro Leu
        1470                1475                1480 ttt cgc aag gtg tga c                                              4800
Phe Arg Lys Val
        1485 gtg                                                                4803
Met gac acg tgc atc aag gcc acg gtg cgg gtc gcg cag acg ggt gag tcc    4851
Asp Thr Cys Ile Lys Ala Thr Val Arg Val Ala Gln Thr Gly Glu Ser
        1490                1495                1500 ttc tcg tgc acc gcc ggc gaa tcg ctg ctc gcc ggc atg gca aag ctg    4899
Phe Ser Cys Thr Ala Gly Glu Ser Leu Leu Ala Gly Met Ala Lys Leu
    1505                1510                1515 ggc cgg cgc ggc att ccg gtc ggc tgc ctg aac ggc ggc tgc ggg gtc    4947
Gly Arg Arg Gly Ile Pro Val Gly Cys Leu Asn Gly Gly Cys Gly Val
1520                1525                1530                1535 tgc aag gtg cgg gtg ctg agc ggc gac gtg cgc aag ctg ggc ccg gtc    4995
Cys Lys Val Arg Val Leu Ser Gly Asp Val Arg Lys Leu Gly Pro Val
                1540                1545                1550 agc cgc gcg cat gtc agc gct gac gaa gag ggg ctg ggc tac acg ctg    5043
Ser Arg Ala His Val Ser Ala Asp Glu Glu Gly Leu Gly Tyr Thr Leu
            1555                1560                1565 gcc tgc cgc gtg gcg ccg cag ggc gac gtc gag ctg gag gtg gcc ggg    5091
Ala Cys Arg Val Ala Pro Gln Gly Asp Val Glu Leu Glu Val Ala Gly
        1570                1575                1580 aag atg cag aag ccg ttc ctc tgc tgc gcc cag gcc agg aag taa aggca  5141
Lys Met Gln Lys Pro Phe Leu Cys Cys Ala Gln Ala Arg Lys
    1585                1590                1595 gcaagaaaac atcaacagga gacacatcat gggtgtgatg cggataggcc atgccaacct  5201
gaaggtcatg gacatggaag cggccctgcg ccactacgtg cgggtgctgg gcatgaagga  5261
agtgatgcgc gacgcggacg gtaacgtcta tttgaaatgc tgggacgagt gggacaagta  5321
ctcgctgatc                                                         5331
```

<210> SEQ ID NO 2
<211> LENGTH: 81
<212> TYPE: PRT
<213> ORGANISM: Ralstonia eutropha
<220> FEATURE:
<223> OTHER INFORMATION: TomK polypeptide

<400> SEQUENCE: 2

Met Thr Leu Gln Thr Pro Ala Asn Gln Ala Ser Asp Pro Cys Arg Lys
1               5                   10                  15

Phe Val Arg Val Thr Gly Leu Asn Pro Arg Gly Phe Val Glu Phe Glu
            20                  25                  30

Phe Ala Ile Gly Gly Pro Glu Met Phe Val Glu Leu Thr Leu Pro Ile
        35                  40                  45

Asp Ala Phe Asp Ala Phe Cys Thr Thr Gln Asn Val Val Arg Leu Asp
    50                  55                  60

Asp Ser Gly Ser Asp Phe His Arg Asp Pro Thr Thr Leu Arg Ser Asn
65                  70                  75                  80

Pro

```
<210> SEQ ID NO 3
<211> LENGTH: 331
<212> TYPE: PRT
<213> ORGANISM: Ralstonia eutropha
<220> FEATURE:
<223> OTHER INFORMATION: TomL polypeptide

<400> SEQUENCE: 3
```

Met Thr Ile Glu Leu Lys Thr Val Asp Ile Lys Pro Leu Arg Gln Thr
 1               5                  10                  15

Tyr Ala His Val Ala Arg His Ile Gly Gly Asp Lys Thr Ala Ser Arg
                20                  25                  30

Tyr Gln Glu Gly Met Met Gly Ala Gln Pro Glu Thr Asn Phe His Tyr
            35                  40                  45

Arg Pro Thr Trp Asp Pro Ala His Gln Ile Phe Asp Ala Ser Arg Ser
        50                  55                  60

Ala Ile Arg Met Ala Ser Trp Tyr Val Leu Lys Asp Pro Arg Gln Tyr
65                  70                  75                  80

Tyr Tyr Ala Ser Trp Thr Thr Ala Arg Ala Arg Gln Gln Asp Thr Met
                85                  90                  95

Glu Ser Asn Phe Glu Phe Val Glu Ser Arg Arg Met Ile Asp Arg Met
            100                 105                 110

Pro Ala Glu Val Ala Lys His Ala Leu Asp Leu Leu Val Pro Leu Arg
        115                 120                 125

His Ala Ala Trp Gly Ala Asn Met Asn Asn Ala Gln Val Cys Ala Leu
130                 135                 140

Gly Tyr Gly Thr Ala Phe Thr Ala Ala Met Phe His Ala Met Asp
145                 150                 155                 160

Asn Leu Gly Val Ala Gln Tyr Leu Thr Arg Leu Ala Leu Ala Val Ala
                165                 170                 175

Gly Pro Glu Val Leu Asp Ala Gly Arg His Ala Trp Leu Glu His Pro
            180                 185                 190

Ala Trp Gln Pro Leu Arg His Tyr Ile Glu Asp Thr Phe Val Val Asp
        195                 200                 205

Asp Pro Val Glu Leu Phe Val Ala Gln Asn Leu Ala Leu Asp Gly Met
    210                 215                 220

Leu Tyr Pro Leu Val Tyr Asp Arg Phe Val Asp Glu Arg Ile Ala Leu
225                 230                 235                 240

Gly Gly Gly Ser Ala Ile Ala Met Leu Thr Ala Phe Met Pro Glu Trp
                245                 250                 255

His Glu Glu Ser Lys Arg Trp Val Asp Ala Val Val Lys Thr Met Ala
            260                 265                 270

Ala Glu Ser Glu Glu Asn Lys Ala Leu Leu Ala His Trp Thr Arg Asp
        275                 280                 285

Trp Ala Gly Arg Ala Phe Ala Ala Leu Gln Pro Val Ala Glu Leu Ala
    290                 295                 300

Phe Pro Thr His Ala Pro Glu Val Leu Asp Ala Val Arg Glu Gln Phe
305                 310                 315                 320

Gln Thr Arg Ile Ser Lys Leu Gly Ile Ala Leu
                325                 330

```
<210> SEQ ID NO 4
<211> LENGTH: 89
<212> TYPE: PRT
```

```
<213> ORGANISM: Ralstonia eutropha
<220> FEATURE:
<223> OTHER INFORMATION: TomM polypeptide

<400> SEQUENCE: 4
```

| | | | | | | | | | | | | | | | |
|---|---|---|---|---|---|---|---|---|---|---|---|---|---|---|---|
| Met | Ser | Asn | Val | Phe | Ile | Ala | Phe | Gln | Ala | Asn | Glu | Glu | Ser | Arg | Pro |
| 1 | | | | 5 | | | | | 10 | | | | | 15 | |
| Val | Val | Glu | Ala | Ile | Leu | Ala | Asp | Asn | Pro | Asp | Ala | Val | Leu | Val | Glu |
| | | | 20 | | | | | 25 | | | | | 30 | | |
| Ser | Pro | Gly | Met | Val | Lys | Ile | Asp | Ala | Pro | Ser | His | Leu | Thr | Ile | Arg |
| | | 35 | | | | | 40 | | | | | 45 | | | |
| Arg | Gln | Thr | Ile | Glu | Glu | Leu | Thr | Gly | Thr | Arg | Phe | Asp | Leu | Gln | Gln |
| | 50 | | | | | 55 | | | | | 60 | | | | |
| Ile | His | Val | Asn | Leu | Ile | Thr | Leu | Ser | Gly | His | Ile | Glu | Glu | Asp | Asp |
| 65 | | | | | 70 | | | | | 75 | | | | | 80 |
| Asp | Ala | Phe | Thr | Leu | Ser | Trp | Lys | His | | | | | | | |
| | | | | 85 | | | | | | | | | | | |

```
<210> SEQ ID NO 5
<211> LENGTH: 515
<212> TYPE: PRT
<213> ORGANISM: Ralstonia eutropha
<220> FEATURE:
<223> OTHER INFORMATION: TomN polypeptide

<400> SEQUENCE: 5
```

| | | | | | | | | | | | | | | | |
|---|---|---|---|---|---|---|---|---|---|---|---|---|---|---|---|
| Met | Glu | Thr | Pro | Thr | Gln | Lys | Lys | Leu | Gly | Leu | Lys | Glu | Arg | Tyr | |
| 1 | | | | 5 | | | | | 10 | | | | | 15 | |
| Ala | Ala | Met | Thr | Arg | Gly | Leu | Gly | Trp | Asp | Thr | Thr | Tyr | Gln | Pro | Met |
| | | | 20 | | | | | 25 | | | | | 30 | | |
| Asp | Lys | Val | Phe | Pro | Tyr | Asp | Arg | Tyr | Glu | Gly | Ile | Lys | Ile | His | Asp |
| | | | 35 | | | | | 40 | | | | | 45 | | |
| Trp | Asp | Lys | Trp | Val | Asp | Pro | Phe | Arg | Leu | Thr | Met | Asp | Ala | Tyr | Trp |
| | 50 | | | | | 55 | | | | | 60 | | | | |
| Lys | Tyr | Gln | Gly | Glu | Lys | Glu | Lys | Leu | Tyr | Ala | Val | Ile | Asp | Ala | |
| 65 | | | | | 70 | | | | | 75 | | | | | 80 |
| Phe | Thr | Gln | Asn | Asn | Ala | Phe | Leu | Gly | Val | Thr | Asp | Ala | Arg | Tyr | Ile |
| | | | | 85 | | | | | 90 | | | | | 95 | |
| Asn | Ala | Leu | Lys | Leu | Phe | Val | Gln | Gly | Val | Thr | Pro | Leu | Glu | Tyr | Leu |
| | | | 100 | | | | | 105 | | | | | 110 | | |
| Ala | His | Arg | Gly | Phe | Ala | His | Val | Gly | Arg | His | Phe | Thr | Gly | Glu | Gly |
| | | 115 | | | | | 120 | | | | | 125 | | | |
| Ala | Arg | Val | Ala | Cys | Gln | Met | Gln | Ser | Ile | Asp | Glu | Leu | Arg | His | Tyr |
| | 130 | | | | | 135 | | | | | 140 | | | | |
| Gln | Thr | Glu | Thr | His | Ala | Leu | Ser | Thr | Tyr | Asn | Lys | Phe | Phe | Asn | Gly |
| 145 | | | | | 150 | | | | | 155 | | | | | 160 |
| Leu | His | His | Ser | Asn | His | Trp | Phe | Asp | Arg | Val | Trp | Tyr | Leu | Ser | Val |
| | | | | 165 | | | | | 170 | | | | | 175 | |
| Pro | Lys | Ser | Phe | Phe | Glu | Asp | Ala | Tyr | Ser | Ala | Gly | Pro | Glu | Phe | |
| | | | 180 | | | | | 185 | | | | | 190 | | |
| Leu | Thr | Ala | Val | Ser | Phe | Ser | Phe | Glu | Tyr | Val | Leu | Thr | Asn | Leu | Leu |
| | | 195 | | | | | 200 | | | | | 205 | | | |
| Phe | Val | Pro | Phe | Met | Ser | Gly | Ala | Ala | Tyr | Asn | Gly | Asp | Met | Ser | Thr |
| | 210 | | | | | 215 | | | | | 220 | | | | |
| Val | Thr | Phe | Gly | Phe | Ser | Ala | Gln | Ser | Asp | Glu | Ser | Arg | His | Met | Thr |
| 225 | | | | | 230 | | | | | 235 | | | | | 240 |

-continued

```
Leu Gly Ile Glu Cys Ile Lys Phe Leu Leu Glu Gln Pro Asp Asn
                245                 250                 255

Val Pro Ile Val Gln Arg Trp Ile Asp Lys Trp Phe Trp Arg Gly Tyr
            260                 265                 270

Arg Leu Leu Thr Leu Val Ala Met Met Met Asp Tyr Met Gln Pro Lys
        275                 280                 285

Arg Val Met Ser Trp Arg Glu Ala Trp Glu Met Tyr Ala Glu Gln Asn
    290                 295                 300

Gly Gly Ala Leu Phe Lys Asp Leu Ala Arg Tyr Gly Ile Arg Glu Pro
305                 310                 315                 320

Lys Gly Trp Gln Asp Ala Cys Glu Gly Lys Asp His Ile Ser His Gln
                325                 330                 335

Ala Trp Ala Thr Phe Tyr Gly Phe Asn Ala Ala Pro Phe His Thr
            340                 345                 350

Trp Val Pro Gln Gln Asp Glu Met Ala Trp Leu Ser Ala Lys Tyr Pro
        355                 360                 365

Glu Thr Phe Asp Gln His Tyr Arg Pro Arg Leu Glu His Trp Asp Glu
    370                 375                 380

Gln Ala Lys Ala Gly Asn Arg Phe Tyr Met Lys Thr Leu Pro Met Leu
385                 390                 395                 400

Cys Gln Thr Cys Gln Ile Pro Met Leu Phe Thr Glu Pro Gly Asp Pro
                405                 410                 415

Thr Arg Leu Cys Ala Arg Glu Ser Asn Tyr Phe Gly Asn Lys Phe His
            420                 425                 430

Phe Cys Ser Asp His Cys Lys Glu Ile Phe Asp His Glu Pro Glu Lys
        435                 440                 445

Tyr Val Gln Ala Trp Leu Pro Val His Gln Ile Tyr Gln Gly Asn Cys
    450                 455                 460

Phe Lys Pro Gly Val Asp Pro Ser Ala Glu Gly Phe Asp Pro Leu Ala
465                 470                 475                 480

Ala Val Leu Asp Tyr Tyr Glu Val Glu Pro Arg Asp Thr Met Asp Phe
                485                 490                 495

Glu Gly Ser Glu Asp Gln Lys Asn Phe Ala Ala Trp Arg Gly Gln Ala
            500                 505                 510

Thr Ser Asn
        515

<210> SEQ ID NO 6
<211> LENGTH: 118
<212> TYPE: PRT
<213> ORGANISM: Ralstonia eutropha
<220> FEATURE:
<223> OTHER INFORMATION: TomO polypeptide

<400> SEQUENCE: 6

Met Thr Val Asn Ala Leu Lys Pro Tyr Asp Phe Pro Leu Met Asp Thr
  1               5                  10                  15

Val Glu Lys Phe Pro Ala Pro Leu Leu Tyr Val Asn Trp Glu Asn His
             20                  25                  30

Leu Met Phe Pro Ala Pro Phe Cys Leu Pro Leu Pro Pro Glu Thr Pro
         35                  40                  45

Phe Ser Ala Leu Ala Glu Gln Ile Leu Pro Pro Val Tyr Gly Tyr His
     50                  55                  60

Pro Asp Phe Ala Arg Ile Asp Trp Lys Arg Val Gln Trp Phe Arg Ser
 65                  70                  75                  80
```

```
Gly Gln Pro Trp Thr Pro Asp Thr Ser Lys Ser Leu Gly Glu Asn Gly
                85                  90                  95

Leu Gly His Lys Asp Leu Ile Ser Phe Arg Thr Pro Gly Leu Asp Gly
            100                 105                 110

Ile Gly Gly Ala Ser Ile
            115

<210> SEQ ID NO 7
<211> LENGTH: 352
<212> TYPE: PRT
<213> ORGANISM: Ralstonia eutropha
<220> FEATURE:
<223> OTHER INFORMATION: TomP polypeptide

<400> SEQUENCE: 7

Met Ser His Gln Leu Thr Ile Glu Pro Leu Gly Ala Thr Ile Glu Val
 1               5                  10                  15

Glu Glu Gly Gln Thr Ile Leu Asp Ala Ala Leu Arg Gln Gly Ile Tyr
            20                  25                  30

Ile Pro His Ala Cys Cys His Gly Leu Cys Gly Thr Cys Lys Val Ser
        35                  40                  45

Val Leu Asp Gly Glu Ala Asp Leu Gly Glu Ala Asn Pro Phe Ala Leu
     50                  55                  60

Met Asp Phe Glu Arg Glu Gly Lys Ala Leu Ala Cys Cys Ala Thr
 65                  70                  75                  80

Leu Gln Ala Asp Thr Thr Ile Glu Ala Asp Val Asp Lys Asp Pro Asp
                85                  90                  95

Gly Glu Ile Ile Pro Val Arg Asp Phe Glu Ala Asp Val Met Cys Ile
            100                 105                 110

Asp Gln Leu Thr Pro Thr Ile Lys Ala Ile Arg Leu Arg Leu Ala Glu
        115                 120                 125

Pro Met Arg Phe Gln Ala Gly Gln Tyr Val Gln Phe Glu Ile Pro Gly
    130                 135                 140

Leu Gly Gln Thr Arg Ala Phe Ser Ile Ala Asn Ala Pro Ala Asp Val
145                 150                 155                 160

Ala Ala Thr Gly Glu Ile Glu Leu Asn Val Arg Gln Val Pro Gly Gly
                165                 170                 175

Leu Gly Thr Gly Tyr Leu His Glu Gln Leu Ala Ala Gly Asp Arg Val
            180                 185                 190

Arg Leu Ser Gly Pro Tyr Gly Arg Phe Phe Val Arg Arg Ser Ala Gly
        195                 200                 205

Leu Pro Met Ile Phe Met Ala Gly Gly Ser Gly Leu Ser Ser Pro Arg
    210                 215                 220

Ser Met Ile Cys Asp Leu Leu Glu Gly Gly Val Thr Ala Pro Ile Thr
225                 230                 235                 240

Leu Val Tyr Gly Gln Arg Asn Ala Lys Glu Leu Tyr Tyr His Asp Glu
                245                 250                 255

Phe Arg Ala Leu Ser Glu Arg Tyr Pro Asn Phe Thr Tyr Val Pro Ala
            260                 265                 270

Leu Ser Glu Gly Ala Gly Asp Gly Glu Val Ala Gln Gly Phe Val His
        275                 280                 285

Asp Val Ala Lys Ala His Phe Asp Asn Asp Phe Ser Gly His Gln Ala
    290                 295                 300

Tyr Leu Cys Gly Pro Pro Ala Met Ile Asp Ala Cys Ile Thr Ala Leu
305                 310                 315                 320
```

```
Met Gln Gly Arg Leu Phe Glu Arg Asp Ile Tyr His Glu Lys Phe Ile
                325                 330                 335

Ser Ala Ala Asp Ala Gln Gln Thr Arg Ser Pro Leu Phe Arg Lys Val
                340                 345                 350

<210> SEQ ID NO 8
<211> LENGTH: 111
<212> TYPE: PRT
<213> ORGANISM: Ralstonia eutropha
<220> FEATURE:
<223> OTHER INFORMATION: TomQ polypeptide

<400> SEQUENCE: 8

Met Asp Thr Cys Ile Lys Ala Thr Val Arg Val Ala Gln Thr Gly Glu
 1               5                  10                  15

Ser Phe Ser Cys Thr Ala Gly Glu Ser Leu Leu Ala Gly Met Ala Lys
                20                  25                  30

Leu Gly Arg Arg Gly Ile Pro Val Gly Cys Leu Asn Gly Gly Cys Gly
            35                  40                  45

Val Cys Lys Val Arg Val Leu Ser Gly Asp Val Arg Lys Leu Gly Pro
        50                  55                  60

Val Ser Arg Ala His Val Ser Ala Asp Glu Glu Gly Leu Gly Tyr Thr
 65                  70                  75                  80

Leu Ala Cys Arg Val Ala Pro Gln Gly Asp Val Glu Leu Glu Val Ala
                85                  90                  95

Gly Lys Met Gln Lys Pro Phe Leu Cys Cys Ala Gln Ala Arg Lys
                100                 105                 110

<210> SEQ ID NO 9
<211> LENGTH: 34
<212> TYPE: DNA
<213> ORGANISM: Artificial Sequence
<220> FEATURE:
<223> OTHER INFORMATION: Designed PCR primer

<400> SEQUENCE: 9
atcgacccat tgaccatggc cctgcagacc ccag                           34

<210> SEQ ID NO 10
<211> LENGTH: 34
<212> TYPE: DNA
<213> ORGANISM: Artificial Sequence
<220> FEATURE:
<223> OTHER INFORMATION: Designed PCR primer

<400> SEQUENCE: 10
ctcaggagca acccatggca atcgagctga aaac                           34

<210> SEQ ID NO 11
<211> LENGTH: 34
<212> TYPE: DNA
<213> ORGANISM: Artificial Sequence
<220> FEATURE:
<223> OTHER INFORMATION: Designed PCR primer

<400> SEQUENCE: 11
tacttccagt acgcgtcgat ggtcaggcgg aacg                           34

<210> SEQ ID NO 12
<211> LENGTH: 34
<212> TYPE: DNA
<213> ORGANISM: Artificial Sequence
<220> FEATURE:
```

-continued

```
<223> OTHER INFORMATION: Designed PCR primer

<400> SEQUENCE: 12
gcccagcttt gccatggcgg cgagcagcga ttcg                                34

<210> SEQ ID NO 13
<211> LENGTH: 30
<212> TYPE: DNA
<213> ORGANISM: Artificial Sequence
<220> FEATURE:
<223> OTHER INFORMATION: Designed PCR primer

<400> SEQUENCE: 13
caatgaaagg ggatccgagg cgacatcgac                                     30

<210> SEQ ID NO 14
<211> LENGTH: 30
<212> TYPE: DNA
<213> ORGANISM: Artificial Sequence
<220> FEATURE:
<223> OTHER INFORMATION: Designed PCR primer

<400> SEQUENCE: 14
atgtcgacgg gatccatctc gattgtcacg                                     30
```

DNA FRAGMENT CARRYING TOLUENE MONOOXYGENASE, GENE, RECOMBINANT PLASMID, TRANSFORMED MICROORGANISM, METHOD FOR DEGRADING CHLORINATED ALIPHATIC HYDROCARBON COMPOUNDS AND AROMATIC COMPOUNDS, AND METHOD FOR ENVIRONMENTAL REMEDIATION

CROSS REFERENCE TO RELATED APPLICATIONS

This application is a division of parent application Ser. No. 09/453,956 filed on Dec. 3, 1999 now U.S. Pat. No. 6,472,191.

BACKGROUND OF THE INVENTION

1. Field of the Invention

The present invention relates to a novel DNA fragment carrying a toluene monooxygenase gene, a novel recombinant DNA containing the DNA fragment, a transformant containing the recombinant DNA, and a method for degrading chlorinated aliphatic hydrocarbon compounds such as trichloroethylene (TCE) and dichloroethylene (DCE) and aromatic compounds such as toluene, benzene, phenol, and cresol. The present invention also relates to a method for environmental remediation useful for cleaning of aqueous media such as wastewater and effluent containing at least either a chlorinated aliphatic hydrocarbon compound or an aromatic compound and air (gas phase) and soil polluted with chlorinated aliphatic hydrocarbon compounds.

2. Related Background Art

Recently, it has become a serious problem the environmental pollution with volatile organic chlorinated compounds which are harmful to the organisms and hardly degradable. Especially, the soil in the industrial areas in Japan as well as abroad is considered to be contaminated with chlorinated aliphatic hydrocarbon compounds such as tetrachloroethylene (PCE), trichloroethylene (TCE), and dichloroethylene (DCE) and aromatic compounds such as toluene, benzene, phenol, and cresol. In fact, there have been a number of reports on actual detection of such pollutants through environmental surveys. It is supposed that these compounds remaining in soil dissolve in ground water via rainwater, and thereby spread over the surrounding areas. There is a strong suspicion that these compounds are carcinogens, and further, these are quite stable in the environment; therefore contamination of groundwater, which is used as a source of drinking water, has become a serious social problem. Therefore, cleaning of soil and aqueous media such as contaminated groundwater by removal and degradation of these compounds and accompanying cleaning of the surrounding gas phase is quite important in view of the environment protection, and technologies for remedying the environment (for example, adsorption treatment using activated carbon, degradation treatment using light and heat) have been developed. Current technologies, however, are not always practical in terms of cost and operability. Recently, microbial degradation of chlorinated aliphatic hydrocarbon compounds such as TCE that is stable in environment has been reported. The microbial degradation method has advantages such as: (1) degradation of chlorinated aliphatic hydrocarbon compounds into harmless substances by using appropriately selected microorganism; (2) no requirement for any special chemicals in principle; and (3) reduction of the labor and costs of maintenance.

The examples of microorganisms capable of degrading TCE are as follows:

*Welchia alkenophila* sero 5 (U.S. Pat. No. 4,877,736, ATCC 53570, *Welchia alkenophila* sero 33 (U.S. Pat. No. 4,877,736, ATCC 53571), *Methylocystis* sp. Strain M (Agric. Biol. Chem., 53, 2903 (1989), Biosci. Biotech. Bichem., 56, 486 (1992), ibid. 56, 736 (1992)), *Methylosinus trichosporium* OB3b (Am. Chem. Soc. Natl. meet. Div. Environ. Microbiol., 29, 365 (1989), Appl. Environ. Microbiol., 55, 3155 (1989), Appl. Biochem. Biotechnol. 28, 877 (1991), Japanese Patent Application Laid-Open No. 2-92274 specification, Japanese Patent Laid-Open Application No. 3-292970), *Methylomonas* sp. MM2 (Appl. Environ. Microbiol., 57, 236 (1991), *Alcaligenes denitrificans* ssp. *Xylosoxidans* JE75 (Arch. Microbiol., 154, 410 (1990), *Alcaligenes eutrophus* JMP134 (Appl. Environ. Microbiol., 56, 1179 (1990), *Alcaligenes eutrophus* FERM-13761 (Japanese Patent Laid-Open Application No. 7-123976), *Pseudomonas aeruginosa* J1104 (Japanese Patent Application Laid-Open No. 7-236895), *Mycobacterium vaccae* J0B5 (J. Gen. Microbiol., 82, 163 (1974), Appl. Environ. Microbiol., 55, 2960 (1989), ATCC 29678), *Pseudomonas putida* BH (Gesuidou Kyoukai-shi (Japan Sewage Works Association Journal), 24, 27 (1987)), *Pseudomonas* sp. strain G4 (Appl. Environ. Microbiol., 52, 383 (1968), ibid. 53, 949 (1987), ibid. 54, 951 (1988), ibid. 56, 279 (1990), ibid. 57, 193 (1991), U.S. Pat. No. 4,925,802, ATCC 53617, this strain was first classified as *Pseudomonas cepacia* and then changed to *Pseudomonas* sp.), *Pseudomonas mendocia* KR-1 (Bio/Technol.; 7, 282 (1989)), *Pseudomonas putida* F1 (Appl. Environ Microbiol., 54, 1703 (1988), ibid. 54, 2578 (1988)), *fluorescens* PFL12 (Appl. Environ. Microbiol., 54, 2578 (1988)), *Pseudomonas putida* KWI-9 (Japanese Patent Application Laid-Open No. 6-70753), *Burkholderia cepacia* KK01 (Japanese Patent Application Laid-Open No. 6-22769), *Nitrosomonas europaea* (Appl. Environ. Microbio., 56, 1169 (1990), *Lactobacillus vaginalis* sp. nov (Int. J. Syst. Bacteriol., 39, 368 (1989), ATCC 49540), *Nocardia corallina* B-276 (Japanese Patent Application Laid-Open No. 8-70881, FERM BP-5124, ATCC 31338), and so on.

The problem in actually using these degrading microorganisms in environmental remediation treatment, however, resides in optimizing and maintaining expression of their degradation activity for chlorinated aliphatic hydrocarbon compounds such as TCE. In an environmental remediation treatment which utilizes phenol, toluene, methane, or the like as an inducer, continuous supply of the inducer is indispensable, since depletion of such inducers directly results in stoppage of degradation of chlorinated aliphatic hydrocarbon compounds. Presence of such inducers, on the other hand, may inhibit the efficient degradation of the target substance such as TCE, since the affinity of the chlorinated aliphatic hydrocarbon compounds such as TCE as a substrate is considerably low in comparison with these inducers. In addition, precise control of the inducer concentration on the treatment spot is difficult.

Thus, use of an inducer is a large problem in practical application of environmental remediation treatment utilizing microorganisms.

In order to solve the problem, Nelson et al. developed a method using tryptophan as an inducer for degradation of volatile organic chlorinated compounds (Japanese Patent Application Laid-Open No. 4-502277). Tryptophan, however, is a very expensive substance, and although tryptophane has no toxicity or risk as a substance, it is not preferable to introduce excessive carbon and nitrogen sources into environment since it may induce eutrophication. In addition, the problem that tryptophan serves as a competitive inhibitor in degradation of TCE still remains.

Shields et al. obtained a mutant strain of *Pseudomonas cepacia* G4 (changed to *Pseudomonas* sp. upon deposition to ATCC) by the transposon technique, which mutant strain does not require an inducer (in this case, phenol or toluene) and can degrade TCE (Appl. Environ. Microbiol., 58, 3977 (1992), International Publication No. WO/19738). Also, a mutant not requiring methane as the inducer has been isolated from *Methylosinus trichosporium* OB3b, a methanotroph capable of degrading TCE (U.S. Pat. No. 5,316, 940).

Japanese Patent Application Laid-Open No. 8-294387 also discloses strain JM1 (FERM BP-5352) capable of degrading volatile organic chlorinated compounds and aromatic compounds without requiring an inducer, isolated by nitrosoguanidine mutagenization of strain J1 (FERM BP-5102). While, it has been studied to introduce resting cells expressing TCE-degrading activity into the remediation site after the preculture of the cells in the presence of an inducer (Environ. Sci. Technol., 30, 1982 (1996)).

It has been reported that remediation treatment not requiring the inducer actually makes the remediation treatment easy and efficient compared to the conventional treatment using inducers.

However, the growth control of the degrading microorganisms is very important for both the expression of the degradation activity on demand and the continuation of degradation. When resting cells are used, it is a problem to be solved that TCE cannot be degraded beyond the amount and period of degradation capacity of the introduced resting cells. In addition, in a large scale treatment, there are further problems that degradation activity will decrease since it takes a long time to prepare resting cells; the treating apparatus must be large in scale; treatment process is complicated; and the cost may be unfavorably high. Accordingly, it has been attempted to introduce a plasmid carrying a DNA fragment containing a gene region encoding oxygenase or hydroxylase into a host microorganism to make the host express the TCE degradation activity constitutively or inducibly using a harmless inducer. For example, there are *Pseudomonas mendocina* KR-1 (Japanese Patent Application Laid-Open No. 2-503866, *Pseudomonas putida* KWI-9 (Japanese Patent Application Laid-Open No. 6-105691), *Pseudomonas putida* BH (Summary of 3rd Conference on Pollution of Ground Water/Soil and Its Protective Countermeasure, p.213 (1994)), and a transformant carrying both a toluene degradation enzyme gene derived from *Pseudomonas putida* F1 and a biphenyl degradation enzyme gene derived from *Pseudomonas pseudoalkaligenes* (Japanese Patent Application Laid-Open No. 7-143882). However, the reported TCE degradation activity of the transformants are low, and the advantages of the transformants has not been fully exploited for efficient degradation of TCE, such as the ease of degradation control, freedom in designing recombinant, and no requirements for inducers, far from efficient TCE degradation.

SUMMARY OF THE INVENTION

It is an object of the present invention to provide a novel DNA fragment encoding a toluene monooxygenase of a high efficiency in degrading aromatic compounds and/or organic chorine compounds, a novel recombinant DNA containing the DNA fragment, and a transformant containing the recombinant DNA. It is another object of the present invention to provide an efficient biodegradation method for halogenated aliphatic compounds such as trichloroethylene (TCE) and dichloroethylene (DCE) and aromatic compounds such as toluene, benzene, phenol, and cresol using the transformant, specifically an efficient environmental remediation method useful for cleaning aqueous media such as wastewater and effluent containing halogenated aliphatic hydrocarbon compounds and/or aromatic compounds, remedying soil polluted with halogenated aliphatic hydrocarbon compounds or aromatic compounds, and cleaning air (gas phase) polluted with halogenated aliphatic hydrocarbon compounds.

The inventors of the present invention isolated a microorganism *Ralstonia eutropha* strain TB64 having a toluene monooxygenase that oxidizes toluene to ortho-cresol and 3-methylcatechol and deposited it in the National Institute of Bioscience and Human Technology, Agency of Industrial Science and Technology in accordance with the requirements of the Budapest Treaty, Deposit Date: Sep. 3, 1998, Accession No. FERM BP-6933). The inventors strained to isolate the toluene monooxygenase gene from the above strain TB64 and successful isolation and characterization of the gene completed the present invention.

According to one aspect of the present invention, there is provided a DNA fragment of about 5.3 Kb containing a toluene monooxygenase gene, having 3 BamHI, 1 ClaI, 1 EcoRI, 3 KpnI, 2 NcoI, 2 NspV, 2 ScaI, 2 SmaI, 2 SphI, 1 StuI, 0 DraI, 0 EcoRV, 0 HindIII, 0 HpaI, 0 NdeI, 0 PvuII, 0 SacI, 0 Sse83871, 0 XbaI, 0 XhoI restriction sites, and having a restriction map of:

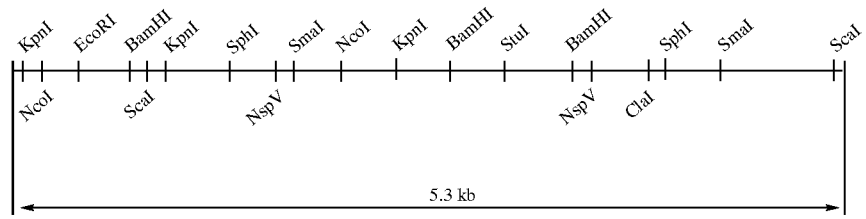

According to another aspect of the present invention, there is provided a DNA fragment having a nucleotide sequence of SEQ ID NO: 1 in the Sequence Listing.

According to another aspect of the present invention, there is provided a DNA fragment having a nucleotide sequence of SEQ ID NO: 1 with deletion, substitution, and/or addition of one or more nucleotides encoding a protein having a toluene monooxygenase activity.

According to another aspect of the present invention, there is provided a recombinant DNA comprising a vector which can be replicate or maintained in a host and the above mentioned DNA fragment.

According to another aspect of the present invention, there is provided a DNA fragment containing a portion encoding a toluene monooxygenase, the portion comprising a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, and the regions are aligned so that expressed TomL–TomP polypeptides can form an active monooxygenase protein.

According to still another aspect of the present invention, there is provided a recombinant DNA comprising a vector, a promoter, and the above mentioned DNA fragment, wherein the vector and the promoter are functionally ligated to the DNA fragment to enable expression of the toluene monooxygenase encoded by the DNA fragment in the host.

According to still another aspect of the present invention, there is provided a DNA fragment comprising a region encoding a polypeptide TomK which has an amino acid sequence of SEQ ID NO: 2 and a property to enhance the toluene monooxygenase activity of a protein comprised of at least TomL–TomP; or a region encoding a variant TomK in which the amino acid sequence of SEQ ID NO: 2 is altered with the proviso that the property to enhance the toluene monooxygenase activity is not impaired.

According to still another aspect of the present invention, there is provided another recombinant DNA comprising a vector, a promoter, a first DNA fragment and a second DNA fragment;

wherein the first DNA encodes a toluene monooxygenase and comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, the second DNA fragment encodes a polypeptide TomK having an amino acid sequence of SEQ ID NO: 2 and a property to enhance the toluene monooxygenase activity of a protein comprised of at least TomL to TomP; or encodes a variant TomK polypeptide in which the amino acid sequence of SEQ ID NO: 2 is altered with the proviso that the property to enhance the toluene monooxygenase activity is not impaired;

the first DNA fragment is functionally linked to the promoter to express the toluene monooxygenase activity, and the second DNA fragment is functionally linked to the promoter to express the property to enhance the activity of the toluene monooxygenase encoded by the first DNA fragment.

According to still another aspect of the present invention, there is provided a recombinant DNA comprising a vector; a first promoter and a first DNA fragment; and a second promoter and a second DNA fragment;

wherein the first DNA encodes a toluene monooxygenase and comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, the second DNA fragment encodes a polypeptide TomK having an amino acid sequence of SEQ ID NO: 2 and a property to enhance the toluene monooxygenase activity of a protein comprised of at least TomL to TomP; or encodes a variant TomK polypeptide in which the amino acid sequence of SEQ ID NO: 2 is altered with the proviso that the property to enhance the toluene monooxygenase activity is not impaired;

the first DNA fragment is functionally linked to the first promoter to express the toluene monooxygenase activity, and the second DNA fragment is functionally linked to the second promoter to express the property to enhance the activity of the toluene monooxygenase encoded by the first DNA fragment.

According to still another aspect of the present invention, there is provided a transformant obtainable by introducing a recombinant DNA into a host microorganism, the recombinant DNA comprising a vector which can replicate or maintained in the host and ligated to a DNA fragment of about 5.3 Kb containing a toluene monooxygenase gene, having 3 BamHI, 1 ClaI, 1 EcoRI, 3 KpnI, 2 NcoI, 2 NspV, 2 ScaI, 2 SmaI, 2 SphI, 1 StuI, 0 DraI, 0 EcoRV, 0 HindIII, 0 HpaI, 0 NdeI, 0 PvuII, 0 SacI, 0 Sse83871, 0 XbaI, 0 XhoI restriction sites, and having a restriction map of:

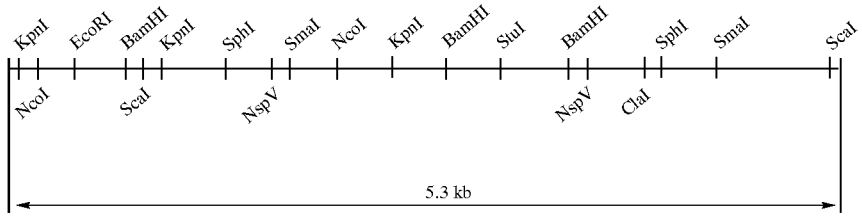

According to still another aspect of the present invention, there is provided a transformant obtainable by introducing a recombinant DNA comprising the DNA fragment having a nucleotide sequence of SEQ ID NO: 1 and ligated to a vector which can replicate or maintained in the host.

According to still another aspect of the present invention, there is provided a transformant obtainable by introducing into a host microorganism a recombinant DNA which comprises a vector, a promoter, and a DNA fragment, wherein the vector and the promoter are functionally ligated to the DNA fragment to enable expression of the toluene monooxygenase encoded by the DNA fragment in the host, wherein the DNA fragment comprises a region sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing.

Further, according to still another aspect of the present invention, there is provided a transformant obtainable by introducing into a host microorganism a recombinant DNA comprising a vector, a promoter, a first DNA fragment, and a second DNA fragment;

wherein the first DNA encodes a toluene monooxygenase and comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, the second DNA fragment encodes a polypeptide TomK having an amino acid sequence of SEQ ID NO: 2 and a property to enhance the toluene monooxygenase activity of a protein comprised of at least TomL to TomP; or encodes a variant TomK polypeptide in which the amino acid sequence of SEQ ID NO: 2 is altered with the proviso that the property to enhance the toluene monooxygenase activity is not impaired;

the first DNA fragment is functionally linked to the promoter to express the toluene monooxygenase activity, and the second DNA fragment is functionally linked to the promoter to express the property to enhance the activity of the toluene monooxygenase encoded by the first DNA fragment.

Further, according to still another aspect of the present invention there is provided a transformant obtainable by introducing into a host microorganism a recombinant DNA comprising a vector, a first promoter and a first DNA fragment, and a second promoter and a second DNA fragment;

wherein the first DNA encodes a toluene monooxygenase and comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, the second DNA fragment encodes a polypeptide TomK having an amino acid sequence of SEQ ID NO: 2 and a property to enhance the toluene monooxygenase activity of a protein comprised of at least TomL to TomP; or encodes a variant TomK polypeptide in which the amino acid sequence of SEQ ID NO: 2 is altered with the proviso that the property to enhance the toluene monooxygenase activity is not impaired;

the first DNA fragment is functionally linked to the first promoter to express the toluene monooxygenase activity, and the second DNA fragment is functionally linked to the second promoter to express the property to enhance the activity of the toluene monooxygenase encoded by the first DNA fragment.

According to still another aspect of the present invention, there is provided a method for producing a toluene monooxygenase, which comprises a step of making an above transformant produce a toluene monooxygenase being a gene product of the DNA fragment introduced into the transformant.

According to still another aspect of the present invention, there is provided a method for degrading at least either of a chlorinated aliphatic hydrocarbon compound or an aromatic compound, which comprises a step of degrading at least either of the chlorinated aliphatic hydrocarbon compound or aromatic compound using the transformant according to any one of the aspects of the present invention mentioned above.

According to still another aspect of the present invention, there is provided a method for remedying an environment polluted with at least either of a chlorinated aliphatic hydrocarbon compound or an aromatic compound as a pollutant, comprising a step of degrading the pollutants using the transformant according to any one of the aspects of the present invention mentioned above.

According to still another aspect of the present invention, there is provided a component polypeptide having any one of amino acid sequences of SEQ ID Nos: 2–8, which can constitute a toluene monooxygenase.

According to still another aspect of the present invention, there is provided a toluene monooxygenase comprising at least component polypeptides TomL–TomP of amino acid sequences of SEQ ID NOs: 3–7.

According to still another aspect of the present invention, there is provided a variant toluene monooxygenase obtainable by mutating the above mentioned toluene monooxygenase not to loose the enzyme activity.

BRIEF DESCRIPTION OF THE DRAWINGS

FIG. 2 is comprised of FIGS. 2A, 2B, 2C, 2D, 2E, 2F, 2G, 2H, 2I, 2J, 2K, 2L, 2M, 2N, 2O, 2P, 2Q, 2R and 2S showing a nucleotide sequence (SEQ ID NO: 1) of a toluene monooxygenase gene of FERM BP-6933;

FIG. 3 is an amino acid sequence (TomK) (SEQ ID NO: 2) encoded by a region tomK (nucleotides 200 to 445 of SEQ ID NO: 1) in the nucleotide sequence of FIGS. 2A to 2S;

FIG. 4 is comprised of FIGS. 4A, 4B and 4C showing an amino acid sequence (TomL) (SEQ ID NO: 3) encoded by a region tomL (nucleotides 446 to 1437 of SEQ ID NO: 1) in the nucleotide sequence of FIGS. 2A to 2S;

FIG. 5 is an amino acid sequence (TomM) (SEQ ID NO: 4) encoded by a region tomM (nucleotides 1470 to 1739 of SEQ ID NO: 1) in the nucleotide sequence of FIGS. 2A to 2S;

FIG. 7 is an amino acid sequence (TomO) (SEQ ID NO: 6) encoded by a region tomO (nucleotides 3341 to 3697 of SEQ ID NO: 1) in the nucleotide sequence of FIGS. 2A to 2S;

FIG. 9 is an amino acid sequence (TomQ) (SEQ ID NO: 8) encoded by a region tomO (nucleotides 4797 to 5132 of SEQ ID NO: 1) in the nucleotide sequence of FIGS. 2A to 2S;

FIG. 10 is a nucleotide sequence (SEQ ID NO: 9) of a first primer employed in Example 6;

FIG. 11 is a nucleotide sequence (SEQ ID NO: 10) of a second primer employed in Example 6;

FIG. 12 is a nucleotide sequence (SEQ ID NO: 11) of a third primer employed in Example 6; and FIG. 13 is a nucleotide sequence (SEQ ID NO: 12) of a fourth primer employed in Example 6.

FIG. 14 is a nucleotide sequence (SEQ ID NO: 13) of a tom-KB primer employed in Example 7.

FIG. 15 is a nucleotide sequence (SEQ ID NO: 14) of a tom-KBT primer employed in Example 7.

DETAILED DESCRIPTION OF THE PREFERRED EMBODIMENTS

Figure 1:
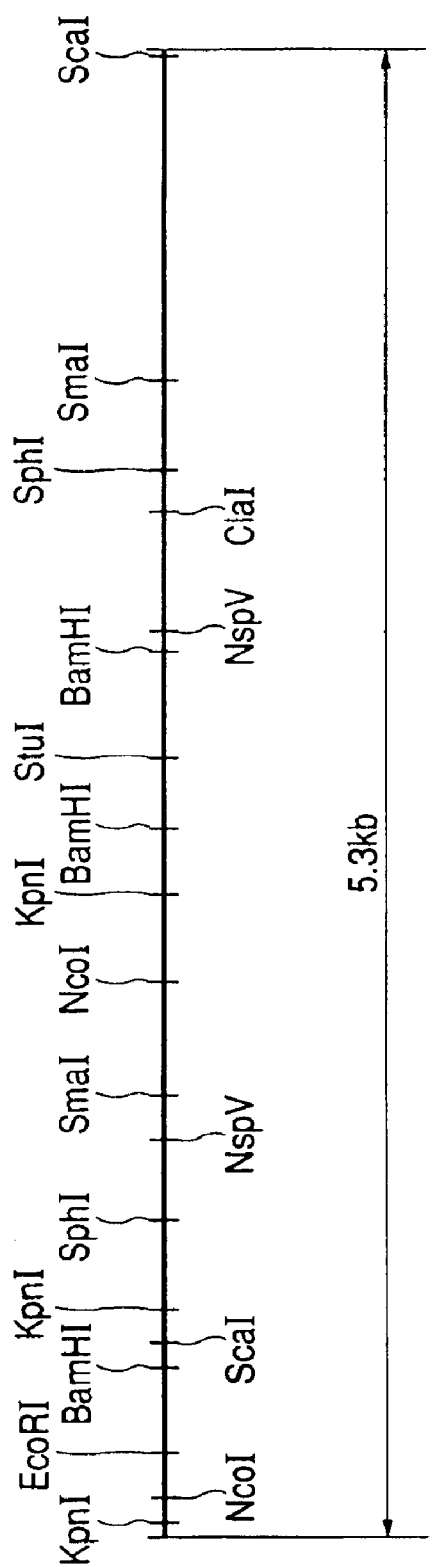
FIG. 1 shows a restriction map of a DNA fragment of about 5.3 Kb carrying a toluene monooxygenase gene; of about 5.3 Kb carrying a toluene monooxygenase gene.
Figures 6, 6A:
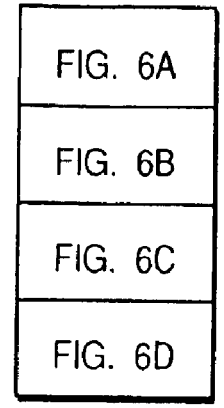
FIG. 6 is comprised of FIGS. 6A, 6B, 6C and 6D showing an amino acid sequence (TomN) (SEQ ID NO: 5) encoded by a region tomN (nucleotides 1777 to 3324 of SEQ ID NO: 1) in the nucleotide sequence of FIGS. 2A to 2S.
Figures 8, 8A:
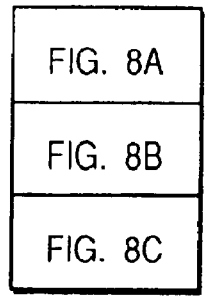
FIG. 8 is comprised of FIGS. 8A, 8B and 8C showing an amino acid sequence (TomP) (SEQ ID NO: 7) encoded by a region tomP (nucleotides 3737 to 4795 of SEQ ID NO: 1) in the nucleotide sequence of FIGS. 2A to 2S.

The DNA fragment containing a toluene monooxygenase gene according to the present invention is isolated from *Ralstonia eutropha* strain TB64 (FERM BP-6933, hereinafter referred to as Strain TB64). The microbiological characteristics and culture conditions of Strain TB64 are described later.

Strain TB64 can be cultured, for example, by inoculating an M9 liquid medium containing 0.1% yeast extract and 2 mM phenol with a colony of strain TB64 grown on an M9 agar medium supplemented with 0.2% yeast extract, followed by culture at 30° C. In this case, culture period of about 20 hours is suitable.

Isolation of the DNA fragment according to the present invention is achieved by partial digestion of the total DNA of Strain TB64 with a restriction enzyme Sau3AI. Specifically, total DNA can be prepared by the standard method, in which the above microorganism is grown in a suitable medium, for example, LB medium (containing 10 g of tryptone, 5 g of yeast extract, and 5 g of sodium chloride in 1 litter) and then cells are disrupted, for example, in the presence of sodium dodecyl sulfate (SDS) at 70° C. The total DNA is then partially digested by Sau3AI to obtain a DNA fragment containing about 5.8 Kb region carrying a toluene monooxygenase gene. The DNA fragment thus obtained is ligated to a plasmid vector completely digested by BamHI, for example, pUC18, and the recombinant vector is introduced into competent cells of, for example, *E. coli* JM109, prepared by the Hanahan method to obtain transformants. Then, transformants can be selected by a suitable method, for example, by culturing cells on an LB medium plate containing ampicillin.

In order to select a transformant containing a recombinant vector carrying a toluene monooxygenase gene from the above transformants, it is preferable to add cresol, phenol, or the like to LB medium for transformant selection in advance. The transformant carrying a toluene monooxygenase gene can be selected as brown colonies, since these substrates are monooxygenated by toluene monooxygenase to produce methylcatechol or catechol which is then autooxidized to develop color. Alternatively, after culturing cells on an ordinary LB medium plate, various substrates may be sprayed onto the plate to select brown colonies in a similar manner.

The isolated DNA fragment of about 5.3 Kb has the following restriction sites:

| Restriction Enzyme | Number of Restriction Sites |
| --- | --- |
| BamHI | 3 |
| ClaI | 1 |
| EcoRI | 1 |
| KpnI | 3 |
| NcoI | 2 |
| NspV | 2 |
| ScaI | 2 |
| SmaI | 2 |
| SphI | 2 |
| StuI | 1 |

The DNA fragment has no DraI, EcoRV, HindIII, HpaI, NdeI, NheI, PvuII, SacI, Sse8387I, XbaI or XhoI restriction site.

The restriction map of the DNA fragment of the present invention is as shown above. Toluene monooxygenase genes derived from *Burkholderia cepacia* G4 5223 PR1 (U.S. Pat. No. 5,543,317), derived from *Burkholderia* sp. JS150 (Appl. Environ. Microbiol., 61, 3336 (1995), derived from *Pseudomonas pickettii* PK01 (J. Bacteriol., 176, 3749 (1994)), and derived from *Pseudomonas mendocina* KR1 (J. Bacteriol., 173, 3010 (1991)) were reported. Phenol hydroxylases reported to have a similar structure are derived from *Acinetobacter calcoaceticus* NCIIB8250 (Mol. Microbiol., 18, 13 (1995)), *Pseudomonas* sp. CF600 (J. Bacteriol., 172, 6826 (1990)), *Pseudomonas* spp. (J. Bacteriol., 177, 1485 (1995)), and *Pseudomonas putida* P35X (Gene, 151, 29 (1994)). The DNA fragment of the present invention has, however, a restriction map different from any of those. It is thus clear that the DNA fragment of the present invention contains a novel toluene monooxygenase gene.

Although the DNA fragment thus obtained can sufficiently enables the degradation of aromatic compounds and/or halogenated aliphatic hydrocarbon compounds even in pUC18, it can be integrated in an expression vector or a vector of a wide host range to improve the degradation ability or to be optimized for the treatment site.

The plasmid according to the present invention can be constructed from following elements:

1) Toluene monooxygenase gene;
2) Marker gene (drug-resistance, auxotrophic complement, or the like); and
3) Vector containing an autonomous replication sequence (plasmid, or the like).

As the toluene monooxygenase gene, the DNA fragment of about 5.3 kb as shown above can be employed by itself, or a constitution containing elements necessary for a toluene monooxygenase activity can be also employed, for example, with or without spacer sequences. Further, each element can be varied with the proviso that its function is not impaired. These variations can be attained by changing DNA sequences encoding them.

As the drug-resistance genes, an ampicillin resistance gene, a kanamycin (G418, neomycin) resistance gene, a tetracycline resistance gene, a chloramphenicol resistance gene, a hygromycin resistance gene can be employed. For auxotrophic complement, a gene sequence to supply the nutrient required by the host organism is used. Typically, a gene enabling the synthesis of the required amino acid is utilized.

As the autonomous replication sequences, a sequence derived from plasmid RSF1010, which can function as a wide host range replication region in most of the gram-negative bacteria, can be employed. It can be also employed vector pBBR122 (Mo Bi Tec) containing a wide host range replication region which does not belong to any incompatible groups, IncP, IncQ, or IncW or the like.

For the recombinant plasmid according to the present invention, various promoters and terminators can be employed and various factors can be further introduced to improve and control the ability of degrading aromatic compounds and/or halogenated aliphatic hydrocarbon compounds. Specifically, promoters such as lac, trc, tac T3, and T7 can be employed. As a terminator, an rrnB operon terminator or the like can be employed. Also, introduction of a repressor gene such as lacIq and a lac operator enables expression control with an inducer such as isopropyl thiogalactoside (IPTG). Alternatively, the absence of these suppressor and operator as elements, enables constitutive expression of degradation activity. In addition, a temperature-sensitive control system or the like can be employed.

For recombination of a DNA fragment containing the toluene monooxygenase gene into an expression vector containing these regulating elements, natural restriction sites can be utilized as it is, or restriction sites may be newly created by site-directed mutagenesis or a polymerase chain reaction using a primer involving base substitution. In general, recombination into an expression vector often utilizes NcoI restriction sites. It is convenient to design so as to create an NcoI restriction site in the initiation codon ATG or GTG region by site-directed mutagenesis or primer design. Known methods using an adaptor can be employed. For optimization of expression, the DNA fragment may be properly deleted using exonuclease III or Bal31 nuclease. As described above, molecular biological techniques suitable for the purpose can be employed for recombination into an expression vector.

As a method for introducing the recombinant plasmid carrying a desired gene into a host organism, any methods that can introduce a foreign gene into a host can be employed, and known methods, for example, the calcium chloride method, the electroporation method, and the conjugation transfer method can be employed.

In the present invention, any microorganisms can be used as a host organism so long as it can express the aromatic compounds and/or halogenated aliphatic hydrocarbon compounds-degrading activity after the introduction of the recombinant plasmid, including the genera *Escherichia, Pseudomonas, Burkholderia, Acinetobacter, Moraxella, Alcaligenes, Vibrio, Nocardia, Bacillus, Lactobacillus, Achromobacter, Arthrobacter, Micrococcus, Mycobacterium, Methylosinus, Methylomonas, Welchia, Methylocystis, Nitrosomonas, Saccharomyces, Candida, Torulopsis*, and *Ralstonia*.

In addition, the aromatic compounds and/or halogenated aliphatic hydrocarbon compounds-degrading microorganisms such as strain J1, strain JM1, *Pseudomonas* sp. strain TL1, strain KK01, *Pseudomonas alcaligenes* strain KB2, *Alcaliqenes* sp. strain TL2, and *Vibrio* sp. strain KB1 can be employed as a host. These strains have been deposited in the National Institute of Bioscience and Human Technology, Agency of Industrial Science and Technology of Japan. The date of deposit, Accession No., and microbiological characteristics of these strains are shown below.

<Strain KK01 (Deposit Date: Mar. 11, 1992, Accession No. FERM BP-4235)>
A. Morphological Characteristics
(1) Gram staining: Negative
(2) Size and shape: Rod of 1.0–2.0 μm in length and 0.5 μm in width
(3) Motility: Motile B. Growth on Various Culture Media

| Medium | Growth temperature (° C.) | Growth |
|---|---|---|
| Blood agar medium | 37 | + |
| Lactose agar medium | 37 | + |
| Chocolate agar medium | 37 | ++ |
| GMA | 37 | − |
| Scyllo | 37 | − |
| Standard agar medium | 4 | − |
| Standard agar medium | 25 | ± |
| Standard agar medium | 37 | + |
| Standard agar medium | 41 | ± |

C. Physiological Characteristics
(1) Aerobic or anaerobic: Obligate aerobic
(2) Sugar degradation mode: Oxidation
(3) Oxidase production: +
(4) Silver nitrate reduction: +
(5) Hydrogen sulfide production: −
(6) Indole production: −
(7) Urease production: −
(8) Gelatin liquefaction: −
(9) Arginine hydrolysis: −
(10) Lysine decarboxylation: +
(11) Ornithine decarboxylation: −
(12) Utilization of citric acid: +
(13) Methyl carbinol acetyl reaction (VP reaction): −
(14) Detection of tryptophan deaminase: −
(15) ONPG:
(16) Assimilation of carbohydrates
  Glucose: +
  Fructose: +
  Maltose: +
  Galactose: +
  Xylose: +
  Mannitol: ±
  Sucrose: −
  Lactose: +
  Esculin: −
  Inositol: −
  Sorbitol: −
  Rhamnose: −
  Melibiose: −
  Amygdalin: −
  L-(+)-arabinose: +

Strain J1 (Deposit Date: May 25, 1994, Accession No. FERM BP-5102)
A. Morphological Characteristics
  Gram staining: Positive
  Size and shape of cells: Polymorphous rod of 1–6 μm in length and about 0.5–2 μm in width
  Mobility: Negative
  Colony: Cream to light pink, sticky
B. Growth on Various Media
  BHIA: Good growth
  MacConkey: No growth
C. Optimal Temperature for Growth: 25° C.>30° C.>35° C.
D. Physiological Characteristics
  Aerobic or anaerobic: aerobic
  TSI (slant/butt): Alkaline/alkaline, H$_2$S (−)
  Oxidase: Negative Catalase: Positive
Sugar fermentation
  Glucose: Negative
  Sucrose: Negative
  Raffinose: Negative
  Galactose: Negative
  Maltose: Negative
Urease: Positive
Esculin: Positive
Nitric acid: Negative Strain JM1 (Deposit Date: Jan. 10, 1995, Accession No. FERM BP-5352)
Gram staining and morphology: Gram-negative rod
Growth on various media
  BHIA: Good growth
  MacConkey: Possible to grow
Colony color: Cream
Optimal temperature for growth: 25° C.>30° C.>35° C.
Mobility: Negative (semi-fluid medium)
TSI (slant/butt): Alkaline/alkaline, $H_2S$ (−)
Oxidase: Positive (weak)
Catalase: Positive
Sugar fermentation
  Glucose: Negative
  Sucrose: Negative
  Raffinose: Negative
  Galactose: Negative
  Maltose: Negative
Urease: Positive
Esculin hydrolysis (β-glucosidase): Positive
Nitrate reduction: Negative
Indole production: Negative
Glucose acidification: Negative
Arginine dehydrase: Negative
Gelatin hydrolysis (protease): Negative
β-Galactosidase: Negative
Assimilation of compounds
  Glucose: Negative
  L-Arabinose: Negative
  D-Mannose: Negative
  D-Mannitol: Negative
  N-Acetyl-D-glucosamine: Negative
  Maltose: Negative
  Potassium gluconate: Negative
  n-Capric acid: Positive
  Adipic acid: Negative
  dl-Malic acid: Positive
  Sodium citrate: Positive
  Phenyl acetate: Negative Strain TL1 (Deposit Date: Jan. 10, 1995, Accession No. FERM P-14726/FERM BP-6923.
A. Gram Staining and Morphology: Gram-Negative Rod
B. Growth on Various Media
  Standard agar: Good growth
  MacConkey agar: Poor growth
C. Optimal Temperature for Growth: 25° C.>35° C.
D. Physiological Characteristics
  Aerobic/anaerobic: Aerobic
  TSI (slant/butt): Alkaline/alkaline, $H_2S$ (−)
  Oxidase: Positive
  Catalase: Positive
  Oxidation/fermentation test: −/−
  Potassium nitrate reduction: Negative
  Indole production from L-tryptophan: Negative
  Glucose acidification: Negative
  Arginine dehydrase: Negative
  Urease: Negative
  Esculin hydrolysis (β-glucosidase): Negative
  Gelatin hydrolysis (protease): Negative
  β-Galactosidase: Negative
  Cytochrome oxidase: Positive
E. Assimilation of Sugars, Organic Acids, etc.
  Glucose: Positive
  L-Arabinose: Positive
  D-Mannose: Negative
  D-Mannitol: Positive
  N-Acetyl-D-glucosamine: Negative
  Maltose: Negative
  Potassium gluconate: Positive
  n-Capric acid: Negative
  Adipic acid: Positive
  dl-Malic acid: Negative
  Sodium citrate: Negative
  Phenyl acetate: Negative Strain TL2 (Deposit Date on Nov. 15, 1994, Accession No. FERM BP-6913.
A. Gram Staining and Morphology: Gram-Negative Rod
B. Growth on Various Media
  Standard agar: Good growth
  MacConkey agar: Poor growth
C. Optimal Temperature for Growth: 25° C.>35° C.
D. Physiological Characteristics
  Aerobic/anaerobic: Aerobic
  TSI (slant/butt): Alkaline/alkaline, $H_2S$ (−)
  Oxidase: Positive
  Catalase: Positive
  Oxidation/fermentation test: −/−
  Potassium nitrate reduction: Positive
  Indole production from L-tryptophan: Negative
  Glucose acidification: Negative
  Arginine dehydrase: Negative
  Urease: Negative
  Esculin hydrolysis (β-glucosidase): Negative
  Gelatin hydrolysis (protease): Negative
  β-Galactosidase: Negative
  Cytochrome oxidase: Positive
E. Assimilation of Sugars, Organic Acids, etc.
  Glucose: Negative
  L-Arabinose: Negative
  D-Mannose: Negative
  D-Mannitol: Negative
  N-Acetyl-D-glucosamine: Negative
  Maltose: Negative
  Potassium gluconate: Positive
  n-Capric acid: Positive
  Adipic acid: Positive
  dl-Malic acid: Positive
  Sodium citrate: Positive
  Phenyl acetate: Positive Strain KB1 (Deposit date: Nov. 15, 1994, Accession No. FERM BP-6914.

A. Gram Staining and Morphology: Gram-Negative Rod
B. Growth Conditions on Various Media
   Standard agar: Good growth
   MacConkey agar: Good growth
C. Optimal Temperature for Growth: 25° C.>35° C.
D. Physiological Characteristics
   Aerobic/anaerobic: Aerobic
   TSI (slant/butt): Alkaline/alkaline, H2S (−)
   Catalase: Positive
   Oxidation/fermentation test: −/−
   Potassium nitrate reduction: Positive
   Indole productivity from L-tryptophan: Negative
   Glucose acidification: Negative
   Arginine dehydrase: Positive
   Urease: Positive
   Esculin hydrolysis (β-glucosidase): Negative
   Gelatin hydrolysis (protease): Negative
   β-Galactosidase: Negative
   Cytochrome oxidase: Positive
E. Assimilation of Sugars, Organic Acids, etc.
   Glucose: Negative
   L-Arabinose: Negative
   D-Mannose: Negative
   D-Mannitol: Negative
   N-Acetyl-D-glucosamine: Positive
   Maltose: Negative
   Potassium gluconate: Positive
   n-Capric acid: Positive
   Adipic acid: Positive
   dl-Malic acid: Positive
   Sodium citrate: Negative
   Phenyl acetate: Positive
Strain KB2 (Deposit Date: Nov. 15, 1994, Accession No. FERM BP-5354)
A. Gram Staining and Morphology: Gram-Negative Rod
B. Growth on Various Media
   Standard agar: Good growth
   MacConkey agar: Good growth
C. Optimal Temperature for Growth: 25° C.>35° C.
   Growth at 42° C.: Good
D. Physiological Characteristics
   Aerobic/anaerobic: Aerobic
   TSI (slant/butt): Alkaline/alkaline, $H_2S$ (−)
   Catalase: Positive
   Oxidation/fermentation test: −/−
   Potassium nitrate reduction: Positive
   Indole production from L-tryptophan: Negative
   Glucose acidification: Negative
   Arginine dehydrase: Negative
   Urease: Negative
   Esculin hydrolysis (β-glucosidase): Negative
   Gelatin hydrolysis (protease): Negative
   β-Galactosidase: Negative
   Cytochrome oxidase: Positive
E. Assimilation of Sugars, Organic Acids, etc.
   Glucose: Negative
   L-Arabinose: Negative
   D-Mannose: Negative
   D-Mannitol: Negative
   N-Acetyl-D-glucosamine: Negative
   Maltose: Negative
   Potassium gluconate: Positive
   n-Capric acid: Negative
   Adipic acid: Positive
   dl-Malic acid: Positive
   Sodium citrate: Negative
   Phenyl acetate: Negative

*Burkholderia cepacia* strain KK01 was once classified into genus *Pseudomonas* but reclassified into genus *Burkholderia* since *Pseudomonas cepacia* has been taxonomically changed to *Burkholderia cepacia*. The deposited strain KK01 itself, however, is the same.

Strain J1 is an aromatic compound-assimilating bacterium which degrades organic halogenated compounds with the participation of oxygenase. In spite of its excellent ability of degrading organic halogenated compounds that it can almost completely degrade about 20 ppm of TCE at a low temperature of 15° C. close to natural environment such as soil, it requires aromatic compounds such as phenol, toluene, and cresol as a degradation inducer. Strain JM1 was obtained by nitrosoguanidine mutagenization of strain J1, and has the same microbiological characteristics as the parental strain J1 except that it can degrade organic halogenated compounds in the absence of aromatic compounds such as phenol, toluene, and cresol as a degradation inducer.

In order to exploit the microbial degrading ability more effectively, it is preferable to select the host microorganism for recombinants from the microorganisms isolated to the environment to be treated, more preferably a dominant microorganism in the environment, considering environmental adaptation of the recombinant. Generally, in the natural world, microorganisms that have existed in an environment will adapt to the environment most probably, and the probability of the survival of foreign microorganisms introduced into the environment is not high. On the other hand, when a very strong microorganism is introduced from outside, it may disturb the existing ecosystem. Thus, the use of the indigenous microorganisms as a host is a superior method in environmental adaptability, survival, and safety.

A transformant to which a recombinant plasmid has been introduced may be cultured in the conditions suitable for the growth of the host. For example, a carbon and nitrogen source such as yeast extract, tryptone, and peptone, and a inorganic salt such as sodium chloride and potassium chloride can be used. An M9 medium (containing 6.2 g of $Na_2HPO_4$, 3.0 g of $KH_2PO_4$, 0.5 g of NaCl, and 1.0 g of $NH_4Cl$ in 1 litter) supplemented with various minerals and suitable carbon sources such as sodium malate, sodium succinate, sodium lactate, sodium pyruvate, sodium glutamate, sodium citrate, etc. can also be employed. Further, yeast extract, tryptone, peptone, etc. can be used in combination. The pH of the growth medium and culture temperature can be adjusted to those suitable for the host microorganism, although pH of about 5–9 and culture temperature of 15–37° C. are generally preferable.

A transformant containing a recombinant DNA carrying a toluene monooxygenase gene can be suitably employed for the treatment to degrade at least either halogenated aliphatic hydrocarbon compounds or aromatic compounds (hereinafter referred to as "pollution compounds") contained in a medium. In other words, the degradation treatment for the pollution compounds according to the present invention can be carried out by bringing the transformant into contact with the pollution compounds in an aqueous medium, soil, or a gas phase. Any method can be used to contact the degrading transformant with the pollution compounds so long as the transformant can express the degrading activity. Various methods such as a batch method, semi-continuous method, and continuous method can be employed. Semi-immobilized or immobilized transformant on an appropriate carrier can be also used. The environments such as polluted water, drainage, waste water, soil, and gas phase can be treated by various methods, as required. These treatment methods are described below.

The degradation treatment of the pollution compounds in an aqueous medium according to the present invention can be carried out by contacting the degrading transformant with the pollution compounds in the aqueous medium. The representative treating methods are described below. However, the method according to the present invention is not limited thereto.

The simplest method is, for example, to introduce the degrading transformant directly into an aqueous medium contaminated with the pollution compounds. In this case, it is preferable to optimize the pH, salt temperature of the aqueous medium, and the concentrations of the pollution compounds in accordance with the degrading transformant.

As another application mode, the degrading transformant is grown in a culture vessel, and an aqueous medium containing the pollution compounds is introduced into the vessel at a predetermined flow rate for degradation of these compounds. The aqueous medium can be introduced and discharged, continuously, intermittently or batch-wise according to the treatment capacity. It is preferable to optimize the system by a system control in accordance to the concentrations of the pollution compounds.

Alternatively, the degrading microorganism may be first attached to a carrier such as soil particles and the filled in a reactor vessel, to which an aqueous medium containing the pollution compounds is introduced for degradation treatment. In this case, any carrier can be employed not restricted to soil particles, but carriers having a high capacity to retain the transformant and not preventing aeration are preferable. To provide the transformant with habitats, it can be used various bioreactor carriers, for example, those conventionally employed in the pharmaceutical industry, food industry, and wastewater treatment systems. More specifically, there can be used inorganic particulate carries such as porous glass, ceramics, metal oxides, activated carbon, kaolinite, bentonite, zeolite, silica gel, alumina, and anthracite; gel carries such as starch, agar, chitin, chitosan, polyvinyl alcohol, alginic acid, polyacrylamide, carrageenan, and agarose; ion-exchange cellulose, ion-exchange resins, cellulose derivatives, glutaraldehyde, polyacrylic acid, polyurethane, polyester, or the like. As natural materials, cellulose materials such as cotton, hemp, and papers, and lignin materials such as saw dust and barks can be employed.

The degradation treatment of the pollution compounds in soil according to the present invention can be carried out by bringing the degrading transformant in contact with the pollution compounds in the soil. The representative treating methods are described below. However, the method according to the present invention is not limited thereto.

The simplest method is, for example, to introducing degrading transformant directly into the soil polluted with the pollution compounds. Introduction of the transformant may be carried out by spraying it on the surface of the soil and, for the treatment of rather deeper underground, by introducing it through the well arranged in the underground, wherein the application of pressure of air, water, etc. allows the transformant to spread over the wide area of the soil and makes the process more effective. When the transformant is introduced into soil, it is necessary to adjust various conditions of the soil so that they are suitable for the transformant used for the process.

Further, there is such a method that first the transformant is attached to a carrier, next the carrier is put in a reaction vessel, and then the reaction vessel is introduced into, primarily, the aquifer of the contaminated soil, to undergo degradation treatment. The form of the reaction vessel is desirably like a fence or a film which can cover the wide area of the soil. Any carrier can be used, but it is preferable to use those having an excellent retention of transformant and not inhibiting aeration. As a material of the carrier, which can provide suitable habitats for the transformant, for example, it can be used various bioreactor carriers, for example, those conventionally employed in the pharmaceutical industry, food industry, and wastewater treatment systems.

According to the present invention, the degradation treatment of the pollution compounds in gas phase can be achieved by contacting the transformant with the contaminants in the gas phase. The representative modes are shown below, but are not intended to limit the present invention.

One mode is, for example, such that the degradation transformant is cultured in a culture vessel, and then the gas containing the pollution compounds is introduced into the vessel at a given flow rate to undergo degradation treatment. The method for introducing the gas is not limited specifically, but it is desirably such that introduction of the gas causes agitation of the culture medium and promote its aeration. Introduction and discharge of the gas may be carried out continuously, or it may be carried out intermittently according to the degradation capacity. A batch method is also applicable. Preferably such control is systematized in accordance with the concentrations of the pollution compounds to give optimum results.

Another mode is such that the transformant is attached to a carrier like soil particles, next the carrier is put into a reaction vessel, and then the gas containing the pollution compounds is introduced into the vessel to undergo degradation treatment. Besides particles of soil, any carrier can be used, however, it is desirable to use those having an excellent retention of transformant and not inhibiting aeration. As a material of the carrier, which can provide suitable habitats for transformant, for example, it can be used various bioreactor carriers, for example, those conventionally employed in the pharmaceutical industry, food industry, and wastewater treatment systems.

As materials which can retain the degrading transformant and supply it with nutrient, many examples can be found in the compost used in the agriculture, forestry and fisheries. Specifically, dry materials from plants, such as straw of grains, sawdust, rice bran, bean curd lees, bagasse and so on, and seafood wastes, such as shells of crabs and lobster and so on are applicable.

In cleaning of contaminated gas, the degrading transformant may be introduced after the carrier material is packed. To make the degradation reaction efficient, it is preferable that the above-mentioned nutrient, water content, oxygen concentration, etc. are kept in desirable conditions for the growth of the transformant. The ratio of the carrier to water in a reaction vessel may be determined considering the growth of the transformant and aeration. The shape of the vessel may be selected considering the amount and concentration of the gas to be treated, but preferably it is designed to enhance the contact of the gas with the transformant held on the carrier. For example, column, tube, tank and box type can be used as the reaction vessel. The vessel of these forms may be joined together with an exhaust duct and a filter to form one unit, or plural vessels may be connected according to the capacity.

Polluted gas is sometimes adsorbed by the carrier material in the beginning of the reaction and there is very few case where the effect of utilizing transformant may not be exhibit. After a certain period of time, however, it is said that the pollutants adhered to the carrier material is degraded, and further contaminants can be adsorbed by the surface of the carrier material which has restored adsorption capacity. Thus, a constant decomposition rate is expected without saturation of the pollutant-eliminating ability.

The method according to the present invention is applicable for the treatment of waste liquid, soil and air in a closed system or open system. Moreover, transformant may be immobilized on a carrier, or various methods promoting their proliferation may be employed in combination.

The present invention is explained more specifically by means of the following examples.

The complete taxonomical description of Strain TB64 (FERM BP-6933) is as follows:
1. Morphological Characteristics
Shape and dimension: Rod (0.3 to 0.5 μm in width, 1.0 to 2.0 μm in length)
Sporulation: No spore
Flagellation: Peritrichous flagella
Gram stain: Negative (18 hr, 24 hr, 36 hr)
2. Physiological and Biological Properties:
Anaerobic growth: Negative
Catalase: Positive
oxidase: Negative
Litmus milk: Alkali
Reduction of Nitrate: Negative
V-P reaction: Negative
pH of V-P medium: pH 7.76
Casein hydrolysis: Negative
Gelatin digestion: Negative
Starch hydrolysis: Negative
DNA hydrolysis: Negative
Urea hydrolysis: Negative
Tween 20 hydrolysis: Negative
Tween 40 hydrolysis: Negative
Tween 60 hydrolysis: Negative
Tyrosine hydrolysis: Positive
Utilization of organic acids
Citric acid: Positive
Propionic acid: Positive
Acetic acid: Positive
Fumaric acid: Positive
L-malic acid: Positive
Succinic acid: Positive
Utilization of inorganic nitrogen:
Ammonium salts: positive
Nitrates: Positive
Indole production: Negative
H$_2$S production: Negative
Pigment production on various media:
P agar: Negative
F agar: Negative
King A agar: Negative
King B agar: Negative
Growth in the presence of NaCl:
2%: Positive
5%: Negative
7%: Negative
Growth pH: 5.0–9.0
Growth temperature: 10° C.–40° C.

Growth in the presence of 0.02% sodium azide: negative
Growth in the presence of 0.001% lysozyme: positive
OF test: negative
Production of acid from sugars:
    Glucose: negative
    Arabinose: negative
    Fructose: negative
    Galactose: negative
    Maltose: negative
    Lactose: negative
    Sucrose: negative
    Xylose: negative
    Trehalose: negative
    Glycerol: negative
    Mannitol: negative
    Sorbitol: negative
    Sorbose: negative
    Mannose: negative
    Rhamnose: negative
    Adonitol: negative
Gas production:
    Glucose: negative
    Arabinose: negative
    Xylose: negative
    Mannitol: negative.
3. Compositional Analysis of Quinones
Ubiquinone 8: 95.4%

EXAMPLE 1

Cloning of Toluene Monooxygenase Gene of Strain TB64

Cells of strain TB64 (FERM BP-6933) which can assimilate toluene were cultured in 100 ml of LB medium (containing 10 g of tryptone, 5 g of yeast extract, and 5 g of sodium chloride in 1 liter) overnight, harvested and washed with 100 mM phosphate buffer (pH 8.0). To the cells thus obtained, 10 ml of STE (10 mM tris (pH 8.0)/1 mM EDTA/100 mM sodium chloride) and 1 ml of 10% sodium dodecyl sulfate (final concentration of about 1%) were added. After the cells were incubated at 70° C. for 30 minutes for lysis, phenol treatment and ethanol sedimentation were carried out. DNA thus obtained was dissolved in a 10 mM tris (pH 8.0)/1 mM EDTA buffer (TE).

The DNA thus obtained was dissolved at various concentrations and treated with a restriction enzyme Sau3AI (Takara Shuzo Co., Ltd.) at 37° C. for 15 minutes for partial digestion. Aliquots of the partial digestion products were applied to gel electrophoresis on 0.8% agarose gel to identify the samples almost digested to about 5–10 kb. These samples were applied to spin column HR-400 (Amarsham-Pharmacia) to purify DNA fragments.

The DNA fragments were ligated to plasmid pUC18 (Takara Shuzo Co., Ltd.) completely digested with a restriction enzyme BamHI (Takara Shuzo Co., Ltd.) and dephosphorylated with bovine alkaline phosphatase (Takara Shuzo Co., Ltd.), using DNA Ligation Kit Ver. 2 (Takara Shuzo Co., Ltd.). Recombinant plasmids thus prepared were then introduced into the host *E. coli* HB101 (Takara Shuzo Co., Ltd.), and the cells were cultured on LB agar plates containing 100 μg/ml of ampicillin as a selection agent and 200 ppm phenol as an indicator for toluene monooxygenase activity. About 15,000 colonies of transformants grew on the plates.

Three brown colonies were found in these colonies and picked up. Recombinant plasmid DNA carrying toluene monooxygenase gene was extracted from the cells of each brown colony and the restriction map thereof was determined. It was found that all recombinant plasmids derived from the three colonies had a common insertion fragment of 5.3 kb. A plasmid containing only the common fragment of 5.3 kb was designated as pTB64 and a restriction map of the inserted DNA fragment was made (See FIG. 1). A recombinant *E. coli* HB101 carrying a plasmid containing a 6.1 kb insertion fragment containing this common 5.3 kb fragment was deposited in the National Institute of Bioscience and Human Technology, Agency of Industrial Science and Technology in accordance with the Budapest Treaty under the accession No. FERM BP-6942. Its microbiological characteristics were identical to those of *E. coli* HB101 except that it can degrade aromatic compounds and halogenated aliphatic hydrocarbon compounds.

In order to confirm that the inserted DNA fragment of pTB64 was derived from strain TB64, southern hybridization was performed. DNA was extracted from strain TB64 and completely digested with NcoI (Takara Shuzo Co., Ltd.) or KpnI (Takara Shuzo Co., Ltd.), and then subjected to southern hybridization. The inserted DNA fragment of pTB64 was digested with EcoRI-SphI (Takara Shuzo Co., Ltd.) to obtain a DNA fragment of about 0.8 kb, and this was used as a probe. As a result, a strong signal was observed around 1.8 kb with the NcoI-digested DNA, and around 0.8 and 1.5 kb with the KpnI digested DNA, in a good agreement with the lengths of the fragments predicted from the restriction map. Consequently, it was confirmed that the toluene monooxygenase gene contained in pTB64 was derived from the strain TB64.

EXAMPLE 2

Monooxygenation by *E. coli* HB101(pTB64)

The cells of *E. coli* HB101(pTB64) were inoculated in 100 ml of LB medium, cultured at 37° C. overnight, harvested, washed, and then resuspended in 100 ml of M9 medium (6.2 g of $Na_2HPO_4$, 3.0 g of $KH_2PO_4$, 0.5 g of NaCl, and 1.0 g of $NH_4Cl$ per liter) supplemented with a mineral stock solution of the following composition (3 ml/liter of M9 medium)(referred to as M9+mineral solution).
Composition of Mineral Stock Solution
Nitrilotriacetic acid: 1.5 g
$MgSO_4$: 3.0 g
$CaCl_2$: 0.1 g
$Na_2MoO_4$: 0.1 g
$FeSO_4$: 0.1 g
$MnSO_4$: 0.5 g
NaCl: 1.0 g
$ZnSO_4$: 0.1 g
$CuSO_4$: 0.1 g
$AlK(SO_4)_2$: 0.1 g
$H_3BO_3$: 0.1 g
$NiCl_2$: 0.1 g
Distilled water (to 1,000 ml)

Then, 27.5 ml vials were prepared, and 10 ml aliquot of the above suspension was placed in each vial, which was then tightly sealed with a teflon-coated butyl rubber stopper and aluminum seal. Gaseous toluene or benzene was introduced into each vial with a syringe to a concentration of 100 ppm (a concentration supposing all toluene or benzene completely dissolved in the aqueous phase in the vial). After incubation at 30° C. for 3 hours, 1 ml aliquot was taken from each vial, and cells were removed by centrifugation and substances of 10,000 or higher in molecular weight were removed by ultrafiltration. Production of ortho-cresol and 3-methylcatechol from toluene and phenol and catechol from benzene was confirmed by HPLC, to show that toluene and benzene are monooxygenated by toluene monooxygenase encoded by the cloned DNA fragment.

EXAMPLE 3

Degradation of Aromatic Compounds and Halogenated Aliphatic Hydrocarbon Compounds by *E. coli* HB101(pTB64)

The cells of *E. coli* HB101(pTB64) cultured as described in Example 2 were suspended in M9+mineral solution. 10 ml aliquots of the suspension were placed in 27.5 ml vials. Each vial was tightly sealed with a teflon-lined butyl rubber stopper and an aluminum seal. Gaseous trichloroethylene (TCE), cis-1,2-dichloroethylene (cis-1,2-DCE), trans-1,2-dichloroethylene (trans-1,2-DCE), 1,1-dichloroethylene (1,1-DCE), toluene, and benzene were injected into respective vials to a concentration of 25 ppm (a concentration supposing the introduced substance completely dissolved in the aqueous phase in the vial). The vials were shaken and incubated at 30° C. The concentrations of the respective compounds in the gas phase were measured by gas chromatography after 6 hours. The results are shown in Table 1. *E. coli* HB101 harboring pUC18 (*E. coli* HB101(pUC18)) was employed as a control and degradation was evaluated in the same manner.

Similarly, phenol, ortho-cresol, meta-cresol and para-cresol were introduced into respective 27.5 ml vials each containing 10 ml of the cell suspension at a concentration of 50 ppm. Each vial was tightly sealed with a butyl rubber stopper and aluminum seal. The vials were shaken and incubated at 30° C. The quantities of the respective compounds in the liquid phase were determined by the amino antipyrine method with a spectrophotometer to obtain their concentrations after 6 hours. The results are shown in Table 2. *E. coli* HB101(pUC18) was employed as a control and degradation was evaluated in the same manner.

The above results show that *E. coli* HB101(pTB64) had an excellent ability to degrade aromatic compounds and halogenated aliphatic hydrocarbon compounds.

EXAMPLE 4

Definition of Toluene Monooxygenase Region

The toluene monooxygenase region was defined further by stepwise deletion or subcloning of plasmid pTB64 obtained in Example 1 using restriction sites thereof. Toluene monooxygenase activity was evaluated by the method in Example 3, and 25 ppm toluene was employed as a substrate.

First, a subclone pTB64 ΔBamHI in which a top 0.7-kb fragment was deleted was prepared from pTB64 using the ScaI sites at 0.7 kb and 5.3 kb. More specifically, pTB64 was completely digested by restriction enzymes ScaI (Takara Shuzo Co., Ltd.) to obtain three fragments of about 0.9 kb, 2.4 kb and 4.6 kb. The fragments were separated by agarose gel electrophoresis, and the 4.6 kb fragment was cut out and recovered from the gel and purified with a spin column HR-400 (Amarsham-Pharmacia). The fragment was ligated to pUC18 previously completely digested by HincII enzymes, and *E. coli* HB101 was transformed with the recombinant plasmid according to the conventional method.

E. coli HB101 cells were then applied on an LB plate containing 100 μg/ml of ampicillin to select transformants. From the cells grown overnight in LB medium, plasmid DNA was extracted by an alkaline method to confirm the presence of pTB64ΔScaI, and a transformant carrying pTB64 ΔScaI was isolated. E. coli HB101 (pTB64ΔScaI) cells were evaluated for toluene monooxygenase activity. No degradation of toluene was observed, indicating that the 0.7-kb fragment is essential for toluene monooxygenase activity.

Then, a subclone pTB64ΔEcoRI was prepared by deleting a 0.3 kb fragment from pTB64 using the 0.3 kb EcoRI restriction site of pTB64. More specifically, pTB64 was partially digested by restriction enzyme EcoRI, and then self-ligated to transform E. coli HB101. The E. coli HB101 transformants were then selected on an LB plate containing 100 μg/ml of ampicillin. After the transformants were cultured in LB medium overnight, the plasmid DNA was extracted from the cells by the alkaline method to confirm the presence of pTB64ΔEcoRI and a transformant carrying pTB64ΔEcoRI was isolated. E, coli HB101(pTB64ΔEcoRI) was evaluated for toluene monooxygenase activity. Degradation of toluene was observed, but the activity was lower than that of E. coli HB101(pTB64), indicating that the 0.3 kb fragment was not essential for toluene monooxygenase activity but necessary for full expression of the activity.

Further, the stepwise deletion method was employed to restrict the toluene monooxygenase region from the opposite direction. More specifically, stepwise deletion was introduced from the XbaI restriction site using XbaI (Takara Shuzo Co., Ltd.) restriction site and Sse8387I (Takara Shuzo Co., Ltd.) restriction site of pUC18. The stepwise deletion was carried out using Deletion Kit for Kilo-Sequence (Takara Shuzo Co., Ltd.) according to the attached protocol. The results of the activity evaluation of various deletion clones thus obtained show that the region up to 4.8 kb is essential for expression of the activity and a region from 4.8 kb to 5.3 kb is not especially required for degradation activity.

EXAMPLE 5

Sequencing of Toluene Monooxygenase Gene

The nucleotide sequence of pTB64 was determined as follows. pTB64 was digested by various restriction enzymes and subcloned into pUC18 plasmid. Deletion clones were prepared from pTB64 or subclones of partial pTB64 using Deletion Kit for Kilo-Sequence (Takara Shuzo Co., Ltd.) to determine the nucleotide sequence of the 5.3 kb fragment encoding toluene monooxygenase by the dideoxy method. The dideoxy method was carried out using ABI PRISM Cycle Sequencing Kit (Perkin Elmer Corporation) according to the attached protocol for reaction conditions, etc. DNA recombination and Kilo-Sequence method were also performed according to the conventional methods or the manufacturer's protocols attached. The results of sequencing show that the DNA encoding toluene monooxygenase is contained in 5,331 bases comprised of 7 coding regions as shown by SEQ ID NO: 1; a region tomK encoding the amino acid sequence TomK of SEQ ID NO: 2; a region tomL encoding the amino acid sequence TomL of SEQ ID NO: 3; a region tomM encoding an amino acid sequence TomM of SEQ ID NO: 4; a region tomN encoding an amino acid sequence TomN of SEQ ID NO: 5; a region tomO encoding an amino acid sequence TomO of SEQ ID NO: 6; a region tomP encoding an amino acid sequence TomP of SEQ ID NO: 7 and a region tomO encoding an amino acid sequence TomQ encoding an amino acid sequence TomQ of SEQ ID NO: 8.

Here, considering the results of Example 4 together, the polypeptide (TomK)(SEQ ID NO: 2) encoded by tomK is not essential for expression of the activity but the presence of TomK clearly enhances the toluene monooxygenase activity. It is, therefore, desirable for sufficient expression of the activity that TomK is present as a component of toluene monooxygenase. The polypeptide (TomQ)(SEQ ID NO: 8) encoded by tomQ is not essential for expression of the activity. In addition, the toluene monooxygenase activity is not affected by the presence of TomQ. Thus, it is not essential to contain TomQ as a component of toluene monooxygenase.

In other words, any DNA fragment containing segments encoding the amino acid sequences of SEQ ID NOs: 3–7 as the components of toluene monooxygenase where these segments are aligned so that expressed TomL to TomP having the amino acid sequences of SEQ ID NOs: 3–7 can form a protein with a toluene monooxygenase activity is included in the preferred DNA fragment of the present invention. DNA fragments with variation in at least one segment of the DNA fragment with the proviso that the activity of toluene monooxygenase is not impaired are included in the preferred DNA fragments of the present invention.

DNA fragments further containing a region encoding the amino acid sequence TomK of SEQ ID NO: 2 or a variant in which the amino acid sequence of SEQ ID NO: 2 is altered with the proviso that it does not impair the property to enhance a toluene monooxygenase activity are also included in the preferred embodiment of the present invention.

EXAMPLE 6

Recombination of Toluene Monooxygenase Gene into Expression Vectors-(1)

As expression vectors, pSE280 (Invitrogen), and pSE380 (Invitrogen) were employed. They contain an ampicillin-resistant gene as a marker, and pSE280 and pSE380 have a sequence derived from ColE1 as ori. All these two vectors contain a trc promoter and a rrnB terminator, and a ribosome-binding site is located before the NcoI restriction site. lacIq is contained in pSE380 but not in pSE280.

To incorporate the toluene monooxygenase gene into these vectors, NcoI restriction sites were introduced in tomK and tomL. The following 4 primers (Amarsham-Pharmacia) were prepared to introduce the NcoI restriction site by PCR:

```
1) tom-K                                       SEQ ID NO:9
5'-AGCGACCCATTCACCATGGCCCTGCAGACCCCAG-3'         34 mer 2) tom-L                                       SEQ ID NO:10
5'-CTCAGGAGCAACCCATGGCAATCGAGCTGAAAAC-3'         34 mer 3) tomΔNcoI                                    SEQ ID NO:11
5'-TACTTCCAGTACGCGTCGATGGTCAGGCGGAACG-3'         34 mer 4) tail                                        SEQ ID NO:12
5'-GCCCAGCTTTGCCATGGCGGCGAGCAGCGATTCG-3'         34 mer
```

The tom-K was designed to introduce the NcoI restriction site at the first ATG site (bases 200–202 in the Sequence Listing) of tomK. Similarly, tom-L was designed to introduce the NcoI site at the first GTG site (bases 446–448 in the SEQ ID NO: 1) of tomL. The tomΔNcoI was designed to perish the NcoI site in the toluene monooxygenase gene (about 1.95 kb). Using primer combinations of the primer (3) with the respective primers (1) and (2) and the recombinant plasmid DNA of FERM BP-6942 as the template, PCR was performed. PCR was carried out by using Takara LA PCR Kit Ver. 2 (Takara Shuzo Co., Ltd.) with a reaction volume of 50 μl, and the reaction was started at 94° C. for 1 minute and then a reaction cycle of 98° C. for 20 seconds followed by 72° C. for 5 minutes was repeated for 30 times (shuttle PCR), and then followed by reaction at 72° C. for 10 minutes. The reaction conditions were according to the manufacturer's protocol.

As a result, the combinations of the primers (1) and (3), and (2) and (3) gave the PCR products of about 1.8 kb, and about 1.5 kb, respectively. Then, using these products as the primer in combination with the primer (4) respectively, PCR was carried out. The reaction conditions were the same as the above. As a result, the combinations of the primers ((1)–(3)) and (4), and ((2)–(3)) and (4) gave the PCR products of about 4.8 kb, and about 4.5 kb, respectively. The respective DNA fragments were digested with the restriction enzyme NcoI (Takara Shuzo Co., Ltd.). It was confirmed that the NcoI site in the oxygenase had completely disappeared. These NcoI-digested products were purified using a spin column HR-4000 (Amarsham-Pharmacia) and used for the following ligation reaction.

The above-mentioned expression vector were completely digested with the restriction enzyme NcoI, dephosphorylated, subjected to phenol treatment, and purified with a spin column HR-400 (Amarsham-Pharmacia). The vectors were then ligated to NcoI-digested PCR products to transform *E. coli* HB101 (Takara Shuzo Co., Ltd.) according to the conventional method. The transformed *E. coli* HB101 cells were then grown on LB plate containing 100 μg/ml of ampicillin for transformant selection. After the transformants were cultured in LB liquid medium at 37° C. overnight, plasmid DNA was extracted by the alkaline method to examine the recombinant plasmids. Transformants in which the respective PCR fragments were accurately inserted into the NcoI restriction site of the respective expression vectors were obtained.

A list of the obtained recombinant plasmids are shown in Table 3.

EXAMPLE 7

Recombination of Toluene Monooxygenase Gene into Expression Vectors-(2)

A recombinant vector to express only TomK was constructed using pSTV28 (TaKaRa) as the expression vector. Since pSTV28 contains a chloramphenicol resistance gene as a marker and an ori derived from pACYC, it is compatible with pSE280 or pSE380 in the same cell. pSTV28 does not contain lacIq. BamHI sites were introduced upstream and downstream tomK in order to incorporate a gene encoding TomK into this vector. Two primers (Amarsham-Pharmacia Biotec) were prepared to introduce BamHI sites by PCR.

```
5) tom-KB                                    SEQ ID NO: 13
   5'-CAATGAAAGGGGATCCGAGGCGACATCGAC-3'   30 mer 6) tom-KBT                                   SEQ ID NO: 14
   5'-ATGTCGACGGGATCCAGCTCGATTGTCACG-3'   30 mer
```

Here, tom-KB was designed to introduce a BamHI site upstream SD sequence of tomK, tom-KBT was designed to introduce a BamHI site downstream the termination codon of tomK.

Using primer combinations of the primers (5) and (6) and the recombinant plasmid DNA of FERM BP-6942 as the template, PCR was performed. PCR was carried out by using Takara LA PCR Kit Ver. 2 (Takara Shuzo Co., Ltd.) with a reaction volume of 50 μl, and the reaction was started at 94° C. for 1 minute and then a reaction cycle of 98° C. for 20 seconds followed by 72° C. for 5 minutes was repeated for 30 times (shuttle PCR), and then followed by reaction at 72° C. for 10 minutes. The reaction conditions were according to the manufacturer's protocol.

As a result, a 0.3 kb PCR product was obtained. Then, the product was completely digested by BamHI (Takara Shuzo Co., Ltd.) and purified using a spin column HR-4000 (Amarsham-Pharmacia) and used for the following ligation reaction.

The above-mentioned pSTV28 was completely digested with the restriction enzyme BamHI, dephosphorylated, subjected to phenol treatment, and purified with a spin column HR-400 (Amarsham-Pharmacia). The vector was then ligated to BamHI-digested PCR product to transform *E. coli* HB101 (Takara Shuzo Co., Ltd.) according to the conventional method. The transformed *E. coli* HB101 cells were then grown on LB plate containing 25 μg/ml chloramphenicol for transformant selection. After the transformants were cultured in LB liquid medium at 37° C. overnight, plasmid DNA was extracted by the alkaline method to examine the recombinant plasmids. Transformants in which the PCR fragment was accurately inserted into the BamHI restriction site of pSTV28 were obtained. The obtained recombinant plasmid was designated as pKS-64.

EXAMPLE 8

Ability of *E. coli* HB101 Recombinants to Degrade Aromatic Compounds and Halogenated Aliphatic Hydrocarbon Compounds (without Induction with IPTG)

The cells of the *E. coli* strains, each harboring one of the 4 recombinant plasmids obtained as described in Example 6, were inoculated in 100 ml of LB medium, cultured at 37° C. overnight, harvested, washed, and suspended in an M9+mineral solution. 10 ml aliquots of the suspension were put in 27.5 ml vials, and each vial was tightly sealed with a Teflon-coated butyl rubber stopper and aluminium seal. Then, gaseous trichloroethylene (TCE), cis-1,2-dichloroethylene (cis-1,2-DCE), trans-1,2-dichloroethylene (trans-1,2-DCE), 1,1-dichloroethylene (1,1-DCE), toluene, and benzene were added to respective vials with a syringe to a concentration of 50 ppm (supposing all of the introduced substance dissolved in the aqueous phase in the vial). The vials were shaken and incubated at 30° C. The concentrations of the respective compounds in the gas phase after 6 hour incubation were measured by gas chromatography. The results are shown in Table 4. *E. coli* HB101 harboring no plasmid was employed as a control and degradation was evaluated in the same manner.

Similarly, phenol, ortho-cresol, meta-cresol and para-cresol were introduced into respective 27.5 ml vials each containing 10 ml of the cell suspension at a concentration of 50 ppm. Each vial was tightly sealed with a butyl rubber stopper and aluminum seal. The vials were shaken and incubated at 30° C. The quantities of the respective compounds in the liquid phase were determined by the aminoantipyrine method with a spectrophotometer to determine their concentrations after 6 hours. The results are shown in Table 5. *E. coli* HB101 harboring no plasmid was employed as a control and degradation was evaluated in the same manner.

The above results confirm that *E. coli* HB101 recombinants containing toluene monooxygenase gene have an excellent ability to degrade the aromatic compounds and halogenated aliphatic hydrocarbon compounds. It is shown that transformants harboring pSE380-derived monooxygenase expression vectors express a lower degrading activity in a system not containing IPTG than those harboring pSE280-derived plasmids, since pSE280 lacks lacIq.

EXAMPLE 9

Ability of *E. coli* HB101 Recombinants to Degrade Aromatic Compounds and Halogenated Aliphatic Hydrocarbon Compounds (with Induction with IPTG)

Each *E. coli* HB101 transformant strain harboring one of the four recombinant plasmids obtained as described in Example 6, was inoculated in 100 ml of LB medium, cultured at 37° C. to reach $OD_{600}$ of about 0.8, and then IPTG was added to 1 mM concentration followed by further incubation at 37° C. for 5 hours. Then the cells were harvested, washed and suspended in an M9+mineral solution. Ten ml aliquots of the suspension were placed in 27.5 ml vials, and each vial was tightly sealed with a Teflon-coated butyl rubber stopper and aluminium seal. Then, gaseous trichloroethylene (TCE), cis-1,2-dichloroethylene (cis-1,2-DCE), trans-1,2-dichloroethylene (trans-1,2-DCE), 1,1-dichloroethylene (1,1-DCE), toluene, and benzene were added to respective vials with a syringe to a concentration of 50 ppm (supposing all of the introduced substance dissolved in the aqueous phase in the vial). The vials were shaken and incubated at 30° C. The concentrations of the respective compounds in the gas phase after 6 hour incubation were measured by gas chromatography. The results are shown in Table 6. *E. coli* HB101 harboring no plasmid was employed as a control and degradation was evaluated in the same manner. Similarly, phenol, ortho-cresol, meta-cresol and para-cresol were introduced into respective 27.5 ml vials each containing 10 ml of the cell suspension, at a concentration of 50 ppm. Each vial was tightly sealed with a butyl rubber stopper and aluminum seal. The vials were shaken and incubated at 30° C. The quantities of the respective compounds in the liquid phase were determined by the amino antipyrine method with a spectrophotometer to determine their concentrations after 6 hours. The results are shown in Table 7. *E. coli* HB101 harboring no plasmid was employed as a control and degradation was evaluated in the same manner.

The above results confirm that *E. coli* HB101 recombinants containing toluene monooxygenase gene have an excellent ability to degrade aromatic compounds and halogenated aliphatic hydrocarbon compounds. It is shown that transformants harboring pSE380-derived expression vectors for the monooxygenase show more excellent degrading activity by IPTG induction.

EXAMPLE 10

Ability of *E. coli* HB101 Recombinants to Degrade Aromatic Compounds and Halogenated Aliphatic Hydrocarbon Compounds (without Induction with IPTG)(2)

Two *E. coli* HB101 transformants harboring pL2-64 and pL3-64 recombinant plasmids respectively obtained in Example 6 were treated by the calcium chloride method to further transform them with pKS-64 obtained in Example 7.

Transformation was carried conventionally and transformants were selected by spreading the cells onto an LB agar medium containing 25 μg chloramphenicol and 100 μg/ml ampicillin. The cells of each transformant were inoculated in 100 ml of LB medium, cultured at 37° C. overnight, harvested, washed, and suspended in an M9+mineral solution. 10 ml aliquots of the suspension were placed in 27.5 ml vials, and each vial was tightly sealed with a Teflon-coated butyl rubber stopper and aluminium seal. Then, gaseous trichloroethylene (TCE), cis-1,2-dichloroethylene (cis-1,2-DCE), trans-1,2-dichloroethylene (trans-1,2-DCE), 1,1-dichloroethylene (1, -DCE), toluene, and benzene were added to respective vials with a syringe to a concentration of 50 ppm (supposing all of the introduced substance dissolved in the aqueous phase in the vial). The vials were shaken and incubated at 30° C. The concentrations of the respective compounds in the gas phase after 6 hour incubation were measured by gas chromatography. The results are shown in Table 8. *E. coli* HB101 harboring no plasmid was employed as a control and degradation was evaluated in the same manner.

Similarly, phenol, ortho-cresol, meta-cresol and para-cresol were introduced into respective 27.5 ml vials each containing 10 ml of the cell suspension at a concentration of 50 ppm. Each vial was tightly sealed with a butyl rubber stopper and aluminum seal. The vials were shaken and incubated at 30° C. The quantities of the respective compounds in the liquid phase were determined by the aminoantipyrine method with a spectrophotometer to determine their concentrations after 6 hours. The results are shown in Table 9. *E. coli* HB101 harboring no plasmid was employed as a control and degradation was evaluated in the same manner.

The above results confirm that *E. coli* HB101 recombinants containing the toluene monooxygenase gene have an excellent ability to degrade the aromatic compounds and volatile halogenated aliphatic hydrocarbon compounds. It has been also shown that excellent degradation of the pollution compound can be achieved when TomK and TomLMNOP are expressed from different systems. It is shown that transformants harboring pSE380(tomLMNOP) plasmid express a lower degrading activity in a system not containing IPTG than those harboring pSE280 (tomLMNOP) plasmid, since pSE380 contains lacIq.

EXAMPLE 11

Ability of *E. coli* HB101 Recombinants to Degrade Aromatic Compounds and Halogenated Aliphatic Hydrocarbon Compounds (with Induction with IPTG)(2)

Each *E. coli* HB101 transformant strain harboring combination of two plasmids obtained in Example 10 was inoculated in 100 ml of LB medium, cultured at 37° C. to reach $OD_{600}$ of about 0.8, and then IPTG was added to 1 mM concentration followed by further incubation at 37° C. for 5 hours. Then the cells were harvested, washed and suspended in an M9+mineral solution. 10 ml aliquots of the suspension were placed in 27.5 ml vials, and each vial was tightly sealed with a Teflon-coated butyl rubber stopper and aluminium seal. Then, gaseous trichloroethylene (TCE), cis-1,2-dichloroethylene (cis-1,2-DCE), trans-1,2-dichloroethylene (trans-1,2-DCE), 1,1-dichloroethylene (1,1-DCE), toluene, and benzene were added to respective vials with a syringe to a concentration of 50 ppm (supposing all of the introduced substance dissolved in the aqueous phase in the vial). The vials were shaken and incubated at 30° C. The concentrations of the respective compounds in the gas phase after 6 hour incubation were measured by gas chromatography. The results are shown in Table 10. *E. coli* HB101 harboring no plasmid was employed as a control and degradation was evaluated in the same manner.

Similarly, phenol, ortho-cresol, meta-cresol and para-cresol were introduced into respective 27.5 ml vials each containing 10 ml of the cell suspension, at a concentration of 50 ppm. Each vial was tightly sealed with a butyl rubber stopper and aluminum seal. The vials were shaken and incubated at 30° C. The quantities of the respective compounds in the liquid phase were determined by the amino antipyrine method with a spectrophotometer to determine their concentrations after 6 hours. The results are shown in Table 11. *E. coli* HB101 harboring no plasmid was employed as a control and degradation was evaluated in the same manner.

The above results confirm that *E. coli* HB101 recombinants containing the monooxygenase gene have an excellent ability to degrade the aromatic compounds and volatile halogenated aliphatic hydrocarbon compounds. It has been also shown that excellent degradation of the pollution compound can be achieved when TomK and TomLMNOP are expressed from different systems. It is shown that transformants harboring pSE380(tomLMNOP) plasmid express higher degrading activity in a system containing IPTG.

EXAMPLE 12

TCE Degradation by *E. coli* HB101(pK2-64) and HB101(pK3-64) Recombinants in Soil (without IPTG Induction)

*E. coli* HB101(pK2-64) and HB101(pK3-64) recombinant strains as described in Example 6 were respectively inoculated in 10 ml of LB medium and cultured at 37° C. overnight. 50 g of Sawara sieved sand (unsterilized) was placed in 68 ml vials each. 5 ml of LB medium inoculated with the above seed culture to 100:1, was then added to the sand in each vial. Each vial was cotton-plugged, and incubated at 37° C. for 8 hours without shaking. After that, each vial was tightly sealed with a Teflon-coated butyl rubber stopper and aluminum seal. Gaseous TCE was introduced into the vials with a syringe to 50 ppm (supposing all TCE dissolved into the aqueous phase in the vial). The vials were incubated at 30° C. Quantitative analysis of TCE in the gas phase were carried out by gas chromatography after 6 hours to determine TCE concentrations. The results are shown in Table 12. *E. coli* HB101 harboring no plasmid was employed as a control and evaluated in the same manner.

The above results confirm that *E. coli* HB101 transformants harboring pK2-64 and pK3-64 also show an excellent TCE-degrading ability in soil. It is shown that transformant harboring pK3-64 (pSE380-based) expresses a lower degrading activity in a system not containing IPTG than that harboring pSE280-derived plasmid pK2-64, since the former contains lacIq.

EXAMPLE 13

TCE Degradation by *E. coli* Recombinants HB101 (pK2-64) and HB101(pK3-64) in Soil (with IPTG Induction)

The cells of *E. coli* HB101(pK2-64) and HB101(pK3-64) recombinant strains as described in Example 6 were respectively inoculated in 10 ml of LB medium and cultured at 37° C. overnight. Fifty grams of Sawara sieved sand (unsterilized) were placed in 68 ml vials each. 5 ml of LB medium inoculated with the above seed culture to 100:1, was then added to the sand. Each vial was cotton-plugged, and incubated at 37° C. for 4 hours without shaking. Then 1 ml of a 10 mM IPTG solution was added to each vial. After that, each vial was tightly sealed with a Teflon-coated butyl rubber stopper and aluminum seal. Gaseous TCE was introduced into the vials with a syringe to 50 ppm (supposing all TCE dissolved into the aqueous phase in the vial). The vials were incubated at 30° C. Quantitative analysis of TCE in the gas phase were carried out by gas chromatography after 6 hours to determine TCE concentrations. The results are shown in Table 13. *E. coli* HB101 harboring no plasmid was employed as a control and evaluated in the same manner.

The above results confirm that *E. coli* recombinants HB101(pK2-64) and HB101(pK3-64) also show an excellent TCE-degrading ability in soil. It is shown that the recombinant harboring pK3-64 (pSE380-based) expresses higher degrading activity with IPTG induction.

EXAMPLE 14

TCE Degradation by Recombinants *E. coli* HB101 (pK2-64) and HB101(pK3-64) in Gas Phase (without IPTG Induction)

The cells of respective recombinant strains, *E. coli* HB101 (pK2-64) and HB101(pK3-64) as described in Example 6, were inoculated in 100 ml of LB medium and cultured at 37° C. overnight. Aliquots (30 ml) of each seed culture were transferred into 68 ml vials, into which air which had passed through a saturation TCE solution was introduced at a flow rate of 20 ml/min for 10 minutes. Each vial was tightly sealed with a Teflon-coated butyl rubber stopper and aluminum seal, and shaking culture was conducted at 30° C. Quantitative analysis of TCE in the gas phase were carried out by gas chromatography to determine its concentration after 6 hours. The results are shown in Table 14. *E. coli* HB101 harboring no plasmid was employed as a control and degradation was evaluated in the same manner.

The above results confirm that recombinants *E. coli* HB101(pK2-64) and HB101(pK3-64) show an excellent TCE-degrading ability also in the gas phase. It is shown that the recombinant harboring pK3-64 (pSE380-based) expresses a lower degrading activity in a system not containing IPTG than that harboring pSE280-derived plasmid pK2-64, since the former contains lacIq.

EXAMPLE 15

TCE Degradation by Recombinants *E. coli* HB101 (pK2-64) and HB101(pK3-64) in Gas Phase (with IPTG Induction)

*E. coli* (HB101) recombinant strains each harboring pK2-64 or pK3-64 as described in Example 6 were respectively inoculated into 100 ml of LB medium and cultured at 37° C. to reach $OD_{600}$ of about 0.8, and then IPTG was added to 1 mM concentration followed by further incubation at 37° C. for 5 hours. Aliquots (30 ml) of the cell suspension were transferred into 68 ml vials, into which air which had passed through in a saturated TCE solution was introduced at a flow rate of 20 ml/min for 10 minutes. Each vial was tightly sealed with a Teflon-coated butyl rubber stopper and aluminum seal, and shaking culture was conducted at 30° C. Quantitative analysis of TCE in the gas phase were carried out by gas chromatography to determine its concentration after 6 hours. The results are shown in Table 15. *E. coli* HB101 harboring no plasmid was employed as a control and degradation was evaluated in the same manner.

The above results confirm that recombinants *E. coli* HB101(pK2-64) and HB101(pK3-64) show an excellent

EXAMPLE 16

Introduction of Recombinant Plasmid containing Toluene Monooxygenase Gene into *Alcaligenes* sp. strain TL2 (FERM BP-6913)

The toluene monooxygenase gene beginning from the first ATG of tomK (base number 200–202) was transferred from a recombinant plasmid pK2-64 of Example 6 (recombinant pSE280 containing the gene) into a vector pBBR122 (Mo Bi Tec) having a wide host range replication region not belonging to an incompatible group of IncP, IncQ, and IncW. This recombinant plasmid was introduced in *Alcaligenes* sp. strain TL2 (FERM BP-6913), and its ability to degrade aromatic compounds and halogenated aliphatic hydrocarbon compounds was evaluated.

First, a wide host range recombinant plasmid was constructed. An about 6.8-kb fragment containing the toluene monooxygenase gene, a trc promoter, and a rrnB terminator was cut out from pK2-64 by complete digestion by the restriction enzyme HpaI (Takara Shuzo Co., Ltd.) followed by partial digestion by ScaI (Takara Shuzo Co., Ltd.). This fragment of 6.8 kb does not contain the lacIq sequence. As a vector of a wide host range, pBBR122 was employed. pBBR122 was completely digested with the restriction enzyme SmaI (Takara Shuzo Co., Ltd.). The 6.8 kb fragment containing the toluene monooxygenase gene, a trc promoter, and an rrnB terminator prepared as described above was ligated to the SmaI restriction site of the pBBR122 using DNA Ligation Kit Ver. 2 (Takara Shuzo Co., Ltd.) and the recombinant plasmid thus constructed was introduced into *E. coli* HB101 (Takara Shuzo Co., Ltd.). The cells of the *E. coli* thus treated were applied on LB plate containing 50 μg/ml of chloramphenicol as a selection agent. When the colonies on the plate grew to an appropriate size, the colonies were transferred by replica printing onto an LB plate containing 50 μg/ml of kanamycin as a selection agent. Transformants that could proliferate on the plate with chloramphenicol but not on the plate with kanamycin were selected, and cultured in LB medium at 37° C. overnight, to extract plasmid DNA from the cells by the alkaline method. After checking the plasmids, transformants harboring a recombinant plasmid where the 6.8 kb fragment was correctly inserted into the SmaI site of the pBBR122 were obtained. The recombinant plasmid thus obtained was about 12.1 kb in length and designated as pK2-64bbr.

The SOB medium shown below was employed for liquid culture of Alcaligenes sp. strain TL2. Chloramphenicol was used at a concentration of 50 μg/ml as a selection agent and the culture temperature was 30° C. The recombinant plasmid pK2-64 was introduced into *Alcaligenes* sp. strain TL2 cells by electroporation using a gene pulsar (Bio-Rad). The recombinant plasmid pK2-64bbr was stably retained after introduction into *Alcaligenes* sp. strain TL2.

SOB medium:
 Tryptone: 20 g
 Yeast extract: 5 g
 NaCl: 0.5 g
 250 mM KCl: 10 ml
 Distilled water (to 990 ml)
 pH 7.0

The above solution was sterilized by autoclaving and cooled to room temperature, to which 10 ml of a 2 M magnesium solution (1 M $MgSO_4.7H_2O$ + 1 M $MgCl_2.6H_2O$) separately sterilized by autoclaving was added.

EXAMPLE 17

Ability of *Alcaligenes* sp. TL2(pK2-64bbr) to Degrade Aromatic Compounds and Halogenated Aliphatic Hydrocarbon Compounds The cells of *Alcaligenes* sp. TL2(pK2-64bbr) were inoculated in 100 ml of SOB medium, cultured at 30° C. overnight, harvested, washed, and then suspended in 100 ml of M9 (containing 6.2 g of $Na_2HPO_4$, 3.0 g of $KH_2PO_4$, 0.5 g of NaCl, and 1.0 g of $NH_4Cl$ per liter) supplemented with a mineral stock solution (3 ml to 1 liter of M9 medium).

10 ml of the suspension was placed in respective 27.5 ml vials and each vial was tightly sealed with a Teflon-coated butyl rubber stopper and aluminum seal. Then, gaseous trichloroethylene (TCE), cis-1,2-dichloroethylene (cis-1,2-DCE), trans-1,2-dichloroethylene (trans-1,2-DCE), 1,1-dichloroethylene (1,1-DCE), toluene, and benzene were added to respective vials with a syringe to a concentration of 50 ppm (supposing all of the introduced substance dissolved in the aqueous phase in the vial). The vials were shaken and incubated at 30° C. The concentrations of the respective compounds in the gas phase after 6 hour incubation were measured by gas chromatography. The results are shown in Table 16. Alcaligenes sp. TL2 not containing pK2-64bbr was tested as a control and degradation was evaluated in the same manner.

Similarly, to 10 ml of the prepared cell suspension in a 27.5-ml vial, phenol, ortho-cresol, meta-cresol, and para-cresol were added to 50 ppm, respectively. The vial was tightly sealed with a butyl rubber stopper and aluminum seal, and then shaken and incubated at 30° C. The quantities of the respective compounds in the liquid phase were measured by the aminoantipyrine method with a spectrophotometer to obtain their concentrations after 6 hours. The results are shown in Table 17. *Alcaligenes* sp. strain TL2 not containing pK2-64bbr was employed as a control and degradation was evaluated in a similar system.

The above results show that the recombinant *Alcaligenes* sp. strain TL2 harboring pK2-64bbr can constitutively express the ability to degrade aromatic compounds and halogenated aliphatic hydrocarbon compounds.

EXAMPLE 18

Degradation of TCE by Recombinant *Alcaligenes* sp. TL2(pK2-64bbr) in Soil

Recombinant *Alcaligenes* sp. TL2(pK2-64bbr) as described in Example 16 was inoculated in 10 ml of SOB medium and cultured at 30° C. overnight. Fifty grams of Sawara sieved sand (unsterilized) was placed in each 68 ml vial. Five milliliter of SOB medium inoculated with the above seed culture to 100:1 was then added to the sand in each vial. Each vial was cotton-plugged and incubated at 30° C. for 12 hours without shaking. After that, each vial was tightly sealed with a Teflon-coated butyl rubber stopper and aluminum seal. Gaseous TCE was introduced into the vials with a syringe to 50 ppm (supposing all TCE dissolved into the aqueous phase in degradation was evaluated in the same manner.

The above results show that the recombinant *Alcaligenes* sp. TL2(pK2-64bbr) can constitutively express the ability to degrade TCE also in the gas phase.

According to the present invention, a DNA fragment carrying a toluene monooxygenase gene with an excellent ability to degrade aromatic compounds and halogenated aliphatic hydrocarbon compounds can be obtained. In addition, a novel recombinant plasmid containing the DNA fragment as a whole or a part thereof that can be utilized to obtain a transformant capable of degrading aromatic compounds and/or halogenated aliphatic hydrocarbon compounds can be obtained. Further, a transformant harboring the plasmid and can be utilized to degrade aromatic compounds and/or halogenated aliphatic hydrocarbon compounds can be obtained. Furthermore, a method for environmental remediation that can efficiently degrade either aromatic compounds and/or halogenated aliphatic hydrocarbon compounds by utilizing the transformant.

TABLE 1

|  | E. coliHB101(pTB64) | HB101(pUC18) |
|---|---|---|
| TCE | 0 | 25.0 |
| cis-1,2-DCE | 0 | 26.0 |
| trans-1,2-DCE | 0 | 25.0 |
| 1,1-DCE | 0 | 24.8 |
| Toluene | 0 | 27.1 |
| Benzene | 0 | 24.1 |

(Unit: ppm)

TABLE 2

|  | E. coli HB101(pTB64) | E. coli HB101(pUC18) |
|---|---|---|
| Phenol | 0 | 49 |
| Ortho-cresol | 0 | 53 |
| Meta-cresol | 0 | 51 |
| Para-cresol | 0 | 49 |

(Unit: ppm)

TABLE 3

|  | tom-K | tom-L |
|---|---|---|
| pSE280 | pK2-64 | pL2-64 |
| pSE380 | pK3-64 | pL3-64 |

TABLE 4

|  | pK2-64 | pL2-64 | pK3-64 | pL3-64 | HB101 |
|---|---|---|---|---|---|
| TCE | 0 | 42.1 | 47.3 | 49.7 | 52.1 |
| cis-1,2-DCE | 0 | 37.3 | 46.7 | 52.1 | 51.2 |
| trans-1,2-DCE | 0 | 39.2 | 47.2 | 52.0 | 55.2 |
| 1,1-DCE | 0 | 50.2 | 52.3 | 52.8 | 49.9 |
| Toluene | 0 | 36.7 | 40.8 | 48.7 | 52.5 |
| Benzene | 0 | 44.7 | 42.5 | 49.0 | 50.9 |

(Unit: ppm)

TABLE 5

|  | pK2-64 | pL2-64 | pK3-64 | pL3-64 | HB101 |
|---|---|---|---|---|---|
| Phenol | 0 | 0 | 0 | 0 | 48.1 |
| Orthocresol | 0 | 0 | 0 | 0 | 53.1 |
| Methacresol | 0 | 2.1 | 7.9 | 16.0 | 52.5 |
| Paracresol | 0 | 7.5 | 15.2 | 21.2 | 53.2 |

(Unit: ppm)

TABLE 6

|  | pK2-64 | pL2-64 | pK3-64 | pL3-64 | HB101 |
|---|---|---|---|---|---|
| TCE | 0 | 0 | 0 | 0 | 48.8 |
| cis-1,2-DCE | 0 | 0 | 0 | 0 | 54.1 |
| trans-1,2-DCE | 0 | 0 | 0 | 0 | 52.5 |
| 1,1-DCE | 0 | 10.2 | 0 | 8.3 | 52.2 |
| Toluene | 0 | 0 | 0 | 0 | 49.8 |
| Benzene | 0 | 0 | 0 | 0 | 51.0 |

(Unit: ppm)

TABLE 7

|  | pK2-64 | pL2-64 | pK3-64 | pL3-64 | HB101 |
|---|---|---|---|---|---|
| Phenol | 0 | 0 | 0 | 0 | 49.9 |
| Orthocresol | 0 | 0 | 0 | 0 | 50.2 |
| Methacresol | 0 | 0 | 0 | 0 | 50.9 |
| Paracresol | 0 | 1.8 | 0 | 5.2 | 48.0 |

(Unit: ppm)

TABLE 8

|  | pL2-64 + pKS-64 | pL3-64 + pKS-64 | HB101 |
|---|---|---|---|
| TCE | 0 | 42.2 | 53.5 |
| cis-1,2-DCE | 0 | 46.1 | 51.1 |
| trans-1,2-DCE | 0 | 45.5 | 49.8 |
| 1,1-DCE | 0 | 49.8 | 51.1 |
| Toluene | 0 | 38.3 | 50.2 |
| Benzene | 0 | 42.1 | 51.1 |

(Unit: ppm)

TABLE 9

|  | pL2-64 + pKS-64 | pL3-64 + PKS-64 | HE101 |
|---|---|---|---|
| Phenol | 0 | 0 | 50.0 |
| Orthocresol | 0 | 0 | 52.9 |
| Methacresol | 0 | 12.8 | 49.0 |
| Paracresol | 0 | 19.8 | 50.9 |

(Unit: ppm)

TABLE 10

|  | pL2-64 + pKS-64 | pL3-64 + pKS-64 | HB101 |
|---|---|---|---|
| TCE | 0 | 0 | 50.5 |
| cis-1,2-DCE | 0 | 0 | 47.9 |
| trans-1,2-DCE | 0 | 0 | 48.9 |
| 1,1-DCE | 0 | 0 | 49.2 |
| Toluene | 0 | 0 | 47.9 |
| Benzene | 0 | 0 | 52.0 |

(Unit: ppm)

TABLE 11

|  | pL2-64 + pKS-64 | pL3-64 + pKS-64 | HB101 |
|---|---|---|---|
| Phenol | 0 | 0 | 52.7 |
| Orthocresol | 0 | 0 | 50.1 |
| Methacresol | 0 | 0 | 50.3 |
| Paracresol | 0 | 0 | 51.3 |

(Unit: ppm)

TABLE 12

|     | pK2-64 | pK3-64 | HB101 |
|-----|--------|--------|-------|
| TCE | 0      | 38.2   | 48.1  |

(Unit: ppm)

TABLE 13

|     | pK2-64 | pK3-64 | HB101 |
|-----|--------|--------|-------|
| TCE | 0      | 0      | 48.0  |

(Unit: ppm)

TABLE 14

|     | pK2-64 | pK3-64 | HB101 |
|-----|--------|--------|-------|
| TCE | 0      | 37.2   | 55.0  |

(Unit: ppm)

TABLE 15

|     | pK2-64 | pK3-64 | HB101 |
|-----|--------|--------|-------|
| TCE | 0      | 0      | 52.9  |

(Unit: ppm)

TABLE 16

|             | TL2 (pK2-64bbr) | TL2  |
|-------------|-----------------|------|
| TCE         | 0               | 52.2 |
| cis-1,2-DCE | 0               | 47.2 |
| trans-1,2-DCE | 0             | 52.0 |
| 1-1,DCE     | 0               | 55.2 |
| Toluene     | 0               | 47.6 |
| Benzene     | 0               | 50.0 |

(Unit: ppm)

TABLE 17

|              | TL2 (pK2-64bbr) | TL2  |
|--------------|-----------------|------|
| Phenol       | 0               | 50.8 |
| Ortho-cresol | 0               | 54.4 |
| Meta-cresol  | 0               | 52.1 |
| Para-cresol  | 0               | 52.0 |

(Unit: ppm)

TABLE 18

|     | TL2 (pK2-64bbr) | TL2  |
|-----|-----------------|------|
| TCE | 0               | 49.9 |

(Unit: ppm)

TABLE 19

|     | TL2 (pK2-64bbr) | TL2 (pBBR122) |
|-----|-----------------|---------------|
| TCE | 0               | 51.3          |

(Unit: ppm)

---

What is claimed is:

1. An isolated DNA fragment containing a portion encoding a toluene monooxygenase, the portion comprising a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, and the regions are aligned in the order of TomL-TomM-TomN-TomO-TomP so that expressed TomL-TomP polypeptides can form an active monooxygenase protein.

2. The isolated DNA fragment according to claim 1, wherein no spacer sequence is present between the regions or at least one spacer sequence is present between the regions.

3. The isolated DNA fragment according to claim 1, further comprising a region encoding a polypeptide TomQ having an amino acid sequence of SEQ ID NO: 8 in the Sequence Listing.

4. A DNA fragment having a mutation in at least one region of the DNA fragment according to claim 1, and encoding a protein having a toluene monooxygenase activity.

5. An isolated DNA fragment comprising a region encoding a polypeptide TomK which has an amino acid sequence of SEQ ID NO: 2 and a property to enhance the toluene monooxygenase activity of a protein comprised of at least TomL to TomP aligned in the order of TomL-TomM-TomN-TomO-TomP; or a region encoding a variant TomK in which the amino acid sequence of SEQ ID NO: 2 is altered with the proviso that the property to enhance the toluene monooxygenase activity is not impaired.

6. A recombinant DNA comprising a vector, a promoter, and a DNA fragment,
wherein the vector and the promoter are functionally ligated to the DNA fragment to enable expression of the toluene monooxygenase encoded by the DNA fragment,
the DNA fragment comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing;
wherein the regions are aligned in the order of TomL-TomM-TomN-TomO-TomP.

7. The recombinant DNA according to claim 6 wherein the promoter and the vector can function in a bacterium.

8. A recombinant DNA comprising a vector, a promoter, a first DNA fragment, and a second DNA fragment;
wherein the first DNA encodes a toluene monooxygenase and comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, and
wherein the regions are aligned in the order of TomL-TomM-TomN-TomO-TomP,
the second DNA fragment encodes a polypeptide TomK having an amino acid sequence of SEQ ID NO: 2 and a property to enhance the toluene monooxygenase activity of a protein comprised of at least TomL to TomP aligned in the order of TomL-TomM-TomN-TomO-TomP; or encodes a variant TomK polypeptide in which the amino acid sequence of SEQ ID NO: 2 is altered with the proviso that the property to enhance the toluene monooxygenase activity is not impaired;

the first DNA fragment is functionally linked to the promoter to express the toluene monooxygenase activity, and the second DNA fragment is functionally linked to the promoter to express the property to enhance the activity of the toluene monooxygenase encoded by the first DNA fragment.

9. A recombinant DNA comprising a vector, a first promoter and a first DNA fragment, and a second promoter and a second DNA fragment;

wherein the first DNA comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, and wherein the regions are aligned in the order of TomL-TomM-TomN-TomO-TomP, the second DNA fragment encodes a polypeptide TomK having an amino acid sequence of SEQ ID NO: 2 and a property to enhance the toluene monooxygenase activity of a protein comprised of at least TomL to TomP aligned in the order of TomL-TomM-TomN-TomO-TomP; or encodes a variant TomK polypeptide in which the amino acid sequence of SEQ ID NO: 2 is altered with the proviso that the property to enhance the toluene monooxygenase activity is not impaired;

the first DNA fragment is functionally linked to the first promoter to express the toluene monooxygenase activity, and the second DNA fragment is functionally linked to the second promoter to express the property to enhance the activity of the toluene monooxygenase encoded by the first DNA fragment.

10. The recombinant DNA according to claim 8, wherein the promoter and the vector can function in a bacterium.

11. The recombinant DNA according to claim 9, wherein the first and second promoters and the vector can function in a bacterium.

12. A transformant obtainable by introducing into a host microorganism a recombinant DNA which comprises a vector, a promoter, and a DNA fragment, wherein the vector and the promoter are functionally ligated to the DNA fragment to enable expression of a toluene monooxygenase encoded by the DNA fragment in the host, where the DNA fragment comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, wherein the regions are aligned in the order of TomL-TomM-TomN-TomO-TomP.

13. A transformant obtainable by introducing the recombinant DNA according to claim 8 or 9 into a host microorganism.

14. The transformant according to claim 12, wherein the host microorganism is a bacterium.

15. A method for producing a toluene monooxygenase, comprising: introducing a recombinant DNA comprising a vector, a promoter, and a DNA fragment into a host cell to form a transformant, wherein the vector and the promoter are functionally ligated and the transformant produces a toluene monooxygenase encoded by said DNA fragment, wherein the DNA fragment comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, wherein the regions are aligned in the order of TomL-TomM-TomN-TomO-TomP.

16. A method for producing a toluene monooxygenase, comprising: introducing the recombinant DNA according to claim 8 or 9 in a host to enable expression of the toluene monooxygenase encoded by the first DNA fragment.

17. A method for degrading at least one of a halogenated aliphatic hydrocarbon compound and an aromatic compound comprising a degradation of at least one of a halogenated aliphatic hydrocarbon compound and an aromatic compound by the transformant according to any one of claim 12 or 14.

18. A method for degrading at least one of a halogenated aliphatic hydrocarbon compound and an aromatic compound in a medium comprising a degradation step by a transformant obtainable by introducing into a host microorganism a recombinant DNA;

wherein the recombinant DNA comprises a vector, a promoter, and a DNA fragment where the vector and the promoter are functionally ligated to the DNA fragment to enable expression of a toluene monooxygenase encoded by the DNA fragment in the host, the DNA fragment comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, wherein the regions are aligned in the order of TomL-TomM-TomN-TomO-TomP.

19. A method for degrading at least one of a halogenated aliphatic hydrocarbon compound and an aromatic compound comprising a degradation step of the compound by a transformant, wherein the transformant is obtainable by introducing into a host microorganism the recombinant DNA according to claim 8 or 9.

20. The degradation method according to claim 18, wherein the halogenated aliphatic hydrocarbon compound is a chlorinated aliphatic hydrocarbon compound.

21. The degradation method according to claim 20, wherein the halogenated aliphatic hydrocarbon compound is either trichloroethylene (TCE) or dichloroethylene (DCE).

22. The degradation method according to claim 18, wherein the aromatic compound is at least one of toluene, benzene, phenol, and cresol.

23. A method for remedying an environment polluted with a pollutant being at least either of a halogenated aliphatic hydrocarbon compound or an aromatic compound, comprising a step of degrading the pollutant by bringing a transformant into contact with the pollutant, wherein the transformant is obtainable by introducing into a host microorganism a recombinant DNA which comprises a vector, a promoter, and a DNA fragment where the vector and the promoter are functionally ligated to the DNA fragment to enable expression of a toluene monooxygenase encoded by the DNA fragment in the host, the DNA fragment comprises a region encoding a polypeptide TomL having an amino acid sequence of SEQ ID NO: 3, a region encoding a polypeptide TomM having an amino acid sequence of SEQ ID NO: 4, a region encoding a polypeptide TomN having an amino acid sequence of SEQ ID NO: 5, a region encoding a polypeptide TomO having an amino acid sequence of SEQ ID NO: 6, and a region encoding a polypeptide TomP having an amino acid sequence of SEQ ID NO: 7 of the Sequence Listing, wherein the regions are aligned in the order of TomL-TomM-TomN-TomO-TomP.

24. A method for remedying an environment polluted with a pollutant being at least either of a halogenated aliphatic hydrocarbon compound or an aromatic compound, comprising a step of degrading the pollutant by bringing a transformant into contact with the pollutant, wherein the transformant is obtainable by introducing the recombinant DNA according to claim 8 or 9.

25. The remediation method according to claim 23 wherein the environment is an aqueous medium.

26. The remediation method according to claim 25 wherein the aqueous medium is brought into contact with a carrier holding the transformant.

27. The remediation method according to claim 26 wherein the aqueous medium is brought into contact with the pollutant by placing the carrier holding the transformant in a container, introducing the polluted aqueous medium from one side of the container, and discharging the remedied aqueous medium from another side.

28. The remediation method according to claim 23, wherein the environment is soil.

29. The remediation method according to claim 28 comprising the steps of:

introducing an aqueous medium containing the transformant into the polluted soil; and supplying nutrients and/or oxygen for proliferation of the transformant in the polluted soil.

30. The remediation method according to claim 29 wherein the transformant is introduced in the soil by applying pressure through an injection well provided in the polluted soil.

31. The remediation method according to claim 28 wherein the polluted soil is introduced in a liquid phase containing the transformant.

32. The remediation method according to claim 28 wherein the polluted soil is brought into contact with a carrier holding the transformant.

33. The remediation method according to claim 23 wherein the environment is air.

34. The remediation method according to claim 33 wherein the polluted air is introduced into a liquid phase containing the transformant.

35. The remediation method according to claim 33 wherein the polluted air is brought into contact with a carrier holding the transformant.

36. The remediation method according to claim 35 wherein contact is carried out by placing the carrier holding the transformant in a container, introducing polluted air from one side of the container, and discharging cleaned air from another side.

37. The remediation method according to claim 23 wherein the halogenated aliphatic hydrocarbon compound is either trichloroethylene (TCE) or dichloroethylene (DCE).

38. The remediation method according to claim 23 wherein the aromatic compound is at least one of toluene, benzene, phenol, and cresol.

39. A component polypeptide having an amino acid sequence of SEQ ID NO: 2 in the sequence listing, capable of being a component of a toluene monooxygenase.

40. A toluene monooxygenase comprising at least component polypeptides TomL to TomP aligned in the order of TomL-TomM-TomN-TomO-TomP having amino acid sequences of SEQ ID NOs: 3 to 7 in the Sequence Listing.

41. The toluene monooxygenase according to claim 40 further comprising a component polypeptide TomK having an amino acid sequence of SEQ ID NO: 2 in the Sequence Listing.

42. The toluene monooxygenase according to claim 41 further comprising a component polypeptide TomQ having an amino acid sequence of SEQ ID NO: 8 in the Sequence Listing.

* * * * *

UNITED STATES PATENT AND TRADEMARK OFFICE
CERTIFICATE OF CORRECTION

PATENT NO. : 6,858,417 B2
DATED : February 22, 2005
INVENTOR(S) : Tetsuya Yano et al.

It is certified that error appears in the above-identified patent and that said Letters Patent is hereby corrected as shown below:

Title page, Item [54] and Column 1, line 2,
Title, "MONOOXYGENASE, GENE," should read -- MONOOXYGENASE GENE, --.

Title page,
Item [56], References Cited, OTHER PUBLICATIONS,
"Hanada et al.," reference, "Phylogen tic" should read -- Phylogenetic --.

Column 2,
Line 63, "tophane" should read -- tophan --.

Column 6,
Lines 31 and 54, "maintained" should read -- be maintained --.

Column 8,
Line 27, "loose" should read -- lose --;
Line 31, "gene; of" should read -- gene; --;
Line 32, "about 5.3 Kb carrying a toluene monooxygenase gene;" should be deleted; and
Line 65, "tomO" should read -- tomQ --.

Column 9,
Line 41, "1 litter)" should read -- 1 liter) --.

Column 10,
Line 36, "enables" should read -- enable --.

Column 11,
Line 9, "tac T3," should read -- tac, T3, --;
Line 14, "these" should read -- this --; and
Line 55, "*Alcaliqenes*" should read -- *Alcaligenes* --.

Column 13,
Line 54, "BP-6923." should read -- BP-6923) --.

Column 14,
Line 27, "BP-6913." should read -- BP-6913) --; and
Line 67, "BP-6914." should read -- BP-6914) --.

UNITED STATES PATENT AND TRADEMARK OFFICE
CERTIFICATE OF CORRECTION

PATENT NO. : 6,858,417 B2
DATED : February 22, 2005
INVENTOR(S) : Tetsuya Yano et al.

It is certified that error appears in the above-identified patent and that said Letters Patent is hereby corrected as shown below:

Column 15,
Line 8, "H2S (–)" should read -- $H_2S$ (–) --.

Column 16,
Line 46, "and a" should read -- and an --; and
Line 50, "1 litter)" should read -- 1 liter) --.

Column 17,
Line 31, "accordance to" should read -- accordance with --;
Line 34, "the filled" should read -- then filled --;
Lines 44 and 47, "carries" should read -- carriers --;
Line 53, "saw dust" should read -- sawdust --; and
Line 60, "introducing" should read -- introduce --.

Column 18,
Line 29, "promote" should read -- promotes --.

Column 19,
Line 5, "is very few case" should read -- are very few cases --; and
Line 31, "oxidase:" should read -- Oxidase: --.

Column 23,
Line 65, "tomO" should read -- tomQ --; and
Line 66, "encoding an amino acid sequence TomQ" should be deleted.

Column 25,
Line 24, "vector" should read -- vectors --.

Column 28,
Line 10, "(1, -DCE)," should read -- (1,1-DCE), --.

Column 31,
Line 50, "Alcaligenes" should read -- *Alcaligenes* --.

Column 32,
Line 24, "Alcaligenes" should read -- *Alcaligenes* --.

UNITED STATES PATENT AND TRADEMARK OFFICE
CERTIFICATE OF CORRECTION

PATENT NO.    : 6,858,417 B2
DATED         : February 22, 2005
INVENTOR(S)   : Tetsuya Yano et al.

It is certified that error appears in the above-identified patent and that said Letters Patent is hereby corrected as shown below:

Column 61,
Line 10, "first DNA" should read -- first DNA fragment --.

Signed and Sealed this

Twenty-eighth Day of February, 2006

JON W. DUDAS
*Director of the United States Patent and Trademark Office*